(12) United States Patent
Barzilai et al.

(10) Patent No.: US 8,309,525 B2
(45) Date of Patent: Nov. 13, 2012

(54) TREATMENT OF TYPE 2 DIABETES, METABOLIC SYNDROME, MYOCARDIAL INJURY AND NEURODEGENERATION WITH HUMANIN AND ANALOGS THEREOF

(75) Inventors: Nir Barzilai, Hartsdale, NY (US); Pinchas Cohen, Pacific Palisades, CA (US); Radhika Muzumdar, Mamaroneck, NY (US)

(73) Assignees: Albert Einstein College of Medicine of Yeshiva University, Bronx, NY (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/451,524

(22) PCT Filed: May 28, 2008

(86) PCT No.: PCT/US2008/006720
§ 371 (c)(1),
(2), (4) Date: Apr. 6, 2010

(87) PCT Pub. No.: WO2008/153788
PCT Pub. Date: Dec. 18, 2008

(65) Prior Publication Data
US 2010/0204099 A1 Aug. 12, 2010

Related U.S. Application Data

(60) Provisional application No. 60/932,254, filed on May 30, 2007, provisional application No. 61/010,695, filed on Jan. 10, 2008.

(51) Int. Cl.
*A61K 38/16* (2006.01)
*A61K 38/17* (2006.01)

(52) U.S. Cl. .......... 514/21.4; 514/6.7; 514/6.8; 514/6.9; 514/21.3

(58) Field of Classification Search ........................ None
See application file for complete search history.

(56) References Cited

U.S. PATENT DOCUMENTS

| | | |
|---|---|---|
| 6,277,974 B1 | 8/2001 | Lo et al. |
| 7,053,053 B2 | 5/2006 | Sugo et al. |
| 7,172,876 B2 | 2/2007 | Hinuma et al. |
| 7,314,864 B1 | 1/2008 | Nishimoto |
| 7,410,757 B1 | 8/2008 | Nishimoto |
| 7,422,862 B2 | 9/2008 | Reed et al. |
| 7,611,893 B2 | 11/2009 | Mascarenhas |
| 7,618,816 B2 | 11/2009 | Mascarenhas |
| 7,662,624 B2 | 2/2010 | Mascarenhas |
| 2005/0233413 A1 | 10/2005 | Nishimoto et al. |
| 2008/0039393 A1 | 2/2008 | Mascarenhas |
| 2008/0050352 A1 | 2/2008 | Tang et al. |
| 2008/0124346 A1 | 5/2008 | Mascarenhas |
| 2008/0125491 A1 | 5/2008 | Villegas et al. |
| 2008/0227699 A1 | 9/2008 | Chiba et al. |
| 2009/0048160 A1 | 2/2009 | Bannerman et al. |
| 2009/0053203 A1 | 2/2009 | Mascarenhas |
| 2009/0075292 A1 | 3/2009 | Reed et al. |
| 2010/0130412 A1 | 5/2010 | Cohen et al. |
| 2010/0152113 A1 | 6/2010 | Mascarenhas |
| 2010/0197599 A1 | 8/2010 | Bevec et al. |
| 2011/0039771 A1 | 2/2011 | Cohen et al. |

FOREIGN PATENT DOCUMENTS

| | | |
|---|---|---|
| EP | 1 878 745 A1 | 1/2008 |
| WO | 0181361 A1 | 11/2001 |
| WO | 02086122 A2 | 10/2002 |
| WO | 2006019365 A1 | 2/2006 |
| WO | 2009040017 A2 | 4/2009 |
| WO | 2009135165 A2 | 11/2009 |

OTHER PUBLICATIONS

Chiba et al., Molecular Neurobiology, 35:55-84, Jan. 2007.*
Matsuoka et al., CNS Drug Reviews, 12(2):113-122, 2006.*
Hashimoto Y et al., entitled "A rescue factor abolishing neuronal cell death by a wide spectrum of familial Alzheimer's disease genes and Aβ," PNAS, May 22, 2001, vol. 98, No. 11, 6336-6341.
Hashimoto Y et al., entitled "Detailed Characterization of Neuroprotection by a Rescue Factor Humanin against Various Alzheimer's Disease-Relevant Insults," The Journal of Neuroscience Dec. 1, 2001, 21(23):9235-9245.
Muzumdar R H et al., entitled "Humanin: A Novel Central Regulator of Peripheral Insulin Action," PLoS One, Jul. 2009, vol. 4, Issue 7, e6334, 1-11.
Gao, J et al., entitled "Humanin is a Novel Protector against Myocardial Infarction," Circulation, Oct. 31, 2006, Abstract 1612, p. 313, vol. 114, No. 18.
Xu, X et al., entitled "Humanin is a Novel Neuroprotective Agent Against Stroke," Stroke, 2006;37;2613-2619, Epubl. Sep. 7, 2006.
Ikonen M et al., entitled "Interaction between the Alzheimer's survival peptide humanin and insulin-like growth factor-binding protein 3 regulates cell survival and apoptosis" PNAS, vol. 100, No. 22, Oct. 28, 2003, 13042-13047.
Chan S S Y et al., entitled "Insulin-Like Growth Factor Binding Protein-3 Leads to Insulin Resistance in Adipocytes," J Clin Endocrinol Metab 90: 6588-6595, 2005.

* cited by examiner

*Primary Examiner* — Marianne P Allen
(74) *Attorney, Agent, or Firm* — Amster, Rothstein & Ebenstein LLP

(57) ABSTRACT

Provided are methods of using humanin and humanin analogs to treat a mammal exhibiting or at risk for insulin resistance, increase insulin sensitivity in a mammal exhibiting or at risk for insulin resistance, treat type-2 diabetes mellitus, metabolic syndrome, and neurodegeneration, treat and prevent myocardial injury, and determine longevity.

5 Claims, 33 Drawing Sheets

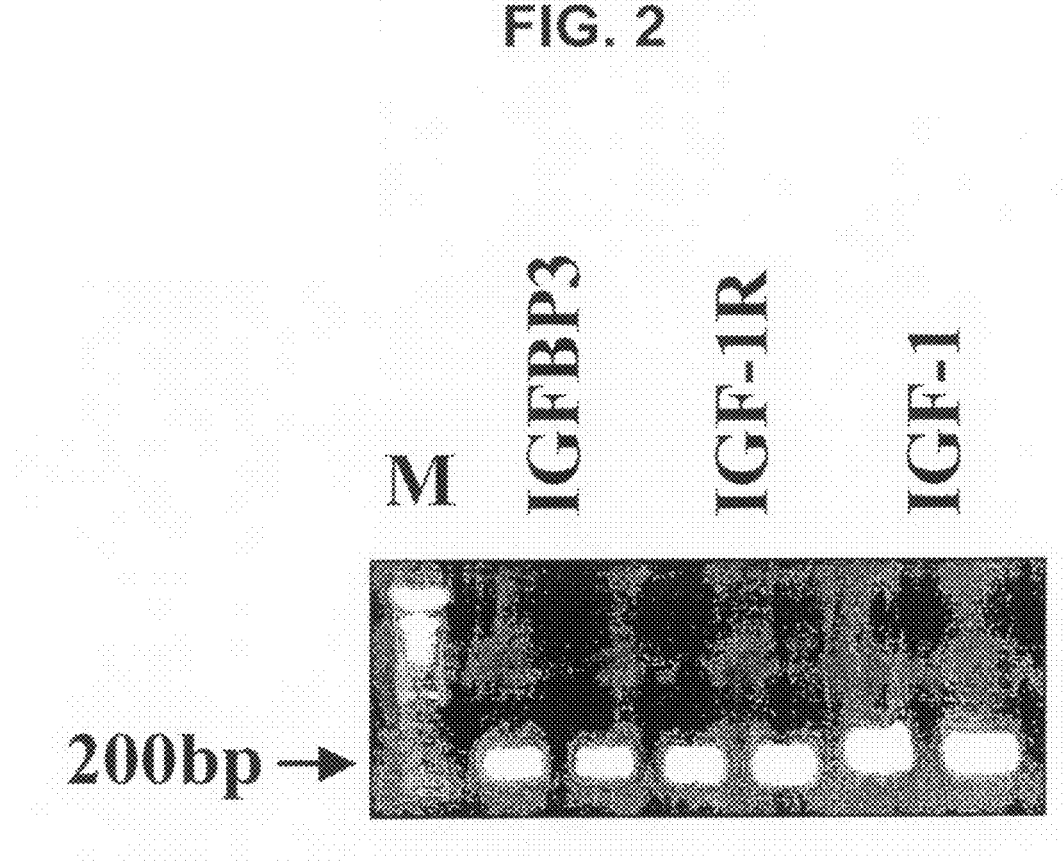

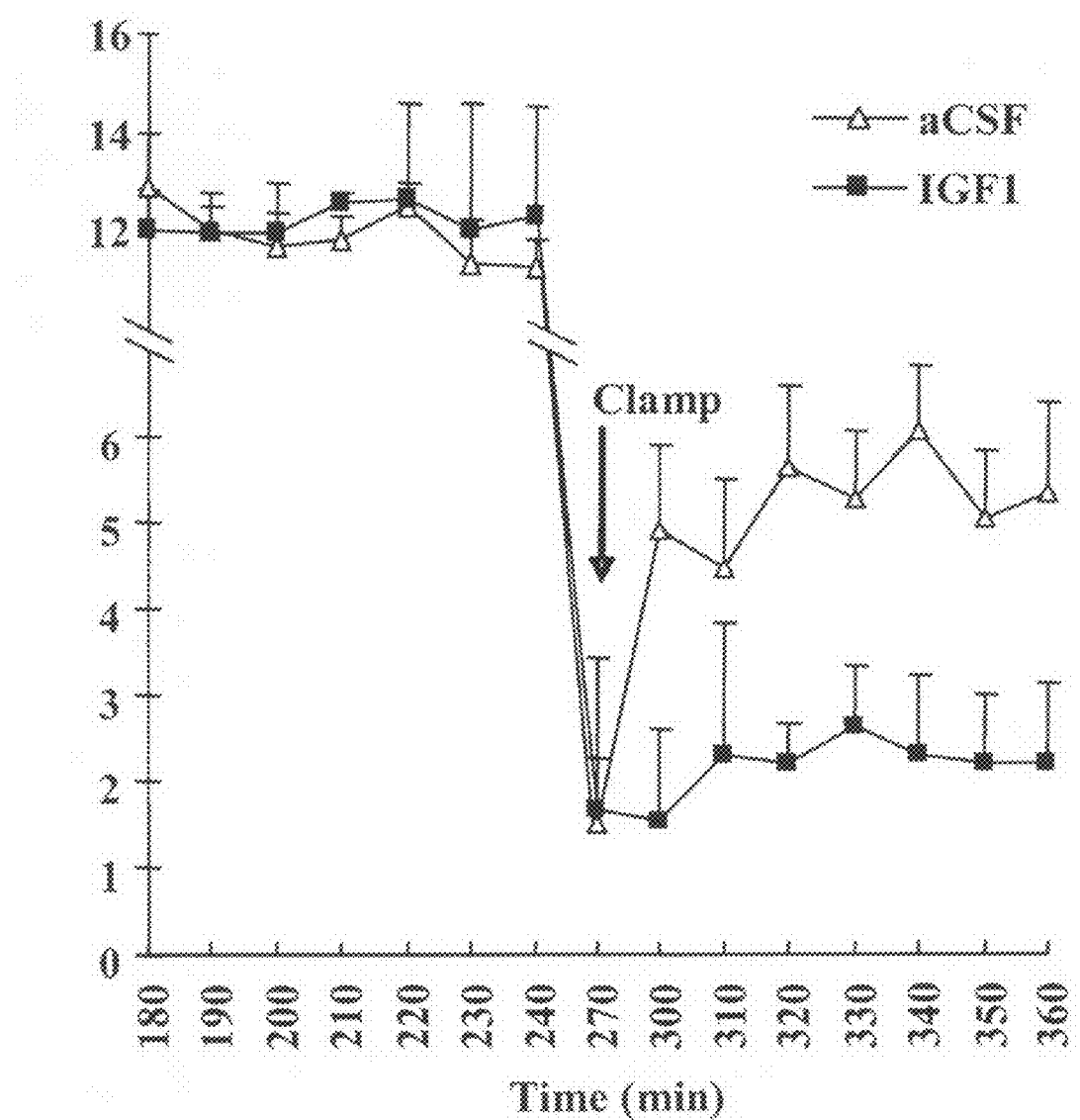

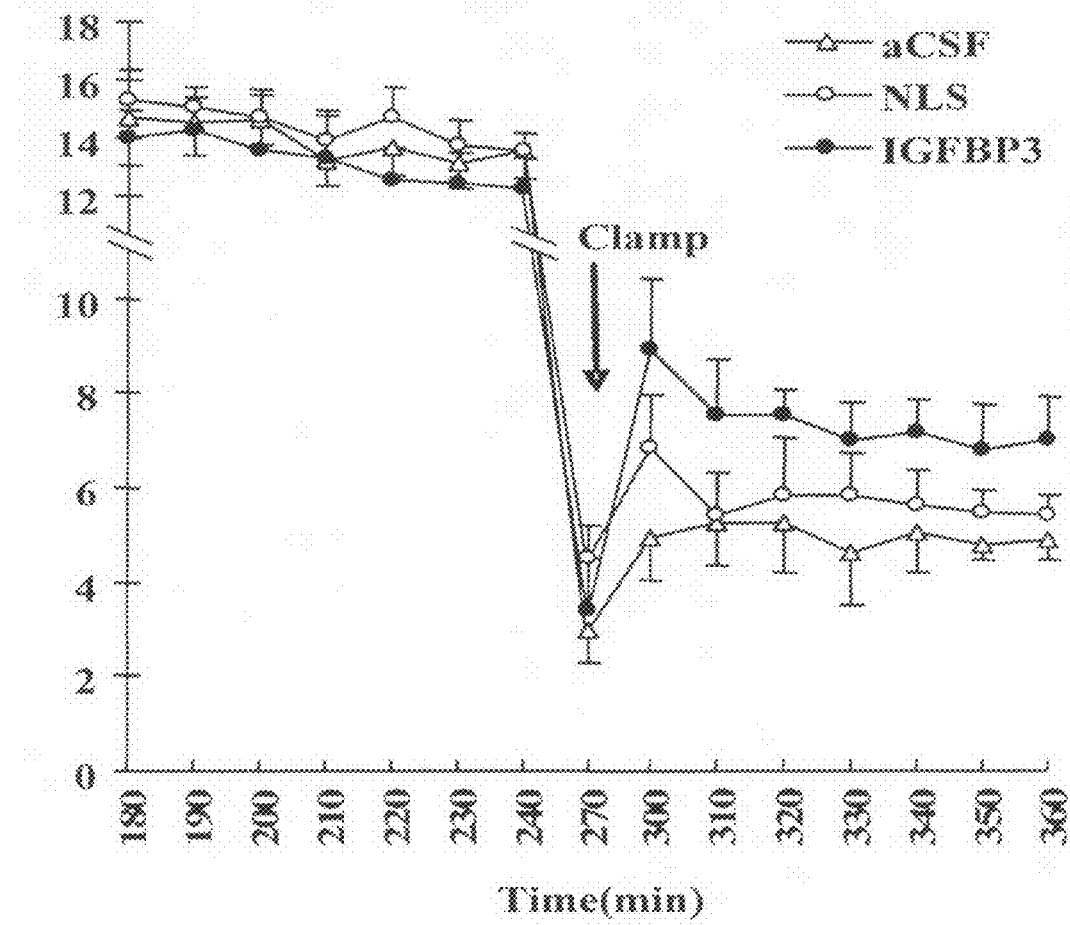

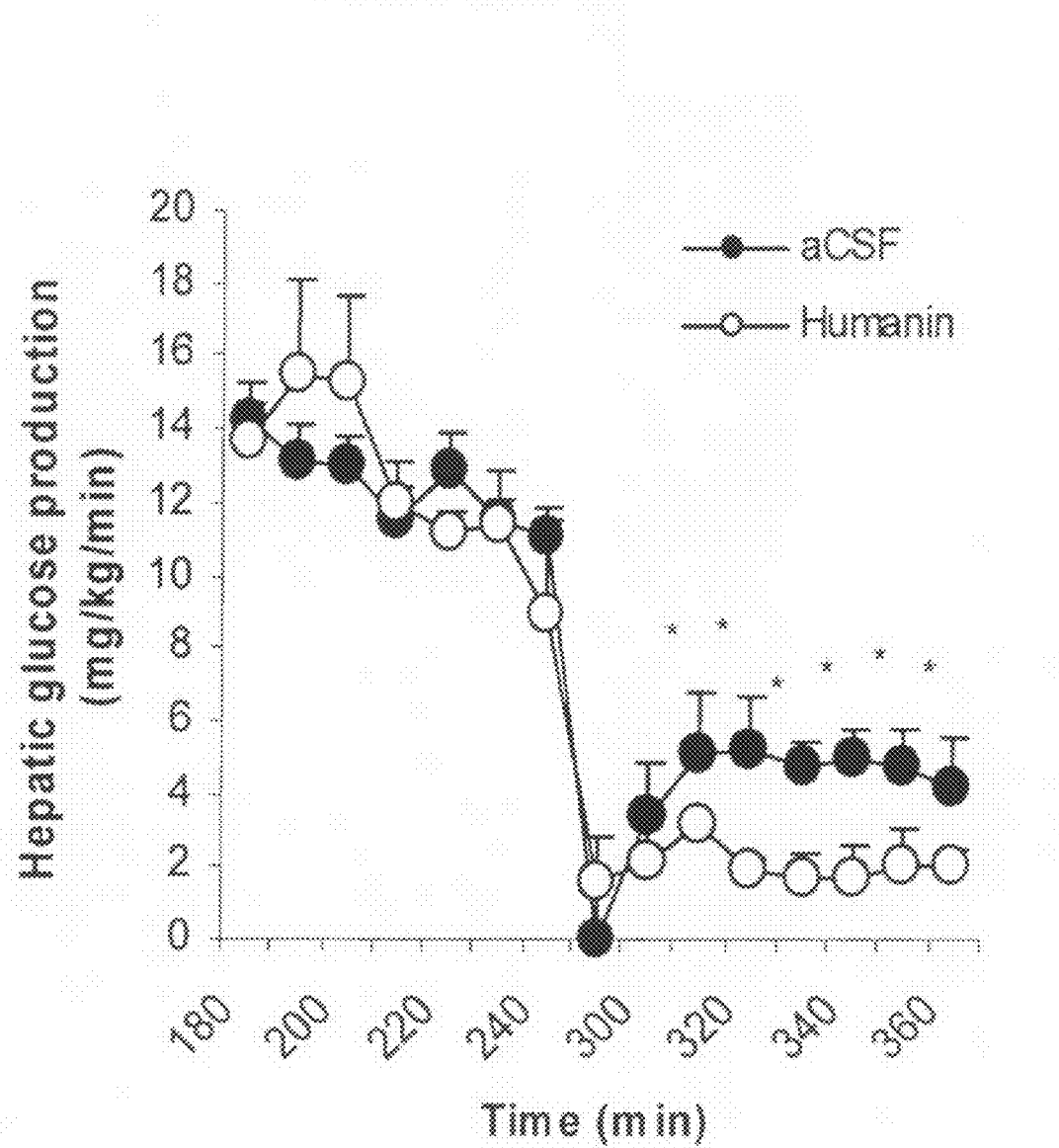

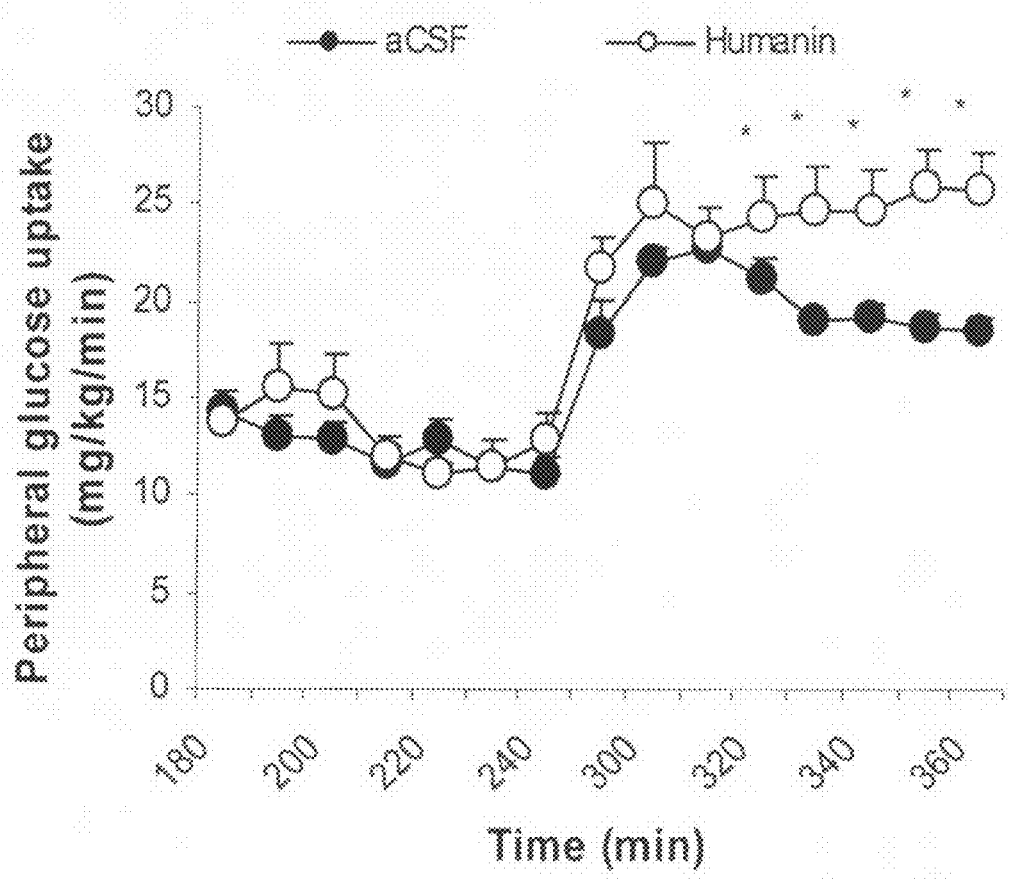

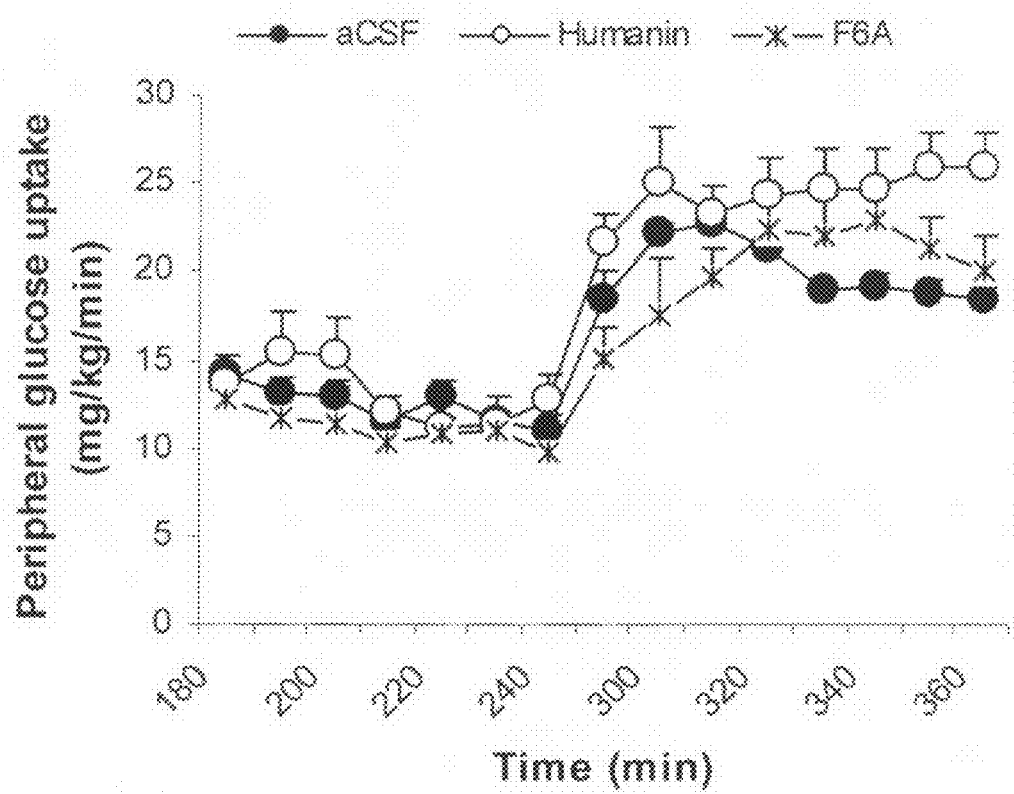

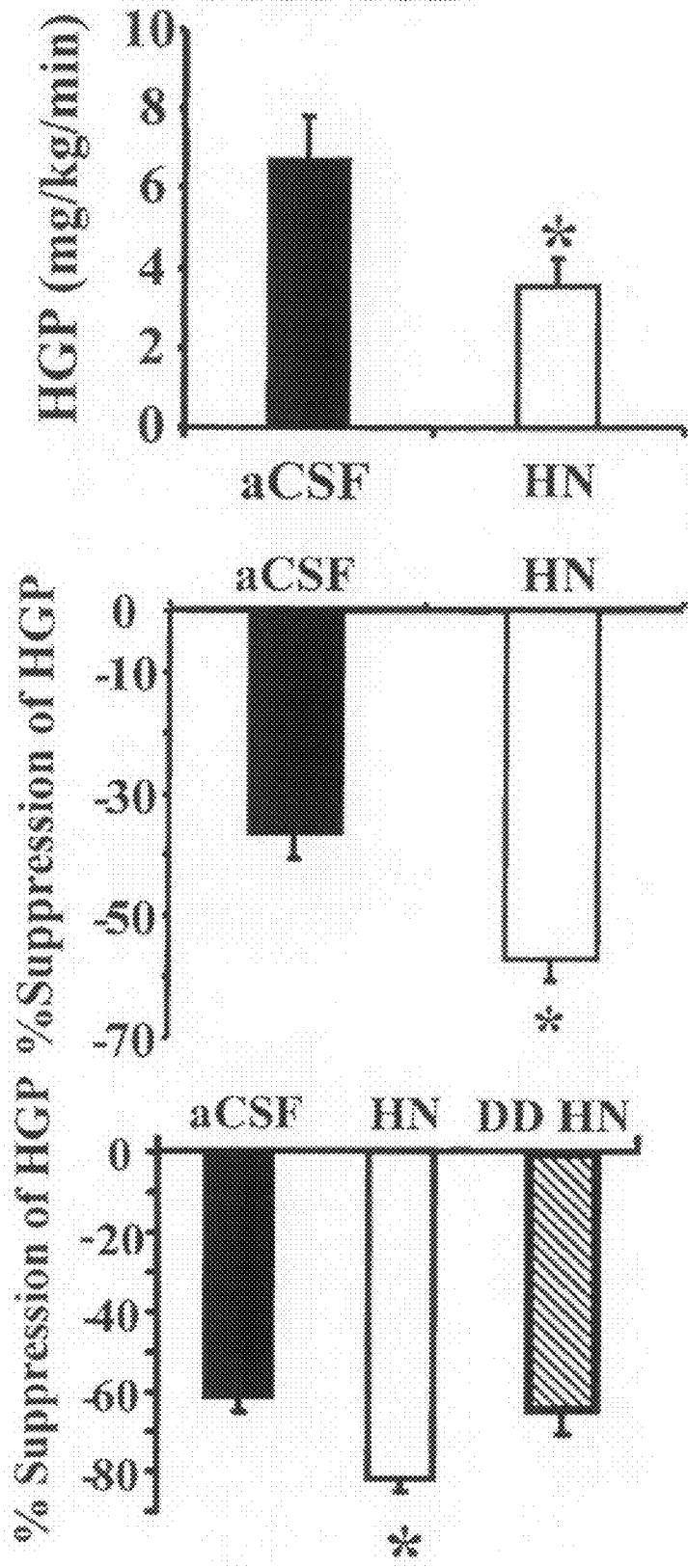

FIG. 17D-17G
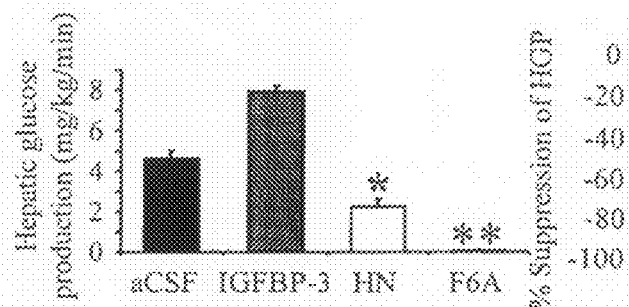
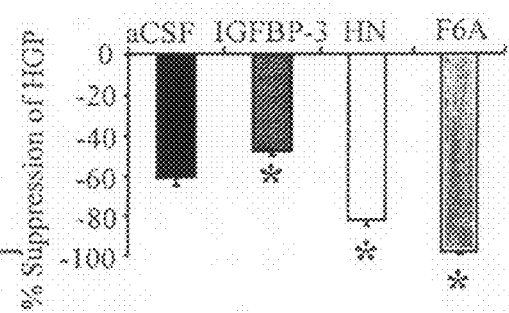
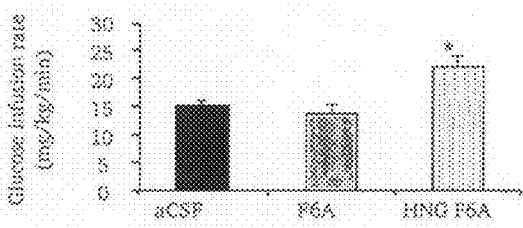
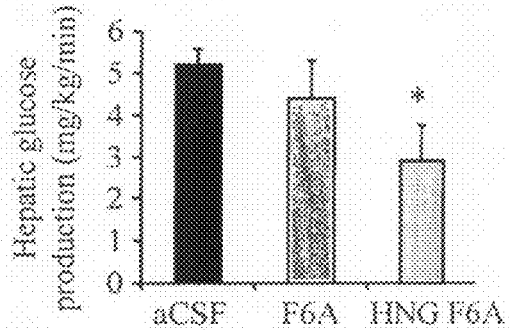
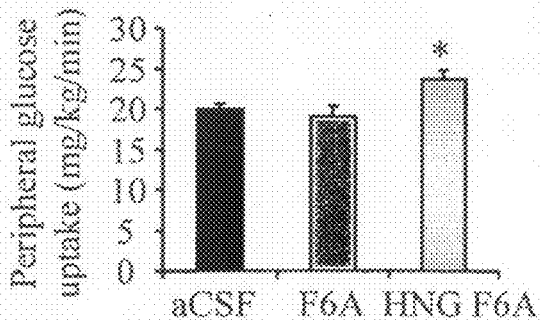

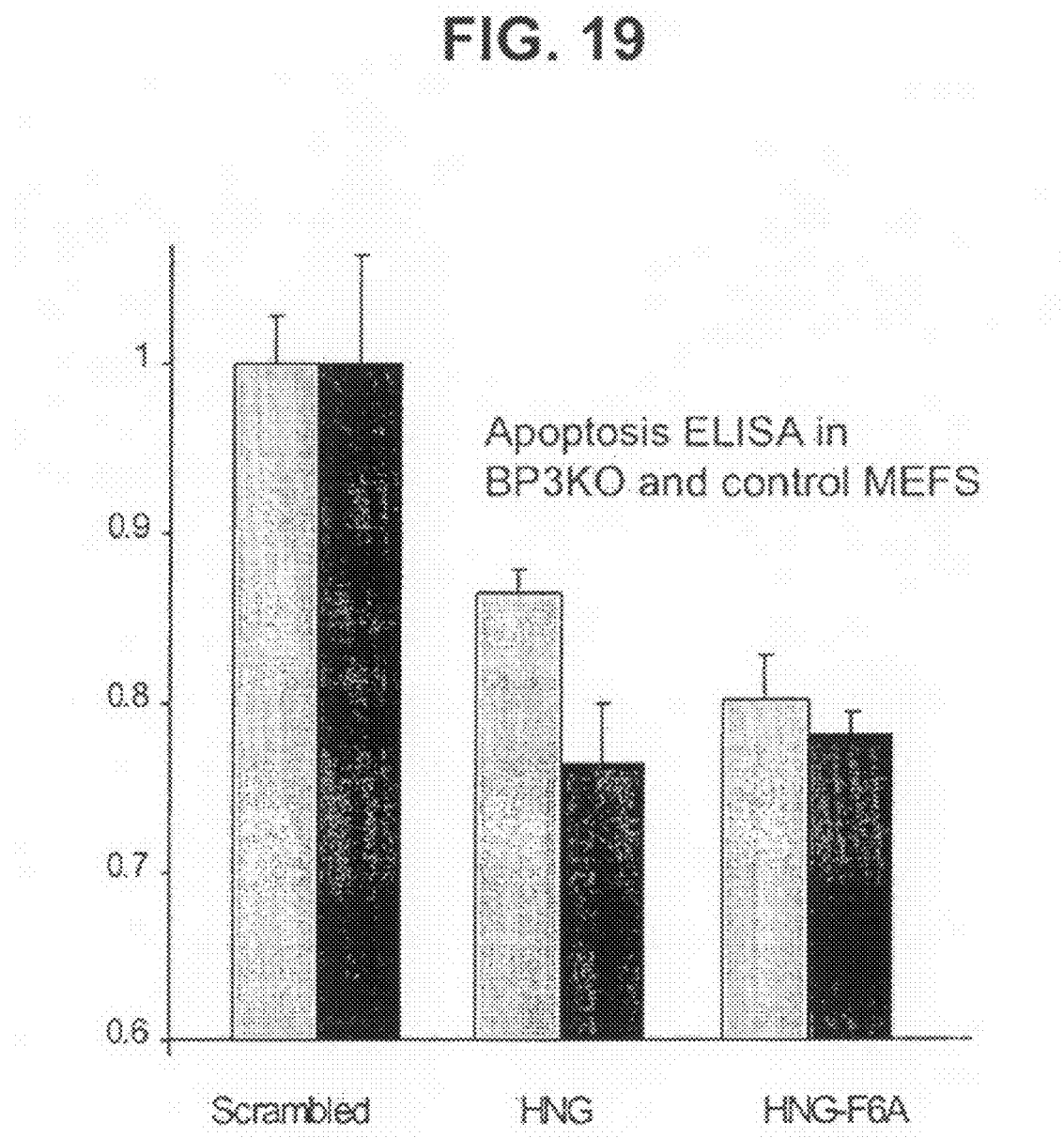

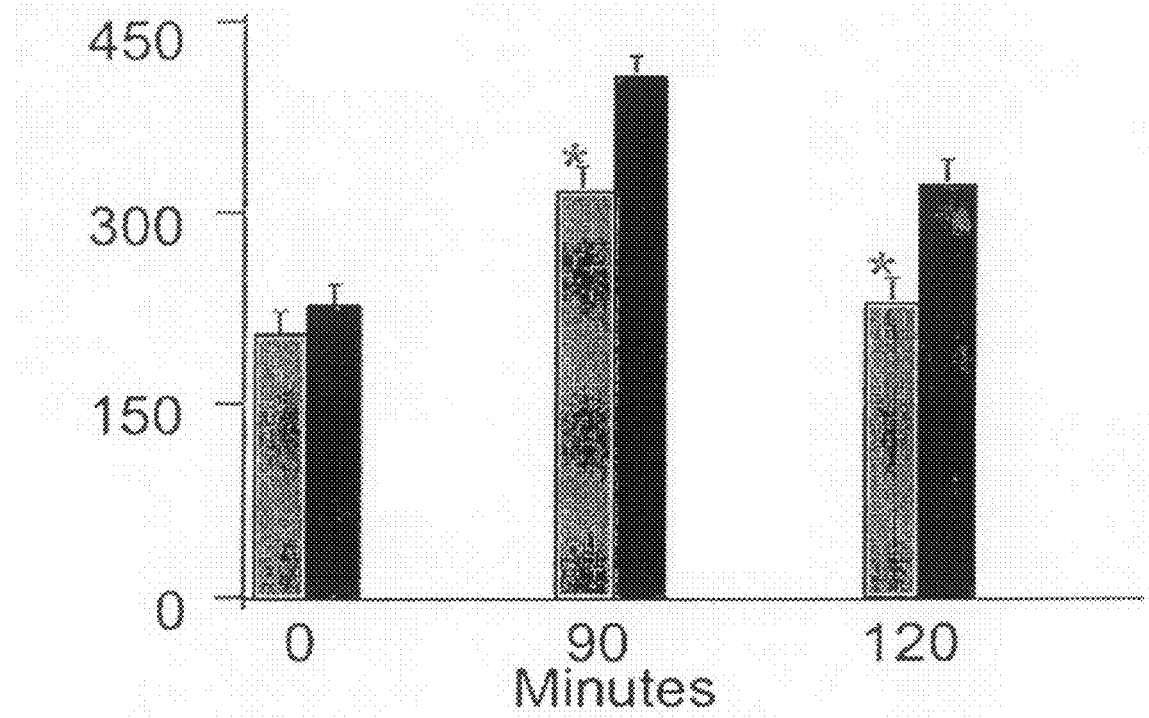

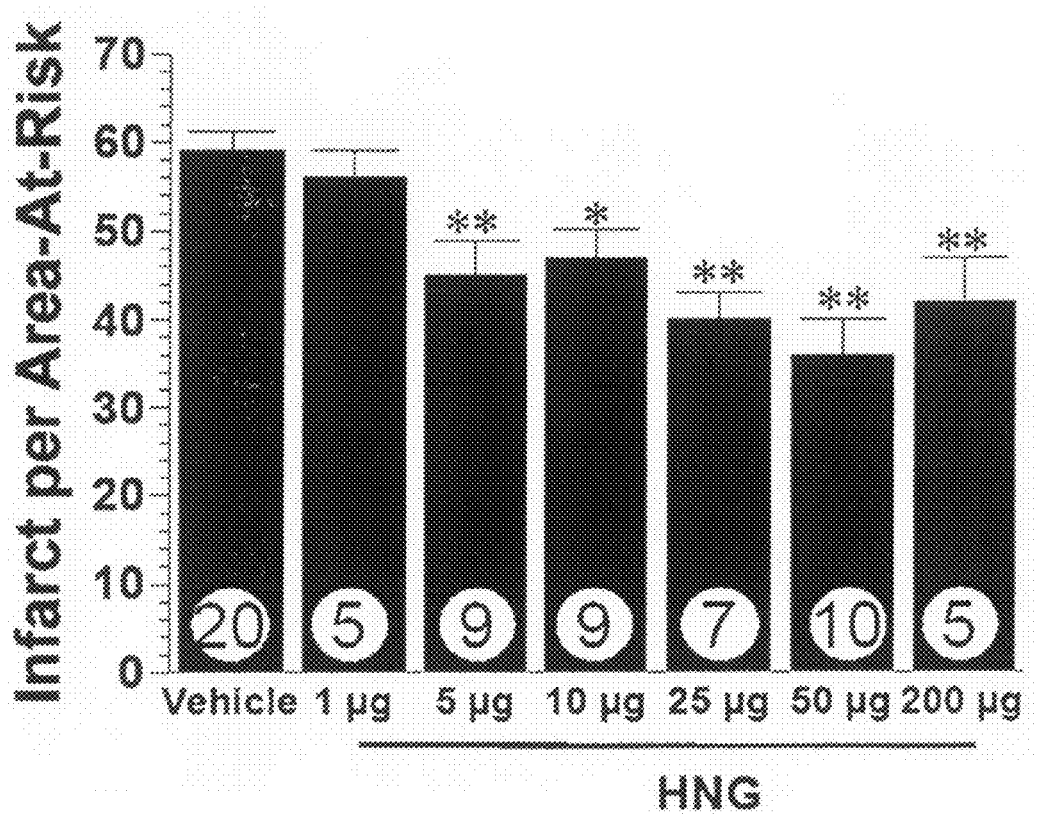

TREATMENT OF TYPE 2 DIABETES, METABOLIC SYNDROME, MYOCARDIAL INJURY AND NEURODEGENERATION WITH HUMANIN AND ANALOGS THEREOF

CROSS-REFERENCE TO RELATED APPLICATIONS

This application is a U.S. national stage entry under 35 U.S.C. §371 of PCT International Patent Application Ser. No. PCT/US2008/006720, filed May 28, 2008, and claims priority to U.S. Provisional Patent Application No. 60/932,254, filed May 30, 2007, and U.S. Provisional Application No. 61/010,695, filed Jan. 10, 2008, the contents of which are hereby incorporated by reference in their entireties into the subject application.

STATEMENT OF GOVERNMENT SUPPORT

This invention was made with government support under Grant Nos. CA100938, HD047013, AG018381, AG021654, and DK063491 awarded by the National Institutes of Health. The government has certain rights in the invention.

FIELD OF THE INVENTION

The present invention generally relates to treatment of type 2 diabetes, metabolic syndrome and neurodegeneration, such as occurs in Alzheimer's disease and amyotrophic lateral sclerosis, using humanin and humanin analogs. Humanin and humanin analogs can act by increasing insulin sensitivity. The invention also relates to treatment and prevention of myocardial injury and methods for determining longevity.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Decline in insulin action is a metabolic feature of aging and may be involved in the development of age related diseases including Type 2 Diabetes Mellitus (DM2) and Alzheimer's disease (AD) (Craft, 2005). Insulin-like growth factor-1 (IGF-1) is a key mediator of somatic growth and plays an important role in cell proliferation, survival and differentiation throughout life. In addition to effects on growth and development, IGF-1 plays a role in regulation of glucose metabolism. Administration of IGF-1 increases glucose uptake and inhibits hepatic glucose production in normal subjects, in insulin resistance states and in both type 1 and type 2 diabetes (Sherwin et al., 1994; Carroll et al., 2000; Simpson et al., 2004); this effect can be replicated in isolated rat muscle cells in vitro (Maher et al., 1989; Bilan et al., 1992), but not on hepatocytes with physiological IGF-1 levels (Binoux, 1995). Epidemiological studies have shown that individuals with low serum IGF-1 have a two-fold increased risk of developing glucose intolerance or DM2 (Sandhu et al., 2002). The effects of IGF-1 on insulin sensitivity are, in part, related to its ability to suppress growth hormone (GH), which has an insulin antagonistic effect; however, IGF-1 further improved insulin sensitivity when given in addition to a GH antagonist (pegvisomant), suggesting an independent enhancing effect of IGF on insulin sensitivity (O'Connell and Clemmons, 2002). Though several studies have shown an effect of IGF-1 on hepatic insulin action, the paucity of IGF-1 receptors in the hepatocytes (Frick et al., 2000) raises the question regarding how these effects are mediated.

Humanin (HN) is a recently identified peptide with a role in neuro-protection against Alzheimer's disease (AD) associated insults (Hashimoto et al., 2001). In fact, humanin was first identified from cDNA library of surviving neurons from an AD patient. Since then, its protective role has been described not only from various AD related insults, but also against prion-induced (Sponne et al., 2004) and chemical-induced damage (Mamiya and Ukai, 2001), thus broadening its role as a neuroprotective factor. Subsequently it has been shown to be protective against many other cytotoxic agents (Kariya et al., 2003) and also protect non-neuronal cells such as smooth muscle cells (Jung and Van Nostrand, 2003), rat pheochromocytoma cells (Kariya et al., 2002) and lymphocytes (Kariya et al., 2003).

Structurally, HN is a 24 amino acid polypeptide that is transcribed from an open reading frame within the mitochondrial 16S ribosomal RNA in mammals (Hashimoto et al., 2001). HN is both an intracellular and secreted protein. It has been detected in normal mouse testis and colon (by immunoblot and immunohistochemical analyses using specific antibodies against HN peptide) (Tajima et al., 2002) and is present in cerebrospinal fluid (CSF), seminal fluid and serum; levels in CSF are few orders of magnitude higher than that in circulation (P. Cohen, unpublished data). So far, little has been discovered about the regulation of its production. HN promotes cell survival by binding to a variety of pro-apoptotic protein partners, such as Bax-related proteins (Guo et al., 2003), putative cell-surface receptors (Ying et al., 2004), and IGF binding protein-3 (IGFBP-3) (Ikonen et al., 2003). IGFBP-3 is one of a number of peptides including insulin, leptin, adiponectin, and resistin that have been shown to act in the central nervous system to regulate glucose metabolism (Muse et al., 2007, Obici et al., 2002). Unlike these aforementioned peptides IGFBP-3 is an HN partner that has pro-diabetogenic hypothalamic actions that are modulated by IGF-1 (Muzumdar et al., 2006). cDNAs identical or similar to HN have since been identified in plants, nematodes, rats, mice and many other species demonstrating that it is highly conserved along evolution (Guo et al., 2003).

SUMMARY OF THE INVENTION

The inventors have discovered that treatment with humanin or humanin analogs increases insulin sensitivity in mammals.

The invention is directed to methods of treating a mammal exhibiting or at risk for insulin resistance. The methods comprise administering to the mammal a humanin or humanin analog.

The invention is also directed to methods of treating a mammal exhibiting or at risk for insulin resistance. The methods comprise administering to the mammal a compound that inhibits or reduces IGFBP-3.

Additionally, the invention is directed to methods of increasing insulin sensitivity in a mammal exhibiting or at risk for insulin resistance. The methods comprise administering to the mammal a humanin or humanin analog sufficient to increase insulin sensitivity in the mammal.

The invention is further directed to methods of increasing insulin sensitivity in a mammal exhibiting or at risk for insulin resistance. The methods comprise administering to the mammal a compound that inhibits or reduces IGFBP-3 in a manner sufficient to increase insulin sensitivity in the mammal.

The invention provides a method of treating type-2 diabetes mellitus in a subject comprising administering to the subject humanin or a humanin analog.

The invention provides a method of treating a metabolic syndrome in a subject comprising administering to the subject humanin or a humanin analog.

The invention provides a method of treating neurodegeneration in a subject comprising administering to the subject humanin or a humanin analog.

The invention provides methods of treating and preventing myocardial injury in a subject comprising administering to the subject humanin or a humanin analog.

The invention provides a method of determining a subject's likelihood of longevity, the method comprising comparing the level of humanin in the subject's plasma with the level of humanin in a control population, wherein a humanin level in the subject that is at least 100 pg humanin/mL of plasma greater than the humanin level in the control population indicates that the subject has an increased likelihood of longevity compared to the control population. The invention also provide a method of increasing a subject's likelihood of longevity which comprises increasing the level of humanin in the subject.

The invention also provides a humanin analog HNGF6A having the amino acid sequence MAPRGASCLLLLT-GEIDLPVKRRA (SEQ ID NO:18) and a humanin analog HNGF6AK21A having the amino acid sequence MAPR-GASCLLLLTGEIDLPVARRA (SEQ ID NO:20). Also provided is a purified and isolated (Zebrafish) humanin having the amino acid sequence MAKRGLNCLPHQVSEIDLS-VQKRI (SEQ ID NO:19).

BRIEF DESCRIPTION OF THE DRAWINGS

FIG. 2 is a photograph of gels showing depression of IGF-1, IGF-1 R and IGFBP-3 in the rat mediobasal hypothalamus. IGF-1, IGF-1 R and IGFBP-3 were demonstrated in the mediobasal wedge of the hypothalamus by RT-PCR.

FIG. 3A-3C. Graphs of experimental results showing the effect of ICV infusion of IGF-1 (Panel A) or IGFBP-3 (Panel B) on hepatic insulin action and hepatic partitioning of glucose fluxes (Panel C). In Panel A, young rats were subjected to 6 hr of ICV infusion of aCSF (control, open triangles) or 1 μg of IGF-1 (0.3 μg bolus followed by 0.7 μg over 6 hours, shaded squares). The rats were subjected to hyperinsulinemic clamp (3 mU/Kg/min) over the last 2 hours. There were no differences in the basal hepatic glucose production. ICV IGF-1 significantly increased the sensitivity of the liver to insulin (p<0.05). In Panel B, young rats were subjected to 6 hr of ICV infusion of aCSF (control, open triangles) or 5 ug of IGFBP-3 (shaded circle) or NLS-IGFBP-3 mutant (open circle) (1.25 ug bolus followed by 4 ug over 6 hours). The rats were subjected to hyperinsulinemic clamp (3mU/Kg/min) over the last 2 hours. There were no differences in the basal hepatic glucose production. ICV IGFBP-3 significantly impaired the sensitivity of liver to insulin and resulted in increased hepatic glucose production (p<0.01). IGFBP-3 NLS mutant did not change hepatic insulin sensitivity significantly. The graph in Panel C represents the changes in glycogenolysis under hyperinsulinemic clamp in the presence of an ICV infusion. ICV IGF-1 significantly suppressed glycogenolysis while IGFBP-3 significantly increased it. NLS mutant of IGFBP-3 did not change hepatic glucose partitioning compared to controls.

FIG. 8A-8B. Graphs showing the effect of ICV infusion of HN on hepatic and peripheral insulin action. Young rats were subjected to 6 hr of ICV infusion of aCSF (control, shaded circles) or 18 µg of HN (6 µg bolus followed by 12 µg over 6 hours, open circles). The rats were subjected to hyperinsulinemic clamp (3 mU/Kg/min) over the last 2 hours. ICV HN significantly increased the sensitivity of the liver to insulin ($p<0.001$) (Panel A) and significantly increased peripheral glucose uptake ($p<0.001$) (Panel B). Concomitant with the increase in Rd with ICV HN, both glycolysis and glycogen synthesis were significantly increased (Table 6).

FIG. 9A-9B. Graphs showing the effect of ICV infusion of the F6A HN analog on hepatic and peripheral insulin action. Young rats were subjected to 6 hr of ICV infusion of aCSF (control, shaded circles) or 18 µg of F6A HN (6 µg bolus followed by 12 µg over 6 hours, asterisks). The rats were subjected to hyperinsulinemic clamp (3 mU/Kg/min) over the last 2 hours. ICV F6A HN significantly increased the sensitivity of the liver to insulin ($p<0.001$) (Panel A) and tended to increase peripheral glucose uptake (Panel B).

FIG. 15A-15F. Humanin increases hepatic insulin sensitivity. A) Schematic representation of the experimental design for the ICV studies: The upper panel demonstrates the time line for the surgical procedures. The lower panel demonstrates the protocol on the day of the clamp. B) Hepatic glucose production (HGP) and degree of suppression of HGP by artificial cerebrospinal fluid (aCSF) and 0.1 µg/kg/min humanin (HN) infusions (n=5 each) during a basal pancreatic clamp. C) Glucose infusion rates during a basal pancreatic clamp and ICV infusion of aCSF, HN and a dimerization-deficient (DD) HN mutant. D) HGP and degree of HGP suppression during a hyperinsulinemic clamp (n=7 each). E) Effects of intravenous HN and Colivelin (n=5 each) on HGP during a hyperinsulinemic clamp. F) Effect of HN on Glucose production from primary isolated hepatocytes treated with (+), or without (−) insulin. *$p<0.05$ vs. controls.

FIG. 17A-17G. IGFBP-3 modulates the effects of HN on insulin sensitivity: A) IGFBP-3 binding of HN and HN analogues measured by densitometry of dot blots probed with radiolabeled IGFBP-3. B) Expression of HN and IGFBP-3 in mediobasal hypothalamus (MBH). Effects of ICV IGFBP-3, HN, F6AHN during a hyperinsulinemic clamp (n=6 each); on C) glucose infusion rate (GIR), D) HGP and degree of suppression of HGP. Effect of intravenous aCSF, F6A, and HNGF6A (n=6 each) on E) GIR, F) HGP, and G) glucose uptake. *$p<0.05$ vs controls.

FIG. 19. Loss of IGFBP-3 binding in F6AHNG increases potency of humanin. Apoptosis ELISA in BP3KO and control MEFS. For each pair of columns: left column=Wild type, right column=BP3KO.

FIG. 20. Humanin analog HNGF6A treats diabetes, as tested using NONcNZO10/LtJ Mice, a model for obesity-induced type 2 diabetes. Vertical Axis: Plasma Glucose (mg/dL). For each pair of columns: left column=14 day HNGF6A, right column=14 day saline.

FIG. 22. Humanin analogue HNG offers cardio-protection against ischemia-reperfusion injury. Mice were subjected to transient myocardial ischemia for a period of 45 min followed by reperfusion. HNG (1, 5, 10, 25, 50 and 200 μg) or vehicle (saline) was administered intraperitoneally one hour before ischemia.

DETAILED DESCRIPTION OF THE INVENTION

Figure 1:
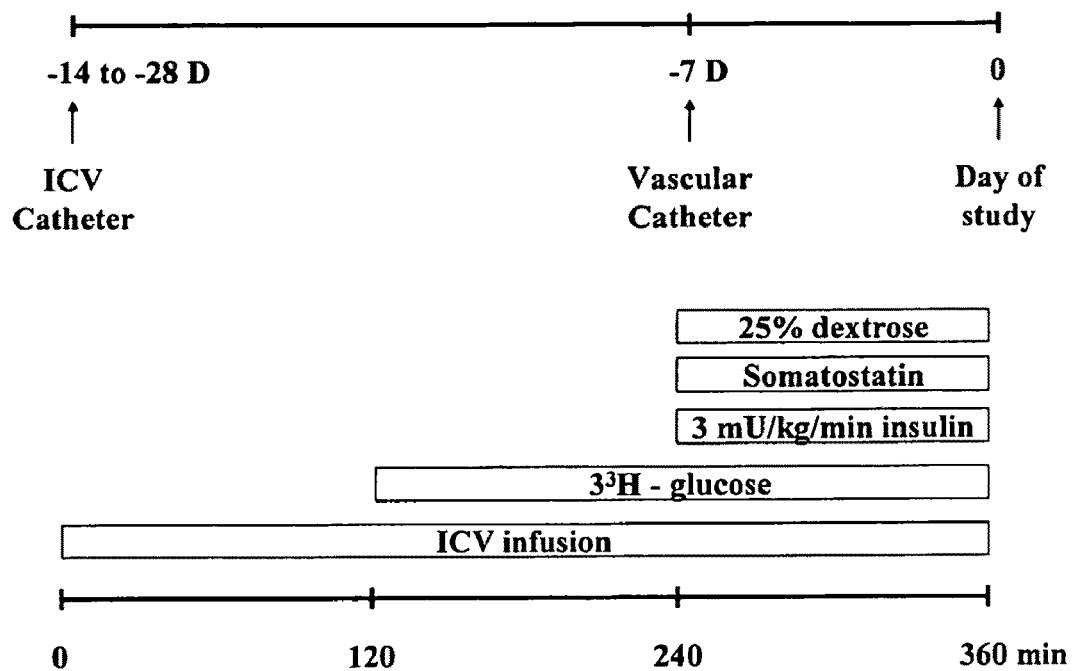
FIG. 1 is a schematic representation of the experimental design for the ICV studies. The upper panel demonstrates the time line for the surgical procedures. Surgical implantation of ICV catheters was performed 2-4 weeks before the clamp study and intravascular catheters were implanted in the week before the clamp. The lower panel demonstrates the protocol on the day of the clamp. ICV IGF-1, IGFBP-3, mutant or artificial cerebrospinal fluid (aCSF) infusions were initiated at the beginning of the study (t=0) and continued throughout the clamp. Infusion of labeled glucose was began at t=120 and was continued through out the study. The infusions of somatostatin and insulin were initiated at t=240 and continued for the remaining 2 h. A 25% glucose solution was infused as needed during the last two hours to maintain plasma glucose concentration.

The inventors have discovered that treatment with humanin or humanin analogs increases insulin sensitivity in mammals. See Examples.

The invention is directed to methods of treating a mammal exhibiting or at risk for insulin resistance. The methods comprise administering to the mammal a humanin or humanin analog.

As used herein, humanin is the human peptide maprgfs-cllltseidlpvkrra (SEQ ID NO:1), or naturally-occurring vertebrate equivalents. Humanin and several humanin analogs inhibit neuronal cell death by binding to its specific membrane-bound receptor, triggering the Jak2/STAT2 prosurvival pathway (Matsuoka et al., 2006). Several analogs of humanin have been developed, some of them orders of magnitude more potent than humanin in neuroprotection (Matsuoka et al., 2006; Chiba et al., 2005). Examples include the analogs provided herein as SEQ ID NO:2, 3, 4, 5, 6, 7, 8, 9, 18, 19 and 20. The skilled artisan could determine without undue experimentation whether any particular peptide is a humanin analog by determining whether the peptide is capable of neuroprotection in established humanin assays, e.g., as described in Chiba et al. (2005). Although the humanin or humanin analog can comprise non-peptide moieties, e.g., a fluorescent marker, it preferably consists entirely of a linear string of amino acids. More preferably, the humanin or humanin analog consists of less than about 50 amino acids. Even more preferably, the humanin or humanin analog consists of 17-50 amino acids.

Still more preferably, the humanin or humanin analog comprises 17-50 amino acids comprising the amino acid sequence of SEQ ID NO:11. As used herein, an amino acid sequence providing the designation (x/y), as in SEQ ID NO:11, indicates that either amino acid x or amino acid y can be used at the indicated position. Thus, the amino acid sequence (p/r/a)(r/a/g)(g/a)(f/a)s indicates that the first amino acid can be a proline, alanine or glycine; the second amino acid can be arginine, alanine or glycine, the third amino acid can be glycine or alanine, the fourth amino acid can be phenylalanine or alanine, and the fifth amino acid must be serine.

SEQ ID NO:11 is a deduced sequence providing alternative residues for the 17-mer amino acid sequence that provides humanin activity. The 17-mer provided in SEQ ID NO:11 corresponds to amino acids 3-19 of SEQ ID NO:11 (equivalent to HN17-SEQ ID NO:6), which has neuroprotective activity (Matsuoka et al., 2006), providing each alternative amino acid at each of the 17 positions that are in the humanin and humanin analogs SEQ ID NO:1, 2, 3, 4, 5, 6, 7, 8 and 9. Since each of the humanin and humanin analogs provided in SEQ ID NO:1, 2, 3, 4, 5, 6, 7, 8 and 9 have humanin activity, it is expected that any variant mixing amino acid residues from any of the identified humanin and analogs in each amino acid position would be expected to have humanin activity.

Even more preferably, the humanin or humanin analog comprises 17-26 amino acids comprising the amino acid sequence of SEQ ID NO:11.

Some preferred humanin analogs for the invention methods comprises the amino acid sequence of SEQ ID NO:10, which is the activity-dependent neurotrophic factor. When conjugated to a humanin or analog sequence, the resulting analog has increased activity (Chiba et al., 2005). Most preferably, the amino acid sequence of SEQ ID NO:10 is at the N-terminus of the humanin analog, as in colivelin (SEQ ID NO:9).

For these invention methods, the humanin or humanin analog most preferably consists of the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:18, SEQ ID NO:19 or SEQ ID NO:20.

In some embodiments, the humanin or humanin analog consists of the amino acid sequence of SEQ ID NO: 1. In other embodiments, the humanin or humanin analog consists of the amino acid sequence of SEQ ID NO:2. In additional embodiments, the humanin or humanin analog consists of the amino acid sequence of SEQ ID NO:3. In further embodiments, the humanin or humanin analog consists of the amino acid sequence of SEQ ID NO:4. Additionally, the humanin or humanin analog can consist of the amino acid sequence of SEQ ID NO:5. Further, the humanin or humanin analog can consist of the amino acid sequence of SEQ ID NO:6. In still other embodiments, the humanin or humanin analog consists of the amino acid sequence of SEQ ID NO:7. In still further embodiments, the humanin or humanin analog consists of the amino acid sequence of SEQ ID NO:8. In additional embodiments, the humanin or humanin analog consists of the amino acid sequence of SEQ ID NO:9, SEQ ID NO:18, SEQ ID NO:19 or SEQ ID NO:20.

The present methods can be used with any mammalian species. The mammal is preferably a human.

With these methods, the humanin or humanin analog can be administered directly to the mammal. Alternatively, the humanin or humanin analog is administered by administering a vector encoding the humanin to the mammal such that the humanin is expressed from the vector. Such vectors can be prepared for any given application without undue experimentation.

The humanin or humanin analog is preferably administered in a pharmaceutically acceptable carrier. By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The humanin or humanin analog can be formulated without undue experimentation for administration to a mammal, including humans, as appropriate for the particular application. Additionally, proper dosages of the compositions can be determined without undue experimentation using standard dose-response protocols.

Accordingly, the humanin or humanin analog compositions designed for oral, lingual, sublingual, nasal, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the humanin or humanin analog compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The humanin or humanin analog can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the humanin or humanin analog, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the humanin or humanin analog. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

Where the compound is administered peripherally such that it must cross the blood-brain barrier, the compound is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF). See Lee et al., Biopharm., April 1988 issue: 3037. The humanin or humanin analog can also be combined with micelles comprised of lipophilic substances. Such micelles can modify the permeability of the nasal membrane to enhance absorption of the compound. Suitable lipophilic micelles include without limitation gangliosides (e.g., GM-1 ganglioside), and phospholipids (e.g., phosphatidylserine). Bile salts and their derivatives and detergent-like substances can also be included in the micelle formulation. The compound can be combined with one or several types of micelles, and can further be contained within the micelles or associated with their surface.

The humanin or humanin analog used in the methods of the invention may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group.

In these methods, the humanin or humanin analog can be administered to the central nervous system (e.g., into the cerebrospinal fluid) of the mammal. When administered into the central nervous system, the humanin or humanin analog is preferably administered intracerebroventricularly to the mammal.

Alternatively, the humanin or humanin analog can be administered peripherally to the mammal. A preferred peripheral administration for these methods is parenteral administration. Most preferably, the humanin or humanin analog is administered intravenously to the mammal.

The inventors have also discovered that inhibiting or reducing IGFBP-3 increases insulin sensitivity. See Example 1. The invention is thus also directed to methods of treating a mammal exhibiting or at risk for insulin resistance. The methods comprise administering to the mammal a compound that inhibits or reduces IGFBP-3.

It is important to note that while inhibiting IGFBP-3 is beneficial in treating insulin resistance, and that humanin partially works through that mechanism, the enhanced action of F6A (Example 2) indicates that IGFBP-3 partially prevents humanin action on increasing insulin sensitivity and that F6A-HN is not inhibited by IGFBP-3 and is therefore more potent.

In some aspects of these methods, the compound reduces IGFBP-3 protein levels in the mammal. In other aspects, the compound inhibits IGFBP-3 activity in the mammal.

In these methods, the IGFBP-3 can be inhibited or reduced by administering to the mammal a nucleic acid comprising a region complementary to IGFBP-3 mRNA. Preferred examples of such nucleic acids include antisense molecules or RNAi molecules. Alternatively, the IGFBP-3 can be inhibited or reduced by administering to the mammal a compound that binds to IGFBP-3. Preferred examples of such compounds are aptamers or compounds that comprise antigen binding domain of an immunoglobulin that specifically binds to IGFBP-3 (e.g., a monoclonal antibody).

With any of the methods identified above, the mammal can be at risk for acquiring type-2 diabetes mellitus. Preferably, the mammal has type-2 diabetes mellitus. The mammal can also have hepatic steatosis. Additionally or alternatively, the mammal can have cardiovascular disease. In some embodiments, the mammal is elderly.

The invention is additionally directed to methods of increasing insulin sensitivity in a mammal exhibiting or at risk for insulin resistance. The methods comprise administering to the mammal a humanin or humanin analog sufficient to increase insulin sensitivity in the mammal.

As with the methods described above, in these methods the humanin or humanin analog preferably comprises 17-50 amino acids comprising the amino acid sequence of SEQ ID NO:11. More preferably, the humanin or humanin analog comprises 17-26 amino acids comprising the amino acid sequence of SEQ ID NO:11. The humanin or humanin analog can also be a humanin analog comprising the amino acid sequence of SEQ ID NO:10 at the N-terminus of the humanin analog. Most preferably, the humanin or humanin analog consists of the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:18, SEQ ID NO:19 and/or SEQ ID NO:20.

In some embodiments, the humanin or humanin analog consists of the amino acid sequence of SEQ ID NO:1. In other embodiments, the humanin or humanin analog consists of the amino acid sequence of SEQ ID NO:8. In additional embodiments, the humanin or humanin analog consists of the amino acid sequence of SEQ ID NO:9.

The present methods can be used with any mammalian species. The mammal is preferably a human.

With these methods, the humanin or humanin analog can be administered directly to the mammal. Alternatively, the humanin or humanin analog is administered by administering a vector encoding the humanin to the mammal such that the humanin is expressed from the vector. Such vectors can be prepared for any given application without undue experimentation.

In these methods, the humanin or humanin analog can be administered to the central nervous system (e.g., into the cerebrospinal fluid) of the mammal. When administered into the central nervous system, the humanin or humanin analog is preferably administered intracerebroventricularly to the mammal.

Alternatively, the humanin or humanin analog can be administered peripherally to the mammal. A preferred peripheral administration for these methods is parenteral administration. Most preferably, the humanin or humanin analog is administered intravenously to the mammal.

The invention is further directed to methods of increasing insulin sensitivity in a mammal exhibiting or at risk for insulin resistance. The methods comprise administering to the mammal a compound that inhibits or reduces IGFBP-3 in a manner sufficient to increase insulin sensitivity in the mammal.

In some aspects of these methods, the compound reduces IGFBP-3 protein levels in the mammal. In other aspects, the compound inhibits IGFBP-3 activity in the mammal.

In these methods, the IGFBP-3 can be inhibited or reduced by administering to the mammal a nucleic acid comprising a region complementary to IGFBP-3 mRNA. Preferred examples of such nucleic acids include antisense molecules or RNAi molecules. Alternatively, the IGFBP-3 can be inhibited or reduced by administering to the mammal a compound that binds to IGFBP-3. Preferred examples of such compounds are aptamers or compounds that comprise antigen binding domain of an immunoglobulin that specifically binds to IGFBP-3 (e.g., a monoclonal antibody).

With any of the methods identified above, the mammal can be at risk for acquiring type-2 diabetes mellitus. Preferably, the mammal has type-2 diabetes mellitus.

The invention provides methods of treating type-2 diabetes mellitus in a subject comprising administering to the subject one or more of humanin or one or more humanin analog.

The invention provides methods of treating a metabolic syndrome in a subject comprising administering to the subject one or more of humanin or one or more humanin analog. The metabolic syndrome may be associated with diabetes. A subject is defined as having a "metabolic syndrome" according to the guidelines of the National Cholesterol Education Program (NCEP), Adult Treatment Panel III (ATP III) (Executive Summary . . . *JAMA* 2001; 285:2486-97), if the subject has three or more of the following five risk factors: 1) increased waist girth (>94 cm for women, >102 cm for men), 2) increased blood pressure (>130//85 or treatment for hypertension), 3) increased fasting glucose (>110 mg/dl or drug treatment for diabetes), 4) low plasma HDL cholesterol (<40 mg/dl), and 5) elevated fasting triglyceride levels (>150 mg/dl). In one embodiment of the methods described herein, the subject is defined as having a metabolic syndrome if the subject has three or more of the following four risk factors: 1) increased waist girth (>94 cm for women, >102 cm for men), 2) increased blood pressure (>130//85 or treatment for hypertension), 3) increased fasting glucose (>110 mg/dl or drug treatment for diabetes), and 4) elevated fasting triglyceride levels (>150 mg/dl).

The invention provides methods of treating neurodegeneration in a subject comprising administering to the subject one or more of humanin or one or more humanin analog. The subject may have, for example, Alzheimer's disease or amyotrophic lateral sclerosis.

The invention provides methods of treating or preventing myocardial injury in a subject comprising administering to the subject one or more of humanin or one or more humanin analog. In one embodiment, the method provides cardioprotection against ischemia-reperfusion injury. In one embodiment, the method treats acute myocardial infarction.

The invention provides a method of determining a subject's likelihood of longevity, the method comprising comparing the level of humanin in the subject's plasma with the level of humanin in a control population, wherein a humanin level in the subject that is at least 100 pg humanin/mL of plasma greater than the humanin level in the control population indicates that the subject has an increased likelihood of longevity compared to the control population. Preferably, the humanin level in the subject is at least 200 pg humanin/mL of plasma greater than the humanin level in the control population. More preferably, the humanin level in the subject is at least 300 pg humanin/mL of plasma greater than the humanin level in the control population.

The invention also provides a method of increasing a subject's likelihood of longevity which comprises increasing the level of humanin in the subject. In one embodiment, the subject is administered one or more of humanin or one or more humanin analog.

The invention also provides a humanin analog HNGF6A having the amino acid sequence MAPRGASCLLLLT-GEIDLPVARRA (SEQ ID NO:18) and a humanin analog HNGF6AK21A having the amino acid sequence MAPR-GASCLLLLTGEIDLPVARRA (SEQ ID NO:20). Also provided is a purified and isolated (Zebrafish) humanin having the amino acid sequence MAKRGLNCLPHQVSEIDLS-VQKRI (SEQ ID NO:19).

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Central and Opposing Effects of IGF-1 and IGFBP-3 on Systemic Insulin Action

This Example is substantially published as Muzumdar et al., 2006.

Example Summary

IGF-1 is recognized as an insulin sensitizer at the liver and muscle, while emerging evidence suggests that IGF binding protein-3 (IGFBP-3) acts as an insulin antagonist. As there is a paucity of IGF-1 receptors in the liver and the IGF-IGFBP system in the CNS is emerging as physiologically relevant, the effects of IGF-1 and IGFBP-3 on insulin action were evaluated to determine whether they are mediated through central mechanisms. Infusion of IGF-1 ICV during insulin clamp (3mU/kg/min) resulted in significant improvement in hepatic insulin action (50%, p<0.05). In contrast, infusion of IGFBP-3 ICV significantly impaired insulin action at the liver (45% increase in hepatic glucose production, p<0.01). While IGF-1 marginally increased peripheral glucose uptake, IGFBP-3 significantly decreased peripheral glucose uptake (−30%, p<0.01). As the NLS-mutant IGFBP-3, which has a normal affinity to IGFs but binds other IGFBP-3 partners poorly and fails to normally internalize, has reduced central activity on metabolism, it was concluded that IGFBP-3 effects on the hypothalamus involves activity mediated by interfacing with additional molecules in addition to IGFs. Marked, opposing and independent physiological effects of IGF-1 and IGFBP-3 through central mechanisms may have implications on potential strategies in specific modulation of peripheral insulin action.

Introduction

Recently, novel metabolic effects of CNS insulin and leptin through the hypothalamus have been demonstrated, leading to alterations in both hepatic and peripheral glucose metabolism (Obici et al., 2002). Because of the relative abundance of IGF-1 receptors in the hypothalamus, especially in the arcuate and mediobasal hypothalamus (Garcia-Segura et al., 1997; Fernandez-Galaz et al., 1999), it was evaluated whether the effects of IGF-1 on HGP are mediated through central IGF-1 receptors.

IGF binding protein-3 (IGFBP-3), the major binding protein for IGF-1 has recently been demonstrated to play a role in glucose metabolism. A relationship between elevated circulating IGFBP-3 levels and hyperglycemia is suggested in various physiological and pathological states associated with insulin resistance such as puberty (Lofqvist et al., 2005), acromegaly (Wass et al., 1982) and treatment with recombinant human growth hormone (Cutfield et al., 2000). Transgenic mice over expressing IGFBP-3 demonstrate impaired glucose tolerance and decreased glucose uptake in both liver and muscle (Silha et al., 2002). Effects of IGFBP-3 on glucose metabolism could be secondary to decreased availability of IGF-1. However, evidence is accumulating that IGFBP-3 can directly, independent of IGF-1 binding, affect glucose metabolism and insulin action. A direct, non IGF-1 dependent biological role has been conclusively demonstrated in many tumor cell lines in vitro, with IGFBP-3 showing effects on cellular proliferation and apoptosis (Rajah et al., 1997) through a yet unidentified receptor (Huang et al., 2003). IGFBP-3 directly inhibits insulin action (Chan et al., 2005), activate tyrosine phosphatases (Ricort and Binoux, 2002) and bind RXR in the nucleus after cellular internalization (Liu et al., 2000).

IGFBP-3 has been demonstrated in the brain in normal (Bunn et al., 2005; Ocrant et al., 1990) and pathological states like Alzheimer's disease (Rensink et al., 2002). To test if some of the physiological effects of IGF-1 and IGFBP3 are elicited through the brain, either IGF-1 or IGFBP-3 levels were acutely modulated in the CNS and their peripheral effects were carefully monitored on several actions of insulin. To identify if the effects of IGFBP-3 are IGF-1 independent, the mutant form of IGFBP-3 was used. This mutant lacks the nuclear localization signal (NLS). Though it binds IGF-1 normally, it does not bind other IGFBP-3 partners that are involved in intracellular localization and therefore loses its intracellular actions (Schedlich et al., 2000). IGFBP-3 was also infused peripherally and its effects on glucose metabolism studied under hyperinsulinemic clamp conditions.

Materials and Methods.

Animals. Young (3 mo old, n=6 in each group), male Sprague-Dawley rats (Charles River Laboratories, Wilmington, Mass.) were used for this study. Rats were housed in individual cages and were subjected to a standard light (6:00 AM to 6:00 PM)-dark (6:00 PM to 6:00 AM) cycle. All rats were fed ad libitum using regular rat chow that consisted of 64% carbohydrate, 30% protein, and 6% fat with a physiological fuel value of 3.3-kcal/g chow. In the rats that received ICV infusions, 2 to 4 weeks before the in vivo study, the rats were anesthetized by inhalation of isoflurane and a cannula was placed ICV in the third ventricle for infusions of IGF-1, IGFBP-3 or IGFBP-3 mutant or artificial cerebrospinal fluid (aCSF), as previously described (Muzumdar et al., 2003) (FIG. 1). Briefly, a 26-gauge stainless steel guide cannula (Plastics One, Roanoke, Va.) was chronically implanted into the third ventricles using the following coordinates from bregma: anterior-posterior; +0.2 mm dorsal-ventral; −9.0 mm medial-lateral; 0.0 directly on the mid-sagittal suture, followed by a 28-gauge dummy cannula, inserted to prevent clogging of the guide cannula. The implant was secured to the skull with Caulk Grip dental cement, and the skin was closed over the implant using wound clips. The recovery of rats from the surgical stress was monitored with daily weight, food intake, and movement.

Upon recovery of body weight, usually a week, indwelling catheters were placed in the right internal jugular vein and in the left carotid artery (Muzumdar et al., 2003). The venous catheter was extended to the level of the right atrium, and the arterial catheter was advanced to the level of the aortic arch. Recovery was continued until body weight was within 3% of the pre-operative weight (~4-6 days). In the rats that received peripheral IGFBP-3, only the vascular catheters were placed.

Basal and hyperinsulinemic clamp in ICV studies. See FIG. 1. Studies were performed in unrestrained rats using the insulin clamp technique, in combination with high performance liquid chromatography-purified [3-$^3$H]glucose and [U-$^{14}$C]lactate infusions, as described previously (Liu et al., 1998). Food was removed for ~0.5 h before the in vivo protocol. All studies lasted 360 min and included a 120-min equilibration period, a 120-min basal period for assessment of the basal glucose turnover, and a 120-min hyperinsulinemic clamp period. All rats received ICV infusions (bolus followed by continuous ICV infusions of IGF-1, IGFBP-3, IGFBP-3 mutant or aCSF, depending on the group) over the entire 6 hours of the study. At the beginning of the basal period and 120 min before starting the glucose/insulin infusions, a primed-continuous infusion of high performance liquid chromatography-purified [3-$^3$H]glucose (NEN Life Science Products, Boston, Mass.; 20 µCi of bolus, 0.2 µCi/min) was initiated and maintained throughout the remaining 4 h of the study. In the final 2 hours of the study, the rats were subjected to hyperinsulinemic clamp. The protocol followed during the insulin clamp study was similar to that previously described (Liu et al., 1998). Briefly, a primed-continuous infusion of regular insulin (3 milliunits/kg·min) was administered, and a variable infusion of a 25% glucose solution was started and periodically adjusted to clamp the plasma glucose concentration at 7-8 mM. To prevent endogenous insulin secretion and in order to control for possible effects of ICV infusions on the endocrine pancreas, somatostatin (1.5 µg/kg·min) was also infused in all the groups. [U-$^{14}$C]Lactate (5 µCi of bolus/0.25 µCi/min) was infused during the last 10 min of the study.

ICV IGF-1 study. A bolus of hIGF-1 (0.3 mcg, a gift from Tercica, South San Francisco) was followed by a continuous infusion over 6 hours (total dose of 1 mcg, 0.06 µg/kg/hr). No hIGF-1 was detected in the rat periphery confirming that there was no leak from ICV infusions. (Human IGF-1 does not cross react with rat's endogenous IGF-1 in specific ELISA assays).

ICV IGFBP-3/mutant study. A bolus of non glycosylated hIGFBP-3 (1.25 µg, generously provided by Celtrix, Mountain View Calif.) was followed by a continuous infusion over 6 hours (total dose of 5.25 mcg, 0.26 µg/kg/hr). No hIGFBP-3 was detected in the rat periphery confirming that there was no leak from ICV infusions. To further characterize the effects on glucose metabolism, non-glycosylated NLS mutant of IGFBP-3 (Celtrix, Mountain View Calif.) was infused. This NLS mutant has two amino acid substitutions (K228E and R230G) and has been characterized (Lee et al., 2004).

Peripheral IGFBP-3 study. To study the acute effects of an infusion of IGFBP-3, two groups of awake, unstressed, chronically catheterized Sprague-Dawley rats (~300 g) were studied for 300 mM (n=6 in each group) under hyperinsulinemic clamp (as previously described). From 120 min the rats received a primed continuous infusion of IGFBP-3 (0.06 mg/kg/hr) or saline (control) for an additional 3 h.

Plasma samples for determination of [$^3$H] glucose and [$^3$H] water specific activities were obtained at 10-min intervals during the basal and clamp periods. Steady state conditions for the plasma glucose concentration and specific activity were achieved within 90 min in all the studies. Plasma samples for determination of plasma IGF-1 (rat and human), IGFBP-3 (human IGFBP-3), GH, insulin, leptin, and FFA concentrations were collected at 30-min intervals throughout the study. All determinations were also performed on portal vein blood obtained at the end of the experiments. The total amount of blood drawn during the entire study for various assays is ~3 cc. After separation of plasma (subsequently used for analysis), the red blood cells were reconstituted in saline and infused back into the animal.

At the end of the clamp study, rats were sacrificed using 100 mg pentobarbital sodium/kg body wt IV. Epididymal, mesenteric, and perinephric fat pads (visceral fat) were dissected and weighed at the end of each experiment. The study protocol was reviewed and approved by the Animal Care and Use Committee of the Albert Einstein College of Medicine.

Assays and analytical procedures. Plasma glucose (sample volume 10 µl) was measured by the glucose oxidase method (Glucose Analyzer II, Beckman Instruments, Palo Alto, Calif.). Plasma [$^3$H] glucose radioactivity was measured in duplicates in the supernatants of Ba(OH)$_2$ and ZnSO$_4$ precipitates of plasma samples (20 µl) after evaporation to dryness to eliminate tritiated water. UDPG and PEP concentrations and specific activities in the liver were obtained through two sequential chromatographic separations, as previously reported (Liu et al., 1998). Plasma insulin (10 µl) was measured by RIA using rat insulin standard for basal studies and human insulin standard for insulin clamp studies. Plasma leptin (10 µl) was assayed using the Linco leptin assay kit (Linco Research, St. Charles, Mo.). Plasma non-esterified fatty acid concentrations (5 µl) were determined by an enzymatic method with an automated kit according to the manufacturer's specification (Waco Pure Chemical Industries, Osaka, Japan). Rat IGF-I (50 µl) was measured with a rIGF-1 ELISA kit (DSL, Webster, Tex.). Human IGF-1 (50 µl) was measured with an in-house kit developed in UCLA using a double monoclonal antibody ELISA with sensitivity of 0.1 ng/ml and an intra-assay and inter-assay coefficient of variations which are <6% and <8%, respectively, in the range from 1 to 6 ng/ml. Human IGFBP-3 (30 µl) was measured with an ELISA kit (DSL, Webster, Tex.). This kit reads both IGFBP-3 and NLS IGFBP-3. No human IGF-1, hIGFBP-3 or NLS-IGFBP-3 was identified in the rat periphery in the groups that received these peptides ICV, indicating that no leaks occurred during the infusions and that the effects observed in these studies are strictly central in nature. Serum levels of rat growth hormone were determined using an enzyme immunoassay (EIA) kit (ALPCO, Windham, N.H.) according to the manufacturer's instructions. The detection limit of this assay is 0.5 ng/ml and the intra-assay and inter-assay variations are <10% and <14%, respectively.

Calculations of whole body glucose fluxes. Under steady-state conditions for plasma glucose concentrations, the rate of glucose disappearance ($R_d$) equals the rate of glucose appearance ($R_a$). The latter was calculated as the ratio of the rate of infusion of [3-$^3$H] glucose (dpm/min) and the steady-state plasma [$^3$H] glucose specific activity (dpm/mg). The rate of endogenous glucose production was calculated as the difference between $R_a$ and the infusion rate of glucose. The rates of glycolysis were estimated as described previously (2Rossetti and Giaccari, 1990). Glycogen synthesis was estimated by subtracting the rate of glycolysis from the $R_d$.

Hepatic glucose fluxes. The direct contribution of plasma glucose to the hepatic G-6-P pool was calculated from the ratio of specific activities of hepatic [$^3$H] UDPG (uridine diphosphate glucose) and plasma glucose after [3-$^3$H] glucose infusion. This represents the percentage of the hepatic G-6-P pool that is derived from plasma glucose. The indirect contribution of plasma glucose to hepatic G-6-P was derived from the ratio of specific activities of hepatic [$^{14}$C] UDPG and [$^{14}$C] PEP (phosphoenolpyruvate)×2 after [$^{14}$C] lactate infusion. This represents the percentage of the hepatic G-6-P pool that is derived from PEP-gluconeogenesis. Total glucose output (TGO) is the sum of the HGP+glucose cycling ([$^3$H] UDPG SA/plasma [3-$^3$H] glucose SA x TGO; SA, specific activity). Therefore, TGO=HGP/(1-[$^3$H] UDPG SA/plasma [3-$^3$H] glucose SA). Glu coneogenesis was estimated from the specific activities of $^{14}$C-labeled hepatic UDPG (assumed to reflect the specific activity of hepatic G-6-P) and hepatic PEP after the infusion of [U-$^{14}$C]lactate and [3-$^3$H]glucose (Liu et al., 1998). Therefore, gluconeogenesis=TGO×[$^{14}$C] UDPG SA/[$^{14}$C] PEP SA×2. Glycogenolysis was calculated as the difference between HGP and gluconeogenesis.

Expression of IGF-1, IGF-1 receptor and IGFBP-3 in the rat mediobasal hypothalamus. Total RNA was extracted from the mediobasal wedge of rat hypothalamus following Clontech's protocol. First-stranded cDNA was synthesized from 1 µg of total RNA using Superscript III (Gibco, Gaithersburg, Md.). Expression of IGF-1, IGF-1 receptor and IGFBP-3 was demonstrated by RT-PCR. The sequences for IGF-1, sense: 5'-TCTGAGGAGGCTGGAGATGT-3' (SEQ ID NO:12) and antisense: 5'-GTTCCGATGTTTTGCAGGTT-3' (SEQ ID NO:13); for IGF-1 receptor, sense: 5'-GCGTCTTCAC-CACTCATTCC-3' (SEQ ID NO:14) and antisense: 5'-GCG-CATAAGTTCAAACAGCA-3' (SEQ ID NO:15); and for IGFBP-3, sense: 5'-GGCCCAGCAGAAATATCAAA-3' (SEQ ID NO:16) and antisense: 5'-TACCAGGGTCTCCAA-CAAGG-3' (SEQ ID NO:17) were used in the reaction. The conditions for PCR were 94° C. for 10 min, cycles of 94° C. for 30 sec, then annealing temperature of 60° C. for 30 sec and then 72° C. for 1.5 min. The product sizes were 240 bp, 179 by and 194 by for IGF-1, IGF-1 R and IGFBP-3 respectively.

Reverse Transcription and Amplification of Complementary DNA. Total RNA was extracted following Clontech's protocol. First-stranded cDNA was synthesized from 1 µg of total RNA using Superscript III (Gibco, Gaithersburg, Md.). Hepatic glucose-6-phosphatase (Glc-6-Pase) and phosphoenolpyruvate carboxykinase (PEPCK) mRNA abundance were assessed by qRT-PCR as described previously (Buettner et al., 2005). Quantification of these peptides and their copy number was normalized for GAPDH and 18S to correct for loading irregularities. The data presented are those normalized by GAPDH.

Statistical analysis. All values shown are expressed as mean±SE. Statistical analyses were performed using analysis of variance in multiple comparisons and unpaired, nonparametric Student's t test. When the main effect was significant, a two-tailed post hoc test (Tukey's) was applied to determine individual differences between means. A P value <0.05 was considered to be statistically significant. All statistical analyses were performed using SPSS for Windows.

Results

IGF-1, IGF-1 receptor and IGFBP-3 in the rat hypothalamus. FIG. 2 demonstrates the gene expression of IGF-1, IGF-1 receptor and IGFBP-3 in the mediobasal segment of the hypothalamus.

To examine the effect of the acute ICV administration of IGF-1, IGFBP-3 and the NLS-IGFBP-3 mutant on peripheral and hepatic insulin action, 18 rats that received a primed-constant infusion of these peptides ICV were compared with 12 control rats receiving vehicle infusion. There were no differences in the body weight and average food intake among the different groups of rats compared to controls. The amount of visceral fat was comparable in all the groups at the time of sacrifice. Plasma insulin, glucose, and FFA concentrations were similar in the rats assigned to the different experimental groups (Table 1, 2). Plasma GH and IGF-1 levels were similar between the groups at the end of the clamp study, demonstrating that ICV infusions did not alter the peripheral GH and IGF-1 levels (Table 3, 4). Consistent with these findings, the lack of an effect of acute infusion of ICV IGF-1 on the peak, trough, interpeak or mean 6 hour peripheral growth hormone levels has been demonstrated previously (Harel and Tannenbaum, 1992).

TABLE 1

Body composition and basal metabolic characteristics of Sprague-Dawley rats.

|  | aCSF | IGF-1 |
|---|---|---|
| N | 6 | 6 |
| Body weight (g) | 291 ± 10 | 294 ± 14 |
| Food intake (g) | 21 ± 1 | 22 ± 2 |
| Visceral fat (g) | 4.3 ± 0.5 | 4.0 ± 0.2 |
| Glucose (mM) | 7.5 ± 0.3 | 7.6 ± 0.1 |
| Insulin (ng/ml) | 1.95 ± 0.08 | 1.94 ± 0.32 |
| FFA (mEq/L) | 0.61 ± 0.07 | 0.70 ± 0.04 |
| Leptin (ng/ml) | 0.88 ± 0.05 | 0.91 ± 0.05 |

TABLE 2

Body composition and basal metabolic characteristics of Sprague-Dawley rats.

|  | aCSF | IGFBP-3 | NLS |
|---|---|---|---|
| N | 6 | 6 | 6 |
| Body weight (g) | 346 ± 11 | 333 ± 16 | 333 ± 15 |
| Food intake (g) | 26.4 ± 2.1 | 25.8 ± 0.9 | 25.3 ± 1.6 |
| Visceral fat (g) | 5.6 ± 0.7 | 4.5 ± 0.7 | 5.4 ± 0.6 |
| Glucose (mM) | 7.6 ± 0.1 | 7.7 ± 0.3 | 7.7 ± 0.2 |
| Insulin (ng/ml) | 1.43 ± 0.11 | 1.36 ± 0.07 | 1.24 ± 0.54 |
| FFA (mEq/l) | 0.79 ± 0.09 | 0.92 ± 0.05 | 0.85 ± 0.11 |
| Leptin (ng/ml) | 2.67 ± 0.18 | 2.50 ± 0.23 | 2.09 ± 0.47 |

TABLE 3

Metabolic parameters during basal and hyperinsulinemic clamp in ICV studies.

|  | aCSF | IGF-1 |
|---|---|---|
| N | 6 | 6 |
| Glucose (mmol/l) | 7.4 ± 0.5 | 7.3 ± 0.1 |
| Insulin (uU/ml) | 44.8 ± 6.4 | 40.53 ± 6.0 |
| FFA (mEq/l) | 0.35 ± 0.06 | 0.23 ± 0.02* |
| Leptin (ng/ml) | 1.77 ± 0.72 | 2.18 ± 0.48 |
| GH (ng/ml) | 1.85 ± 0.93 | 2.15 ± 0.94 |
| IGF-1 (ng/ml) |  |  |
| rat | 555 ± 35 | 554 ± 31 |
| human | 0 | 0 |
| GIR (mg/kg/min) |  |  |
| Clamp | 13.22 ± 1.07 | 19.08 ± 1.55* |
| Rd (mg/kg/min) |  |  |
| Clamp | 18.5 ± 0.97 | 21.62 ± 0.74 |
| HGP (mg/kg/min) |  |  |
| Basal | 11.71 ± 0.36 | 12.4 ± 1.65 |
| Clamp | 5.33 ± 0.68 | 2.49 ± 0.54* |
| Glycolysis (mg/kg/min) |  |  |
| Basal | 6.80 ± 0.48 | 7.02 ± 0.93 |
| Clamp | 11.99 ± 0.62 | 13.53 ± 1.17 |
| Glycogen synthesis |  |  |
| Basal | 4.91 ± 0.43 | 4.87 ± 0.87 |
| Clamp | 6.54 ± 0.53 | 8.09 ± 0.67 |

Data are mean ± SE
*P < 0.05 vs. aCSF.
Sprague-Dawley rats underwent 6 hours of ICV infusion. Basal glucose turnovers where established from 120 min to 240 min. Rats underwent a hyperinsulinemic euglycemic clamp from 240 min till the end of the study. Plasma glucose, IGF-1, insulin, FFA levels, GIR, HGP, Rd, Glycolysis and glycogen synthesis were averaged over the last 60 min of the study.

TABLE 4

Metabolic parameters during basal and hyperinsulinemic clamp in ICV studies.

|  | aCSF | IGFBP-3 | NLS |
|---|---|---|---|
| N | 6 | 6 | 6 |
| Glucose (mmol/l) | 7.4 ± 0.2 | 7.5 ± 0.4 | 7.7 ± 0.2 |
| Insulin (uU/ml) | 49.8 ± 2.0 | 57.8 ± 3.8 | 55.4 ± 11.5 |
| FFA (mEq/l) | 0.30 ± 0.04 | 0.72 ± 0.06* | 0.35 ± 0.05# |
| Leptin (ng/ml) | 2.44 ± 0.29 | 3.05 ± 0.83 | 2.79 ± 0.77 |
| GH (ng/ml) | 2.75 ± 0.91 | 1.28 ± 0.21 | 2.87 ± 0.94 |
| IGF-1 (ng/ml) | 531 ± 125 | 667 ± 62 | 595 ± 81 |
| h-IGFBP-3 (ng/ml) | 0 | 0 | 0 |
| GIR (mg/kg/min) Clamp | 15.52 ± 1.74 | 6.95 ± 1.11** | 11.98 ± 1.14# |
| Rd (mg/kg/min) Clamp | 20.49 ± 1.45 | 14.01 ± 0.82** | 17.38 ± 1.11# |
| HGP (mg/kg/min) Basal | 13.62 ± 0.80 | 13.95 ± 0.99 | 13.00 ± 0.72 |
| Clamp | 4.86 ± 0.48 | 7.08 ± 0.59** | 5.37 ± 0.65 |
| Glycolysis (mg/kg/min) Basal | 8.41 ± 0.68 | 9.33 ± 1.27 | 7.40 ± 0.71 |
| Clamp | 12.68 ± 0.61 | 9.95 ± 1.05* | 10.44 ± 0.96 |
| Glycogen synthesis Basal | 5.38 ± 0.66 | 4.62 ± 0.69 | 5.34 ± 0.38 |
| Clamp | 7.94 ± 1.25 | 4.46 ± 0.68* | 6.93 ± 0.37## |

Data are means ± SE
**P < 0.01,
*P < 0.05 vs. aCSF,
P < 0.01
P < 0.05 vs. IGFBP-3.

Sprague-Dawley rats underwent 6 hours of ICV infusion. Basal glucose turnovers where established from 120 min to 240 min. Rats underwent a hyperinsulinemic euglycemic clamp from 240 min till the end of the study. Plasma glucose, IGF-1, insulin, FFA levels, GIR, HGP, Rd, Glycolysis and Glycogen synthesis were averaged over the last 60 min of the study.

Figure 3C:
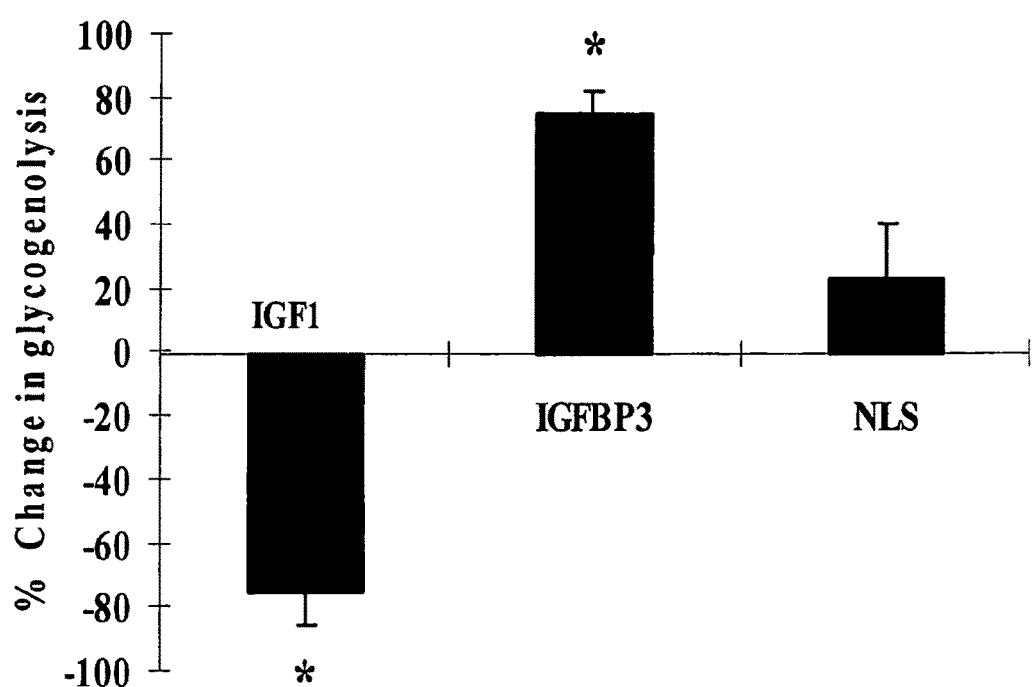

Effects of central IGF-1 and IGFBP-3 on HGP at basal and during hyperinsulinemic clamp. See Tables 3 and 4 and FIG. 3A, B. Under basal conditions, there was no difference in the endogenous glucose production between the groups. During hyperinsulinemic clamp, similar insulin levels were achieved, and plasma glucose was clamped at 7-8 mM in all the groups. Hepatic glucose production was significantly decreased in all the groups under hyperinsulinemic clamp. In the presence of ICV IGF-1, the HGP was significantly lower (FIG. 3A and Table 3) compared to controls in spite of no changes in the peripheral IGF-1 levels between the groups. In contrast, in the presence of ICV IGFBP-3 (FIG. 3B and Table 4), hepatic glucose production was significantly increased compared to controls. While ICV IGF-1 resulted in a 50% lower HGP than controls, IGFBP-3 resulted in a 45% increase in HGP compared to controls. In the presence of ICV NLS mutant infusion, HGP during both basal and hyperinsulinemic conditions were similar to controls (FIG. 3B, Table 4).

Effects of central IGF-1 and IGFBP-3 on Hepatic Glucose Flux. (See FIG. 3C). With infusion of IGF-1 or IGFBP-3 ICV, there were marked changes in HGP. It was determined if ICV IGF-1 and IGFBP-3 modified the relative contributions of plasma glucose, gluconeogenesis, and glycogenolysis to the hepatic glucose 6-phosphate pool. A marked decrease in the contribution of glycogenolysis to HGP was demonstrated in rats receiving ICV IGF-1 (p<0.01) while gluconeogenesis showed no change. IGFBP-3 on the other hand, resulted in significant increase in glycogenolysis (p<0.01 compared to controls) with no changes in gluconeogenesis (0.3±0.1, 0.54±0.2, 0.37±0.1 mg/kg/min in aCSF, IGF-1, IGFBP-3 respectively). There were no changes in glucose fluxes compared to controls in the NLS mutant group.

At the end of the clamp, the relative abundance of key gluconeogenic enzyme PEPCK and Glc-6-Pase mRNA in the liver was calculated by quantitative real time PCR (qRT-PCR) and compared as a ratio to the concentration of a reference gene, GAPDH. PEPCK mRNA in the liver of rats receiving ICV IGF-1 or IGFBP-3 for 6 h was similar to vehicle-infused rats (2.5±0.5, 3.4±0.6, 3.2±0.3 in saline, IGF-1, IGFBP-3 respectively) reflecting the lack of change in gluconeogenesis. In parallel with the significant reduction in HGP and glycogenolysis by tracer methodology, the expression of G-6 Pase was significantly 3 fold lower in animals that received IGF-1 (7.4±0.5 vs. 2.6±0.6 in aCSF and IGF-1, p<0.001). In spite of an increase in HGP, there were no changes in expression levels of G6Pase in the group that received ICV IGFBP-3. This effect of ICV IGF-1 and IGFBP-3 may explain the redistribution of hepatic glucose fluxes between gluconeogenesis and glycogenolysis.

Figure 4A:
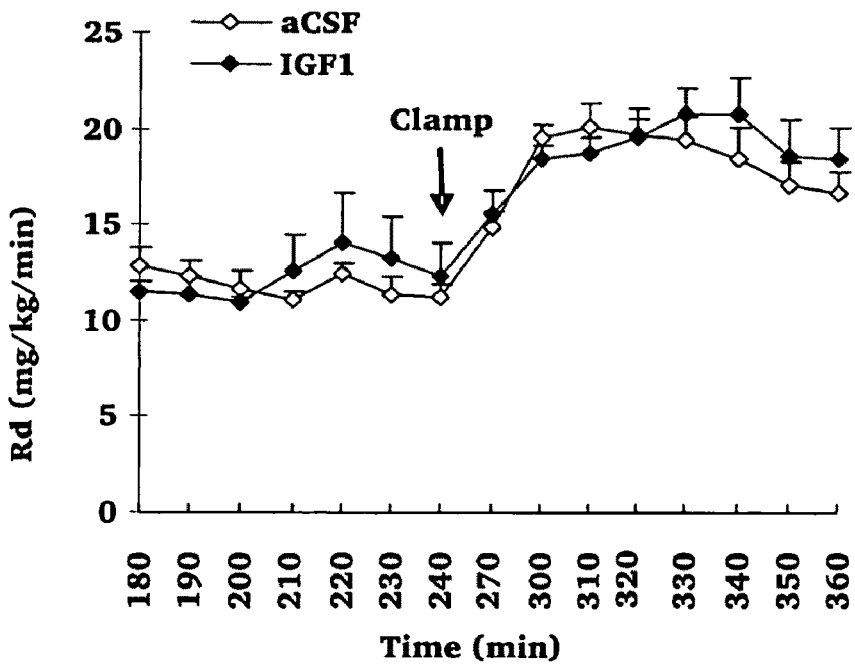
FIG. 4A-4C. Graphs of experimental results showing the effect of ICV infusion of IGF-1 (Panel A) or IGFBP-3 (Panel B) on peripheral glucose uptake and glycolysis and glycogen synthesis (Panel C). In Panel A, young rats were subjected to 6 hr of ICV infusion of aCSF (control, open triangles) or 1 μg of IGF-1 (0.3 μg bolus followed by 0.7 μg over 6 hours, shaded squares). The rats were subjected to hyperinsulinemic clamp (3 mU/Kg/min) over the last 2 hours. ICV IGF-1 marginally increased peripheral glucose uptake, but this was not statistically significant. In Panel B, young rats were subjected to 6 hr of ICV infusion of aCSF (control, open triangles) or 5 μg of IGFBP-3 (shaded triangle) or NLS-IGFBP-3 mutant (shaded circle). The rats were subjected to hyperinsulinemic clamp (3 mU/Kg/min) over the last 2 hours. ICV IGFBP-3 significantly impaired peripheral glucose uptake (Rd) (p<0.01). IGFBP-3 NLS mutant did not change Rd. In Panel C, young rats were subjected to 6 hr of ICV infusion of aCSF (control, open triangles) or 1 μg of IGF-1 (shaded squares). The rats were subjected to hyperinsulinemic clamp (3 mU/Kg/min) over the last 2 hours. Increase in Rd with ICV IGF-1 was distributed towards both glycolysis and glycogen synthesis. ICV IGFBP-3 decreased both glycolysis and glycogen synthesis significantly (p<0.05), while the NLS-IGFBP-3 mutant produced no change compared to controls.
Figure 4B:
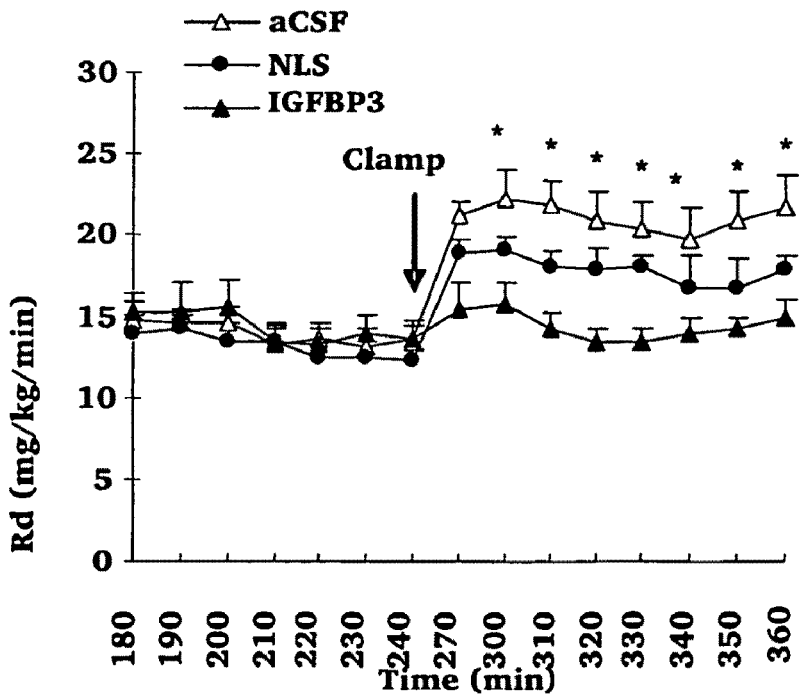
Figure 4C:
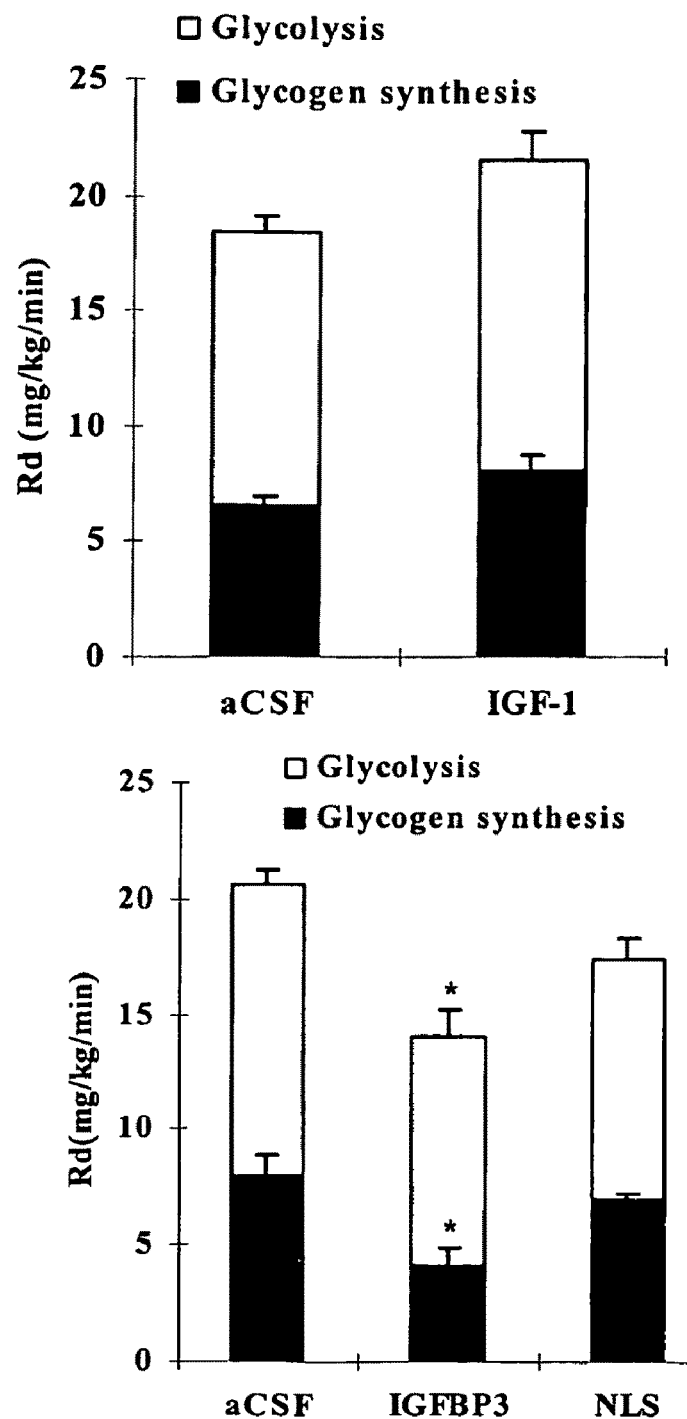

Effects of ICV IGF-1 and IGFBP-3 on Insulin-mediated Glucose Disposal, Glycolysis, and Glycogen Synthesis. See Tables 3 and 4 and FIG. 4A-C. The effect of increase in the circulating insulin concentrations in the presence of ICV IGF-1 on the rates of tissue glucose uptake ($R_d$), glycolysis, and glycogen synthesis are displayed in FIG. 4A, C. All measurements were performed during the final 60 min of the clamp study, a time when steady-state conditions were achieved for plasma glucose and insulin concentrations, glucose specific activity and rates of glucose infusion. ICV IGF-1 tended to augment the effect of physiologic increments in the plasma insulin concentration on whole body glucose disposal, though this increase was not statistically significant (Table 3, FIG. 4A). In contrast, IGFBP-3 significantly decreased peripheral glucose uptake (Table 4, FIG. 4B). The infusion of the NLS mutant of IGFBP-3 did not result in significant changes in Rd, but the values obtained were intermediate between IGFBP-3 and aCSF. Notably, in separate experiments, IGFBP-3 and NLS-IGFBP-3 bound equally to $^{125}$I-labeled IGF-1 in Western ligand blots (data not shown) but fails to internalize into cells due to its inability to bind to transferrin and importin (Schedlich et al., 2000; Lee et al., 2004).

It was next examined whether ICV IGF-1, IGFBP-3, or IGFBP-3 NLS mutant exerted any effect on the partitioning of glucose disposal into glycogen synthesis and glycolysis. Concomitant with the trend in increase in Rd, both glycolysis and glycogen synthesis was increased in IGF-1 groups compared to controls. There was significant decrease in both glycolysis and glycogen synthesis in IGFBP-3 infused animals (FIG. 4C), while the NLS mutant showed no change compared to controls.

Effects of ICV IGF-1 and IGFBP-3 on FFA levels during the clamp. (See Table 3, 4). Hyperinsulinemia during the clamp suppressed FFA levels in the control groups as expected. In the rats that received ICV IGF-1, the suppression of FFA was significantly higher (compared to controls) reflecting an overall improvement in insulin action. On the contrary, with infusion of IGFBP-3 ICV, insulin induced suppression of serum FFA levels was significantly reduced. This occurring along with a decrease in Rd and increased HGP reflects an overall decline in insulin action.

Figure 5A:
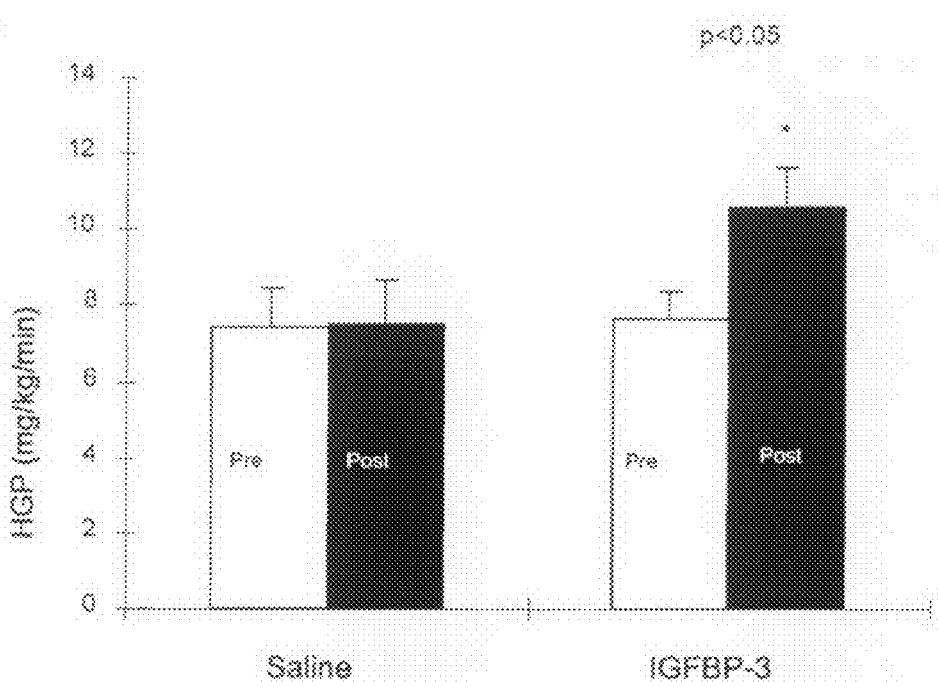
FIG. 5A-5B. Graphs showing the effect of peripheral infusion of IGFBP-3 on hepatic insulin action (Panel A) or peripheral glucose update (Panel B). In Panel A, young rats were subjected to 5 hr of hyperinsulinemic clamp (3 mU/Kg/min). At minute 120, rats received an infusion of either saline (n=6) or IGFBP-3 (0.06 mg/kg/hr IV, n=6) for 3 hours. Infusion of IGFBP-3 resulted in a significant increase in HGP compared to saline infused controls (p<0.05). In Panel B, young rats were subjected to 5 hr of hyperinsulinemic clamp (3 mU/Kg/min). At minute 120, rats received infusion of either saline (n=6) or IGFBP-3 (0.06 mg/kg/hr IV, n=6) for 3 hours. Infusion of IGFBP-3 resulted in a significant decrease in Rd (peripheral glucose uptake) compared to saline infused controls (p<0.01).
Figure 5B:
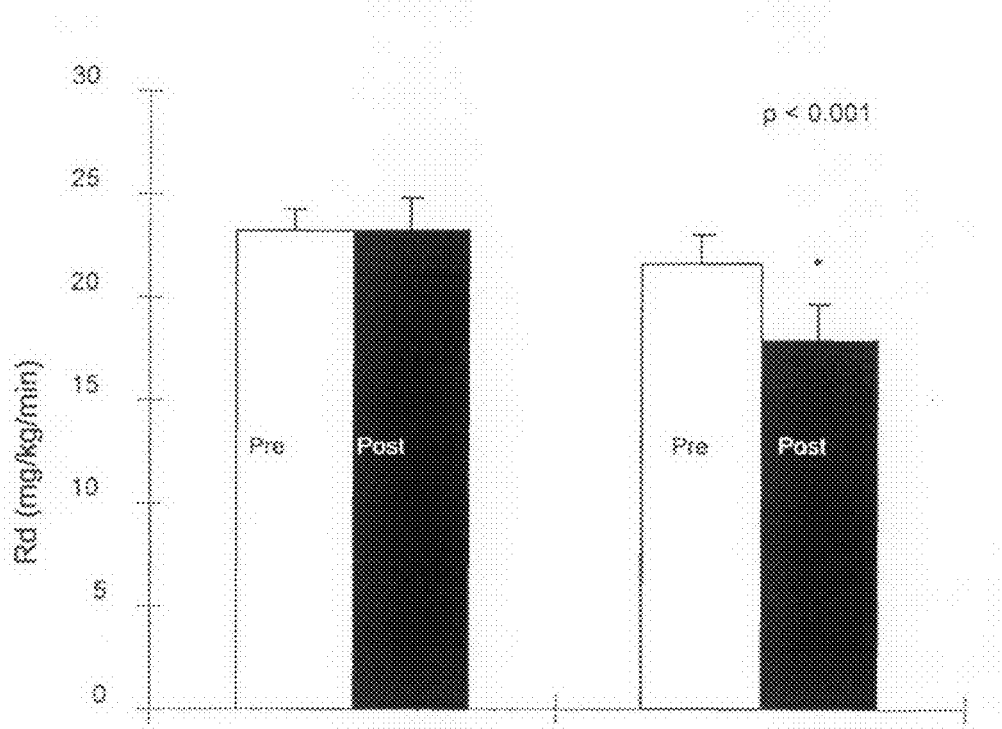

Effects of peripheral infusion of IGFBP-3 on hepatic and peripheral insulin action. See FIG. 5A, B. To determine if peripheral infusion of IGFBP-3 affects insulin action, saline or IGFBP-3 was infused during hyperinsulinemic clamp to two groups of rats that were matched for body weight (~260 gm), visceral fat (~3.5 grams), basal glucose (~135 mg % or 7 mM), FFA (~0.55mEq/l) and insulin levels (~1.7 ng/ml). The resulting human IGFBP-3 levels during the IGFBP-3 infusion were 1960±360 ng/ml. The levels are similar to levels seen in physiological insulin resistance states such as puberty (Lofqvist et al., 2005) and old age (Munzer et al., 2006). IGFBP-3 induced a ~17% reduction in insulin stimulated glucose uptake and 30% higher HGP (FIG. 5A B) compared to controls under similar hyperinsulinemic clamp conditions. Rat CSF was tested for entry of peripherally infused IGFBP-3 through the blood brain barrier and detected levels with a mean 7 ng/ml, indicating some uptake into the CNS. These studies demonstrate that IGFBP-3 directly affects peripheral glucose metabolism, probably through the CNS.

Discussion

As demonstrated herein, IGF-1 and IGFBP-3 affect peripheral insulin action through central mechanisms. Infusion of IGF-1 in to the third ventricle was able to affect peripheral hepatic insulin action even in the absence of demonstrable leak of hIGF-1 in to the periphery or change in peripheral GH levels. These studies may explain the apparent puzzle of significant metabolic effects of IGF-1 at the level of the liver in the absence of substantial amounts of hepatic IGF-1 receptors (Frick et al., 2000). Considering the metabolic effects of peptides such as leptin and insulin that affect hepatic insulin action through the hypothalamus (Halaas et al., 1995) and the abundance of IGF-1 and its receptors in the brain, a central action of IGF-1 is not surprising (Niblock et al., 1998; Sonntag et al., 1999). Similar to leptin and insulin, IGF-1 has been demonstrated to be transported across the blood brain barrier and is present in the cerebrospinal fluid (Pan and Kastin, 2000). In addition, the tissue levels of IGF-1 in the hypothalamic area may be higher than the levels in the CSF because of local production of IGF-1. Because a recent study showed a rapid clearance of CSF IGF-1 following a lateral ventricle infusion (Nagaraja et al., 2005), the study was designed to achieve physiological metabolic effects through a continuous infusion. The doses of IGF-1 chosen in these studies are small and not significantly higher (in molar quantities) than the doses of ICV insulin that demonstrate a physiological effect (Kovacs et al., 2002). Thus the central effects of IGF-1 demonstrated here on peripheral glucose metabolism appear to be physiologically relevant.

Insulin resistance observed during clamps with IGFBP-3 (in both peripheral and ICV infusions of IGFBP-3) provide the first conclusive evidence of an acute effect in vivo of this molecule. It is demonstrated that IGFBP-3 influences overall insulin action through decreases in insulin-induced suppression of HGP, decrease in RD and FFA. The effects of central IGFBP-3 on overall systemic insulin action are in contrast to central IGF-1 where the predominant effect was at the level of the liver. As is often observed in other systems, it is possible that some of the in vivo effect is secondary to IGF-1 binding (and thus decreased availability of IGF-1) in addition to IGF independent effects (Lee and Cohen, 2002). Liver specific IGF-1 knock out (LID) mice demonstrate significant insulin resistance at the level of muscle. In LID mice, the circulating IGF-1 levels are low at 10-20% of control (Yakar et al., 2004) but IGFBP-3 levels are only 50% reduced (Cohen et al, unpublished data) and GH levels are very high. Inhibition of GH action in LID mice leads to improved insulin sensitivity, however, this is also associated with a reduction in GH-dependent proteins such as IGFBP-3, which can contribute towards the improved sensitivity, further demonstrating the complex role of GH/IGF-1/IGFBP-3 axis in glucose metabolism (Yakar et al., 2004).

IGFBP-3 mutants with altered interactions with its protein partners serve as useful tools to evaluate the mechanisms of specific effects of this pleiotropic molecule. The NLS mutant of IGFBP-3 is the only mutant that is currently available in sufficient quantities for in vivo use. The NLS mutant IGFBP-3 protein binds IGF-1 normally, but fails bind to other IGFBP-3 ligands, including cell-surface proteins, preventing cell binding and internalization (Lee et al., 2004; Butt et al., 2002), importin-beta, preventing nuclear transport (Schedlich et al., 2000), various extracellular matrix proteins, such as transferrin and type-1 collagen, (Weinzimer et al., 2001; Liu et al., 2003), and various soluble, intracellular, extracellular and circulating proteins (Oufattole, 22006). The mutant fails to internalize into cells and does not mediate nuclear actions of IGFBP-3 in spite of normal IGF-binding and equal inhibition of IGF-dependent effects. Here, in vivo, this mutant minimally inhibited hepatic and peripheral insulin action. The decreased activity of the NLS-mutant IGFBP-3 demonstrates that IGF-I binding alone is insufficient to mediate the central effects of IGFBP-3 observed. Therefore, it can be concluded that the action of IGFBP-3 on the hypothalamus involves activity mediated by interfacing with additional molecules in addition to IGFs. The partial, but not significant effects of the NLS mutant is compatible with some inhibition of local IGF action as a component of the effect of IGFBP-3 in the CNS. IGF-independent effects of IGFBP-3 on Akt have been described in adipocytes (Chan et al., 2005) and endothelial cells (Franklin et al., 2003). Once inside the cell, IGFBP-3 can rapidly internalize into the nucleus, where it has the ability to bind RXR and modulate its signaling (Liu et al., 2000) and as noted in 3T3-L1 adipocytes in response to TNF-a (Shim et al., 2001). This binding of IGFBP-3 to RXR-a can impair PPAR-y signaling (Ikezoe et al., 2004). PPAR has been located in various regions of the brain and have been implicated in glucose metabolism in the brain (Dello Russo et al., 2003). Therefore, it is hypothesized that IGFBP-3-induced impairment of nuclear signaling or some other intracellular action of IGFBP-3 leads to insulin resistance.

It is interesting to compare the effects of central and peripheral infusions of IGFBP-3 on insulin action. It appears that IGFBP-3 antagonizes insulin action through distinct mechanisms in the CNS involving both IGF-dependent and IGF-independent pathways. The effects of peripheral infusion of IGFBP-3 on glucose metabolism could also be centrally mediated as the levels of hIGFBP-3 detected in the CSF, during a peripheral infusion of this protein, can not attest to its availability near the hypothalamus, its internalization, and local production in the brain. IGFBP-3 is recognized to be expressed in brain tissue, and its levels are within the physiologically active range in the CSF (Rensink et al., 2002). Furthermore, IGFBP-3 is elevated in the brains of patients with Alzheimer's disease (Muzumdar et al., 2003) and it is intriguing to speculate that this is involved in the well recognized insulin resistance in this condition. The extent of the individual contribution of IGF-1 dependent vs. non IGF-1 dependent of a peripheral IGFBP-3 infusion can only be discerned by studying the effects of peripheral infusions with a non IGF-1 binding mutant of IGFBP-3 in vivo; however, these studies must await large-scale production of these proteins.

Thus, IGF-1 and IGFBP-3 appear to have opposing effects on glucose metabolism and their balance may play a prominent role in glucose homeostasis. As with other peripheral peptides such as insulin and leptin, much of these effects seem to be mediated through the hypothalamus. An independent effect of IGFBP-3 on insulin action is particularly significant as IGFBP-3 is about to undergo phase II clinical trials as an anticancer drug. Dissecting the differences in effects of these peptides is extremely important to develop treatment modalities without unwanted side effects.

Example 2

Neuroprotective Peptide Humanin is a Potent Insulin Sensitizer Via a Central Mechanism Example Summary Humanin (HN), a newly identified anti-apoptotic peptide has broad neurosurvival effects, especially against Alzheimer disease-associated insults. HN acts by binding and antagonizing pro-apoptotic molecules such as IGFBP-3. It was recently demonstrated that IGFBP-3 induces insulin resistance in vivo by acting through a central, IGF-independent mechanism (Example 1). It was therefore hypothesized that HN may also regulate insulin sensitization in vivo. Small doses of HN were infused into third ventricle (ICV) of awake, unstressed and chronically catheterized FBN rats and studied under basal and hyperinsulinemic clamp (3mU/kg/min). With ICV infusion of HN, glucose infusion rate (GIR) during the hyperinsulinemic clamp was 165% of aCSF (25.2±2.6 vs. 15.0±0.6; $p<0.01$). The increase in GIR was accounted by a ~50% more reduction in hepatic glucose production (HGP) and ~150% increase in peripheral glucose uptake (Rd) demonstrating that HN ICV markedly increased both hepatic and peripheral insulin sensitivity. Infusion of the F6A mutant of humanin ICV (this mutant does not bind IGFBP-3) suppressed HGP to almost zero ($p<0.005$ compared to controls and $p<0.05$ compared to humanin). It is concluded that humanin has potent centrally mediated effects on insulin action and may represent a novel link between diabetes and neurodegeneration.

Introduction

Humanin binds to a variety of protein partners, including IGFBP-3 and bax-related proteins and this binding to proapoptotic molecules is one of the mechanisms by which it promotes cell survival (Guo et al., 2003; Ikonen et al., 2003). The interaction of HN with IGFBP-3 is especially interesting as IGFBP-3 has been shown to induce insulin resistance both in vivo and in vitro (Kim et al., 2006). Furthermore it was previously demonstrated that central IGFBP-3, independent of IGF-1 binding, induces peripheral insulin resistance. As IGFBP-3 and HN physically bind each other and have opposite roles on cell survival, (IGFBP-3 induces apoptosis and HN promotes cell survival), it was hypothesized that HN may have insulin sensitizing effects in vivo. This hypothesis was further based on the fact that IR plays a role in the pathogenesis and progression of AD and both IGFBP-3 and HN are present in AD brain (Rensink et al., 2002).

To identify if HN influenced insulin action through the brain, HN ICV was infused and several aspects of peripheral insulin action were carefully monitored. To demonstrate if this effect is altered or influenced by the binding of HN to IGFBP-3, the analog of HN that does not bind IGFBP-3 ICV was used to study its effects in peripheral insulin action.

Materials and Methods

Figure 6:
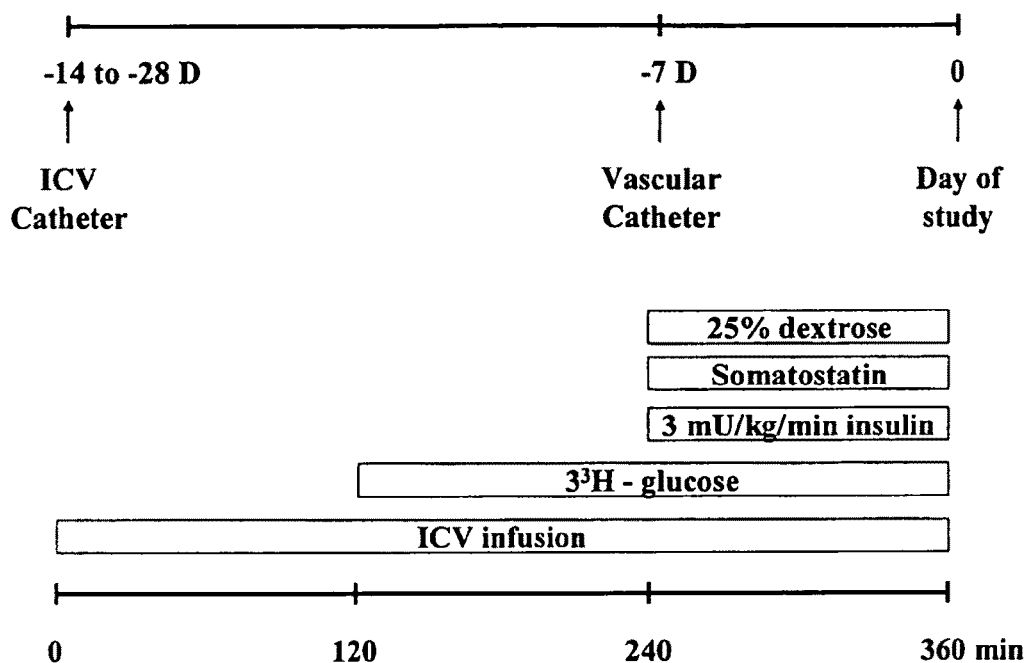
FIG. 6 is a schematic representation of the experimental design for the ICV studies. The upper panel demonstrates the time line for the surgical procedures. Surgical implantation of ICV catheters was performed 2-4 weeks before the clamp study and intravascular catheters were implanted in the week before the clamp. The lower panel demonstrates the protocol on the day of the clamp. ICV HN, F6A HN or aCSF infusions were initiated at the beginning of the study (t=0) and continued throughout the clamp. Infusion of labeled glucose was begun at t=120 and was continued throughout the study. The infusions of somatostatin and insulin were initiated at t=240 and continued for the remaining 2 h. A 25% glucose solution was infused as needed during the last two hours to maintain plasma glucose concentration.

Animals. Young (3 mo old, n=6 in each group), male Sprague-Dawley rats (Charles River Laboratories, Wilmington, Mass.) were used for this study. Rats were housed in individual cages and were subjected to a standard light (6:00 AM to 6:00 PM)-dark (6:00 PM to 6:00 AM) cycle. All rats were fed ad libitum using regular rat chow that consisted of 64% carbohydrate, 30% protein, and 6% fat with a physiological fuel value of 3.3-kcal/g chow. 2 to 4 weeks before the in vivo study, the rats were anesthetized by inhalation of isoflurane and ICV cannula was placed in the third ventricle for infusions of humanin, humanin analog F6A HN or artificial CSF (aCSF), as previously described (Muzumdar et al., 2003) (FIG. 6). Briefly, a 26-gauge stainless steel guide cannula (Plastics One, Roanoke, Va.) was chronically implanted into the third ventricles using the following coordinates from bregma: anterior-posterior; +0.2 mm dorsal-ventral; −9.0 mm medial-lateral; 0.0 directly on the mid-sagittal suture, followed by a 28-gauge dummy cannula, inserted to prevent clogging of the guide cannula. The implant was secured to the skull with Caulk Grip dental cement, and the skin was closed over the implant using wound clips. The recovery of rats from the surgical stress was monitored with daily weight, food intake, and movement.

Upon recovery of body weight, usually a week, indwelling catheters were placed in the right internal jugular vein and in the left carotid artery (Muzumdar et al., 2003). The venous catheter was extended to the level of the right atrium, and the arterial catheter was advanced to the level of the aortic arch. Recovery was continued until body weight was within 3% of the pre-operative weight (~4-6 days). In the rats that received peripheral humanin, only the vascular catheters were placed.

Basal and hyperinsulinemic clamp in ICV studies. See FIG. 6. Studies were performed in unrestrained rats using the insulin clamp technique, in combination with high performance liquid chromatography-purified [3-$^3$H]glucose, as described previously (Liu et al., 1998). Food was removed for ~5 h before the in vivo protocol. All studies lasted 360 min and included a 120-min equilibration period, a 120-min basal period for assessment of the basal glucose turnover, and a 120-min hyperinsulinemic clamp period. All rats received ICV infusions (bolus followed by continuous ICV infusions of humanin, F6A HN or aCSF, depending on the group) over the entire 6 hours of the study. At the beginning of the basal period and 120 min before starting the glucose/insulin infusions, a primed-continuous infusion of high performance liquid chromatography-purified [3-$^3$H]glucose (NEN Life Science Products, Boston, Mass.; 20 µCi of bolus, 0.2 µCi/min) was initiated and maintained throughout the remaining 4 h of the study. In the final 2 hours of the study, the rats were subjected to hyperinsulinemic clamp. The protocol followed during the insulin clamp study was similar to that previously described (Liu et al., 1998). Briefly, a primed-continuous infusion of regular insulin (3 milliunits/kg·min) was administered, and a variable infusion of a 25% glucose solution was started and periodically adjusted to clamp the plasma glucose concentration at 7-8 mM. To prevent endogenous insulin secretion and in order to control for possible effects of ICV infusions on the endocrine pancreas, somatostatin (1.5 µg/kg·min) was also infused in all the groups.

ICV humanin study. A bolus of humanin (6 µg) was followed by a continuous infusion over 6 hours (total dose of 18 µg, 0.1 µg/kg/min). No humanin was detected in the rat periphery confirming that there was no leak from ICV infusions.

ICV humanin mutant study. F6A HN has one amino acid substitution (F6A-phenylalanine to alanine on position 6) and has been characterized. A bolus of F6 A HN (6 µg) was followed by a continuous infusion over 6 hours (total 18 µg, 0.1 µg/kg/min).

Peripheral humanin study. To study the acute effects of an infusion of IGFBP-3, two groups of awake, unstressed, chronically catheterized Sprague-Dawley rats (~300 g) were studied for 300 min (n=3 in each group) under hyperinsulinemic clamp (as previously described). From 120 min the rats received a primed continuous infusion of humanin (0.375 mg/kg/hr) or saline (control) for an additional 2 h. Plasma samples for determination of [$^3$H] glucose and [$^3$H] water specific activities were obtained at 10-min intervals during the basal and clamp periods. Steady state conditions for the plasma glucose concentration and specific activity were achieved within 90 min in all the studies. Plasma samples for determination of HN, insulin and FFA concentrations were collected at 30-min intervals throughout the study. All determinations were also performed on portal vein blood obtained at the end of the experiments. The total amount of blood drawn during the entire study for various assays is 3 cc. After separation of plasma (subsequently used for analysis), the red blood cells were reconstituted in saline and infused back into the animal.

At the end of the clamp study, rats were sacrificed using 100 mg pentobarbital sodium/kg body wt IV. Epididymal, mesenteric, and perinephric fat pads (visceral fat) were dissected and weighed at the end of each experiment. The study protocol was reviewed and approved by the Animal Care and Use Committee of the Albert Einstein College of Medicine.

Assays and analytical procedures. Plasma glucose (sample volume 10 µl) was measured by the glucose oxidase method (Glucose Analyzer II, Beckman Instruments, Palo Alto, Calif.). Plasma [$^3$H] glucose radioactivity was measured in duplicates in the supernatants of Ba(OH)$_2$ and ZnSO$_4$ precipitates of plasma samples (20 µl) after evaporation to dryness to eliminate tritiated water. Plasma insulin (10 µl) was measured by RIA using rat insulin standard for basal studies and human insulin standard for insulin clamp studies. Plasma non-esterified fatty acid concentrations (5 µl) were determined by an enzymatic method with an automated kit according to the manufacturer's specification (Waco Pure Chemical Industries, Osaka, Japan). Humanin in the rat periphery in the groups that received these peptides ICV was similar to controls indicating that no leaks occurred during the infusions and that the effects observed in these studies are strictly central in nature.

Calculations of whole body glucose fluxes. Under steady-state conditions for plasma glucose concentrations, the rate of glucose disappearance ($R_d$) equals the rate of glucose appearance ($R_a$). The latter was calculated as the ratio of the rate of infusion of [3-$^3$H] glucose (dpm/min) and the steady-state plasma [$^3$H] glucose specific activity (dpm/mg). The rate of endogenous glucose production was calculated as the difference between $R_a$ and the infusion rate of glucose. The rates of glycolysis were estimated as described previously (Rossetti and Giaccari, 1990). Glycogen synthesis was estimated by subtracting the rate of glycolysis from the $R_d$.

Expression of humanin in the rat. Total RNA was extracted from the mediobasal wedge of rat hypothalamus, liver, muscle, heart and pancreas following Clontech's protocol. First-stranded cDNA was synthesized from 1 µg of total RNA using Superscript III (Gibco, Gaithersburg, Md.). Expression of humanin was demonstrated by RT-PCR. The conditions for PCR were 94° C. for 10 min, cycles of 94° C. for 30 sec, then annealing temperature of 60° C. for 30 sec and then 72° C. for 1.5 min. The product size was 136 by for humanin.

Western blot analyses. The indicated tissues were homogenized in 20 mM MOPS, 2 mM EGTA, 5 mM EDTA, 30 mM sodium fluoride, 40 mM beta-glycerophosphate, 10 mM sodium pyrophosphate, 2 mM orthovanadate, 0.5% NP-40 and complete protease inhibitor cocktail (Roche, Indianapolis, Ind., USA) and centrifuged at 12,000 g for 15 min and the supernatant was harvested while carefully avoiding the lipid layer on top. Protein concentration was measured with a BCA protein quantification kit (Pierce, Rockford, Ill., USA). Protein extracts were separated on 4-12% NuPAGE (Invitrogen, Carlsbad, Calif., USA) gels and were blotted onto Immobilon FL PVDF (Millipore, Billerica, Mass., USA). Membranes were blocked at room temperature for 1 hr in Odyssey LI-COR Blocking Buffer (LI-COR, Lincoln, Nebr., USA) and incubated in primary antibodies against ACC, phosphor STAT3 Y705, phospho-Akt S473, Akt, phospho-Jnk1/2, (Cell Signaling Technology, Inc., Beverly, Mass., USA), STAT3, (Santa Cruz Biotechnology, Santa Cruz, Calif., USA) and GAPDH (Research Diagnostics, Concord, Mass., USA) in 1:1 Blocking Buffer/TBS-T overnight at 4° C. Following four consecutive 5 min washes in TBS-Tween 20 (0.1%), blots were incubated with Alexa Fluor 680 donkey anti-goat IgG, Alexa Fluor 680 anti-mouse IgG (Molecular Probes, Eugene, Oreg., USA) or IR Dye 800 conjugated goat anti-rabbit IgG (Rockland, Gilbertsville, Pa., USA) for 1 hr at room temperature in blocking buffer containing 0.1% TBS-T and 0.1% SDS. After three washes in TBS-T and a final wash in TBS the blots were scanned using the LI-COR Odyssey (LI-COR, Lincoln, Nebr., USA) and quantified using Odyssey 2.0 software based on direct fluorescence measurement.

Statistical analysis. All values shown are expressed as means±SE. Statistical analyses were performed using analysis of variance in multiple comparisons and unpaired, non-parametric Student's t test. When the main effect was significant, a two-tailed post hoc test (Tukey's) was applied to determine individual differences between means. A P value <0.05 was considered to be statistically significant. All statistical analyses were performed using SPSS for Windows.

Results

Figure 7:
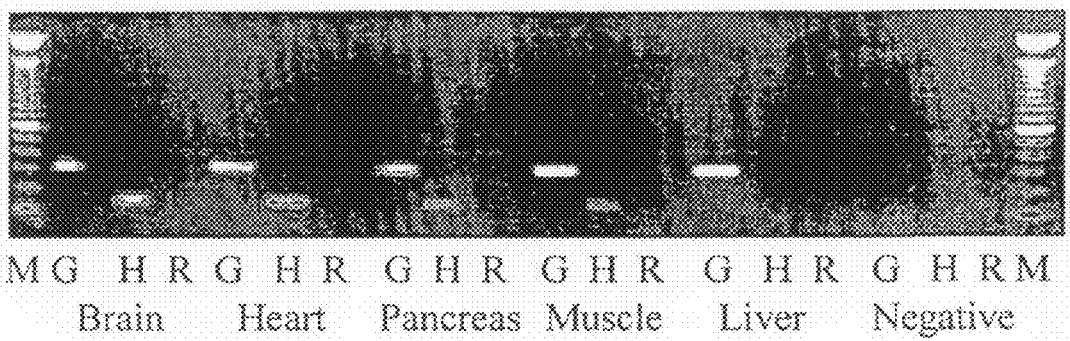
FIG. 7 is a photograph of an electrophoresis gel showing expression of HN in the rat tissues. Because of the unique expression of humanin gene within the 16S ribosomal RNA, a special protocol was designed to demonstrate its presence in various tissues. mRNA was first enriched with double treatment with an mRNA purification kit, then DNAse treatment (to eliminate DNA content), followed by cDNA synthesis. PCR followed with specially designed primers for GAPDH, humanin, and 16s rRNA (to ensure enrichment of mRNA and non-contamination with rRNA). The primer to test for humanin expression was designed within the humanin sequence. HN was highly expressed in the mediobasal hypothalamus and heart (compared to GAPDH) and was also present in pancreas and muscle.

HN is expressed in mediobasal hypothalamus. FIG. 7 demonstrates the gene expression of HN in the mediobasal segment of the hypothalamus, muscle, pancreas and heart.

Central HN improves hepatic and peripheral insulin sensitivity. See Tables 5 and 6 and FIG. 8a, b). To examine the effect of the acute ICV administration of HN on peripheral and hepatic insulin action, 6 rats that received a primed-constant infusion of HN ICV were compared to 6 control rats receiving vehicle infusion. As HN binds IGFBP-3 and IGFBP-3 significantly impairs insulin action, an analog of HN that does not bind IGFBP-3 was used to perform clamps similar to HN ICV infused groups. There were no differences in the body weight and average food intake among the different study groups. The amount of visceral fat was comparable in all the groups at the time of sacrifice. Plasma insulin, glucose, and FFA concentrations were similar in the rats assigned to the different experimental groups (Table 5). Plasma HN levels were similar between the groups at the end of the clamp study, demonstrating that ICV infusions did not alter the peripheral HN levels (Table 6).

TABLE 5

Body composition and basal metabolic characteristics of Sprague-Dawley rats

|  | aCSF | Humanin | F6A HN |
|---|---|---|---|
| N | 6 | 6 | 6 |
| Body weight (g) | 295 ± 17 | 294 ± 28 | 299 ± 8.6 |
| Food intake (g) | 24.3 ± 2.1 | 25.4 ± 0.9 | 25.3 ± 1.6 |
| Visceral fat (g) | 3.6 ± 0.59 | 3.02 ± 0.4 | 2.64 ± 0.22 |
| Glucose (g/dl) | 1.54 ± 0.09 | 1.49 ± 0.07 | 1.6 ± 0.06 |
| Insulin (ng/ml) | 1.35 ± 0.20 | 1.13 ± 0.16 | 1.0 ± 0.1 |
| FFA (mEq/L) | 1.26 ± 0.02 | 1.19 ± 0.34 | 1.18 ± 0.26 |

TABLE 6

Metabolic parameters during basal and hyperinsulinemic clamp in ICV studies

|  | aCSF | HN | F6A HN |
|---|---|---|---|
| N | 6 | 6 | 6 |
| Glucose (g/dl) | 1.41 ± 0.06 | 1.4 ± 0.04 | 1.4 ± 0.02 |
| Insulin (ng/ml) | 4.0 ± 0.28 | 4.8 ± 0.5 | 4.64 ± 0.17 |
| FFA (mEq/L) | 0.64 ± 0.07 | 0.33 ± 0.03 | 0.49 ± 0.08 |
| GIR (mg/kg/min) |  |  |  |
| Clamp Rd (mg/kg/min) | 15.0 ± 0.65 | 22.8 ± 1.64** | 22.6 ± 2.4* |
| Clamp HGP (mg/kg/min) | 19.6 ± 0.6 | 24.9 ± 1.6* | 21.4 ± 0.03 |
| Basal | 12.14 ± 0.80 | 12.87 ± 1.6 | 10.83 ± 0.6 |
| Clamp Glycolysis (mg/kg/min) | 4.65 ± 0.4 | 2.27 ± 0.37** | 0.4 ± 0.2** |
| Basal | 6.9 ± 0.78 | 7.99 ± 0.73 | 5.7 ± 1.05 |
| Clamp Glycogen synthesis | 13.1 ± 0.4 | 15.1 ± 1.0* | 12.0 ± 0.9 |
| Basal | 4.9 ± 0.3 | 4.89 ± 0.61 | 5.06 ± 0.55 |
| Clamp | 6.6 ± 0.12 | 9.75 ± 0.92* | 9.4 ± 1.51 |

Data are means ± SE
**P < 0.001,
*P < 0.05 vs. aCSF.
Sprague-Dawley rats underwent 6 hours of ICV infusion. Basal glucose turnovers where established from 120 min to 240 min. Rats underwent a hyperinsulinemic euglycemic clamp from 240 min till the end of the study. Plasma glucose, insulin, GIR, HGP, Rd, Glycolysis and glycogen synthesis were averaged over the last 60 min of the study.

Under basal conditions, there was no difference in endogenous glucose production between the groups. During hyperinsulinemic clamp, similar insulin levels were achieved, and plasma glucose was clamped at 7-8 mM in all the groups. Hepatic glucose production was significantly decreased in all the groups under hyperinsulinemic clamp. The HGP was significantly lower (FIG. 8a and Table 6) in the ICV HN group suggesting an enhanced effect of insulin on liver.

At the end of the clamp, the relative abundance of key gluconeogenic enzyme PEPCK and Glc-6-Pase mRNA in the liver was calculated by quantitative real time PCR (qRT-PCR) and compared as a ratio to the concentration of a reference gene, GAPDH.

PEPCK mRNA in the liver of rats receiving ICV HN for 6 h was similar to vehicle-infused rats (7.9±1.7, 12.4±2.7 in saline and HN respectively) suggesting a lack of change in gluconeogenesis. The expression of G-6 Pase was significantly lower in animals that received HN (2.0±0.21, 0.87±0.37 in aCSF and HN respectively, p<0.05) suggesting that the suppression of HGP was through a reduction in glycogenolysis.

The effect of increase in the circulating insulin concentrations in the presence of ICV HN on the rates of tissue glucose uptake ($R_d$), glycolysis, and glycogen synthesis were estimated. All measurements were performed during the final 60 mM of the clamp study, a time when steady-state conditions were achieved for plasma glucose and insulin concentrations, glucose specific activity and rates of glucose infusion. ICV HN significantly augmented the effects of physiologic increments in the plasma insulin concentration on whole body glucose disposal. (Table 6, FIG. 8b). Concomitant with the increase in Rd, both glycolysis and glycogen synthesis was increased in HN compared to controls.

Hyperinsulinemia during the clamp suppressed FFA levels in the control groups as expected. In the rats that received ICV HN, the suppression of FFA was significantly higher (compared to controls) reflecting an overall improvement in insulin action (Table 6). This occurring along with an increase in Rd and decreased HGP reflects an overall increase in insulin action.

Figure 9A:
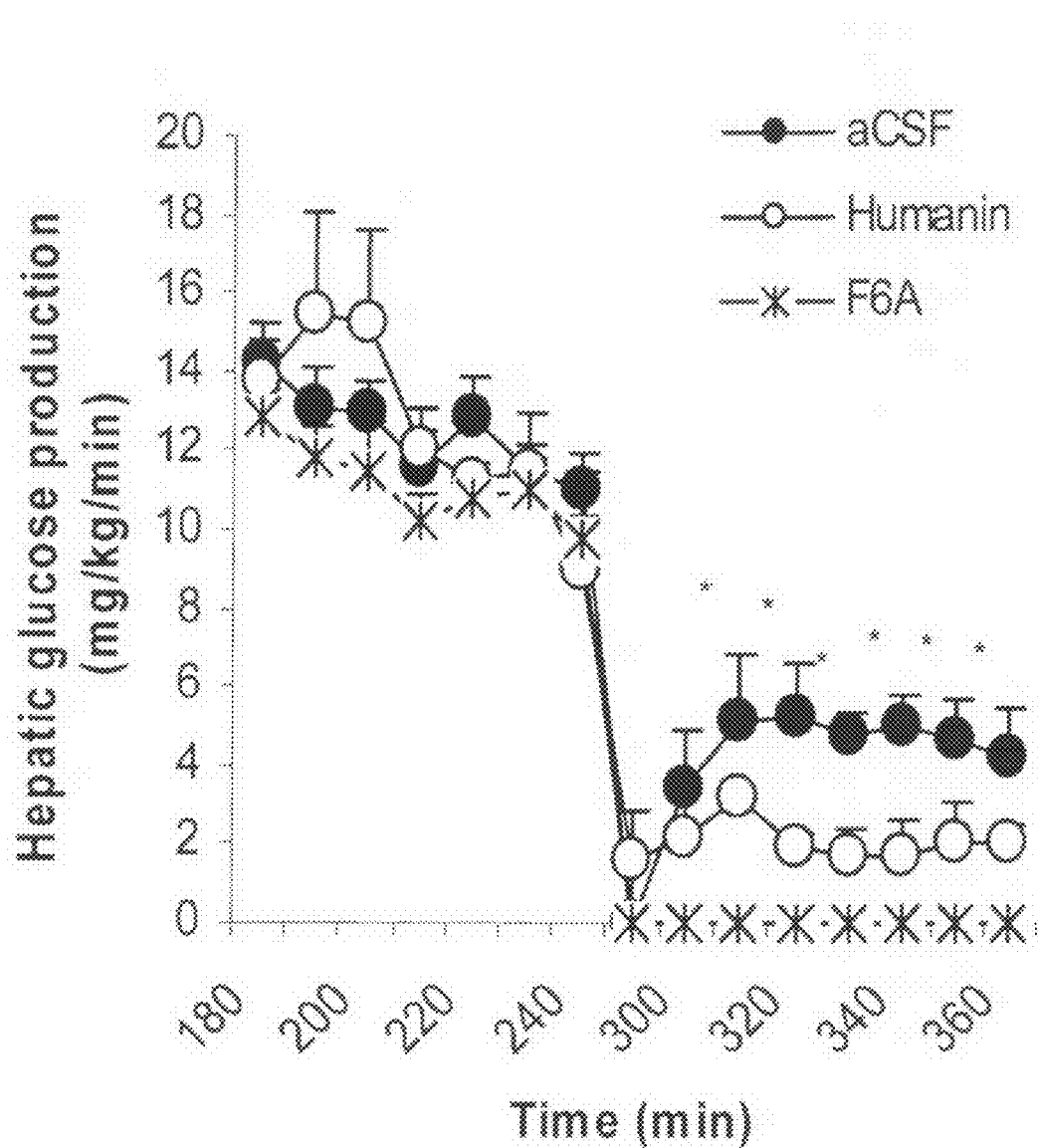

Decreased binding of humanin to IGFBP-3 further increases the effects of humanin on hepatic insulin sensitivity indicating that IGFBP-3 inhibits insulin sensitivity, in part, by interfering with humanin actions. (See Table 6 and FIG. 9a, b). F6A HN is an analog of HN that does not bind IGFBP-3. Since HN increases insulin sensitivity and IGFBP-3 induces insulin resistance, the effects of ICV F6A on glucose fluxes was studied under a similar clamp protocol. In the presence of ICV F6A HN (FIG. 8B and Table 6), hepatic glucose production was even more significantly and almost completely suppressed compared to controls. The expression of G-6 Pase was significantly lower in animals (2.0±0.21, 0.89±0.28 in aCSF and HN respectively p<0.05) suggesting that the suppression of HGP was through a reduction in glycogenolysis. PEPCK mRNA was unchanged (7.9±1.7, 10.54±1.4 in saline and F6A HN respectively) suggesting a lack of change in gluconeogenesis.

The infusion of F6A HN did not result in significant changes in Rd, but the values obtained were intermediate between aCSF and HN. Similar trends were noticed in the suppression of FFA under clamp.

Figure 10A:
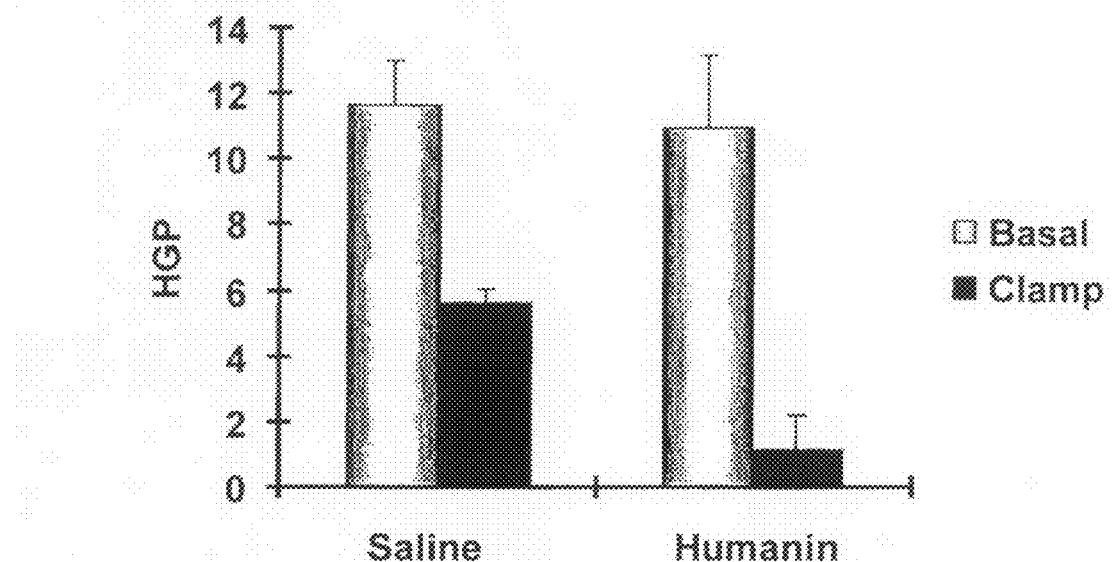
FIG. 10A-10B. Graphs showing the effect of peripheral infusion of HN on hepatic insulin action peripheral glucose uptake. Young rats were subjected to 5 hr of hyperinsulinemic clamp (3mU/Kg/min). At minute 120, rats received an infusion of either saline (n=6) or HN (0.375 mg/kg/hr IV, n=3) for 3 hours. Infusion of HN resulted in a significant increase in hepatic insulin sensitivity compared to saline infused controls (Panel A, $p<0.05$). There were no changes in Rd (peripheral glucose uptake) compared to saline infused controls (Panel B).
Figure 10B:
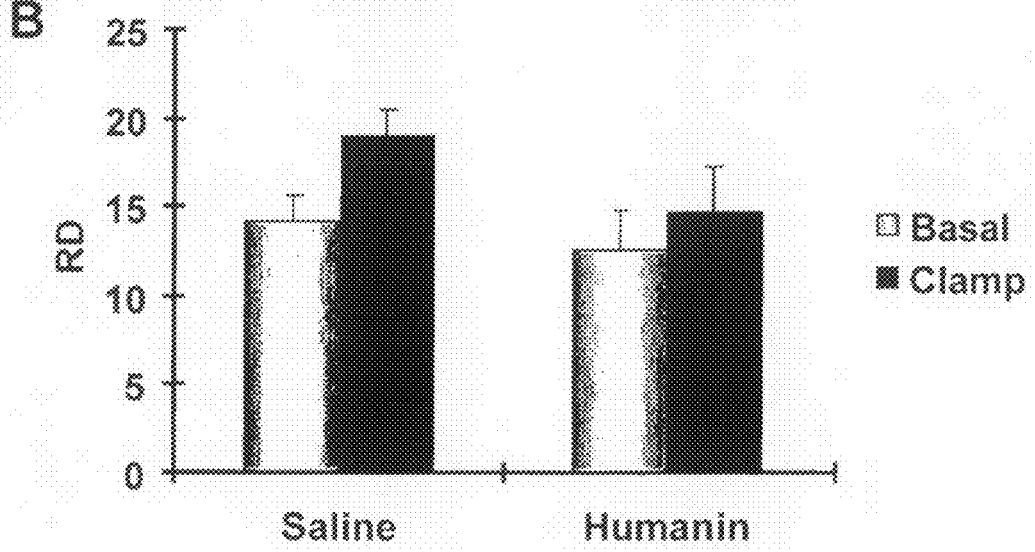

Effects of peripheral Infusion of humanin on hepatic and peripheral insulin action. To determine if peripheral infusion of humanin affects insulin action, saline or humanin was infused during hyperinsulinemic clamp to two groups of rats that were matched for body weight (~300 gm), visceral fat (~3.5 grams), basal glucose (~135 mg % or 7 mM), FFA (~0.55 mEq/1) and insulin levels (~1.7 ng/ml). Humanin increased hepatic insulin sensitivity by 80% while peripheral glucose uptake was unchanged (FIG. 10a, b). Rat CSF was tested for entry of peripherally infused humanin through the blood brain barrier. Levels in the range of 0-40 ng/ml (mean 7 ng/ml), or two orders of magnitude less than those achieved through direct ICV infusion were detected, indicating little or no uptake into the CNS. These studies demonstrate that humanin, in addition to effects through the CNS, directly affects peripheral glucose metabolism.

Figure 11A:
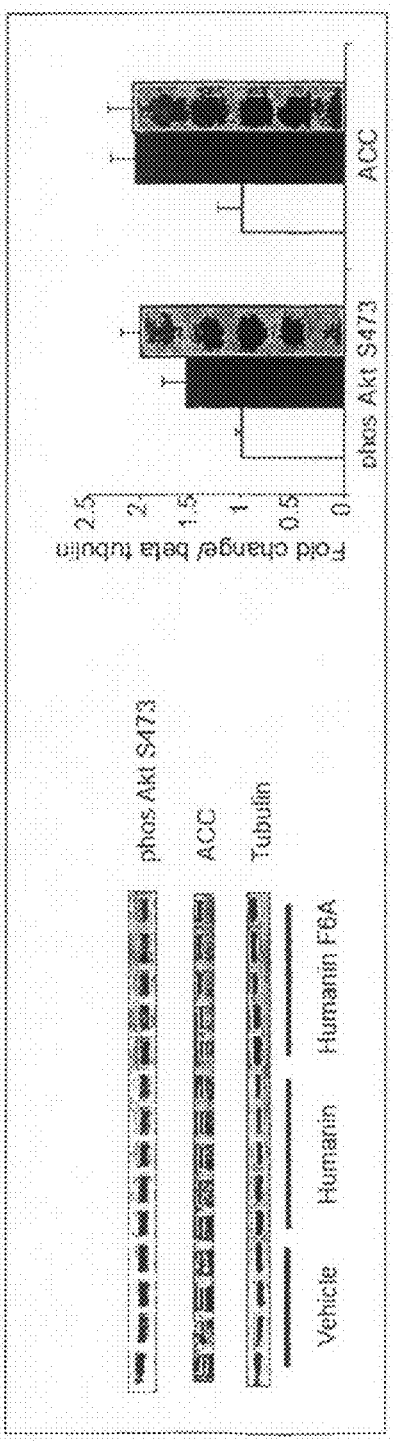
FIG. 11A-11C. Photographs of western blots and graphs showing the effects of HN and F6A HN on signaling. Three groups of rats (n=4 each) underwent clamp (as described in FIG. 6) in the presence of ICV aCSF, HN or F6A HN. Panel A-muscle was harvested immediately after the clamp studies. Phosphorylated Akt S473 and ACC protein expression was determined by Western blotting with anti-phosphorylated Akt S473 and anti-ACC antibody respectively, β-tubulin protein was used for normalization. The graph represents the fold increases in either phosphorylated Akt S473 or ACC protein over β-tubulin with expression in vehicle group taken as 1.0. For each group of columns in A: left column=vehicle, middle column=Humanin, right column=F6A. Panel B-Hypothalami was harvested immediately after the clamp studies in the groups. Phosphorylated STAT3 Y705, STAT3, phosphorylated JNK T183/Tyr185, JNK and phosphorylated AMPK T172 were quantified by western blotting and normalized to GAPDH. Panel C—An acute infusion of aCSF, HN or F6A HN (20 µg) was given ICV and hypothalami were harvested after 30 min. Phosphorylated STAT3 Y705, STAT3, phosphorylated JNK T183/Tyr185, JNK, phosphorylated P70 S6K T389 and phosphorylated AMPK T172 were quantified by western blotting and normalized to β-actin. Data are presented as fold increase, with expression in the vehicle group taken as 1.0.
Figure 11B:
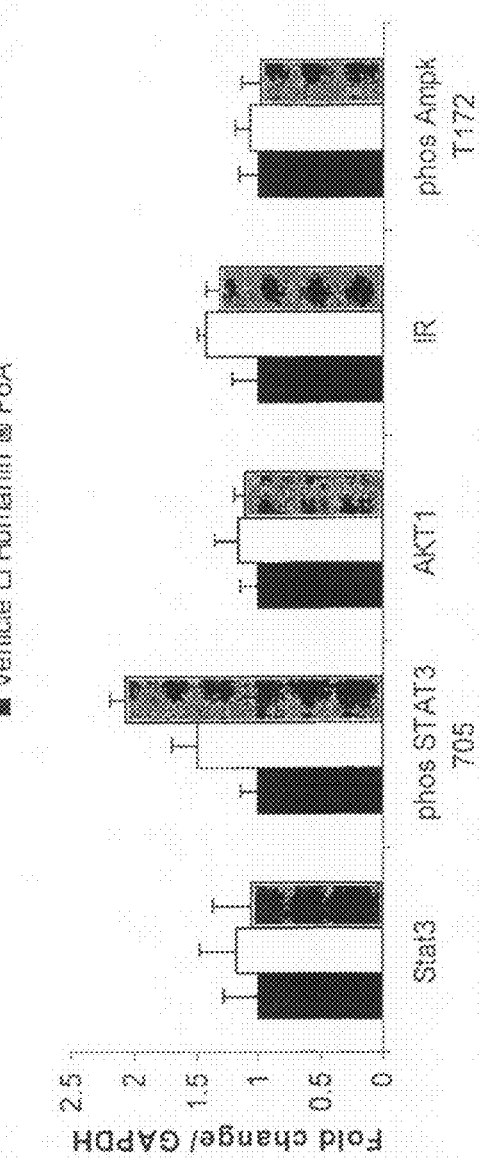
Figure 11C:
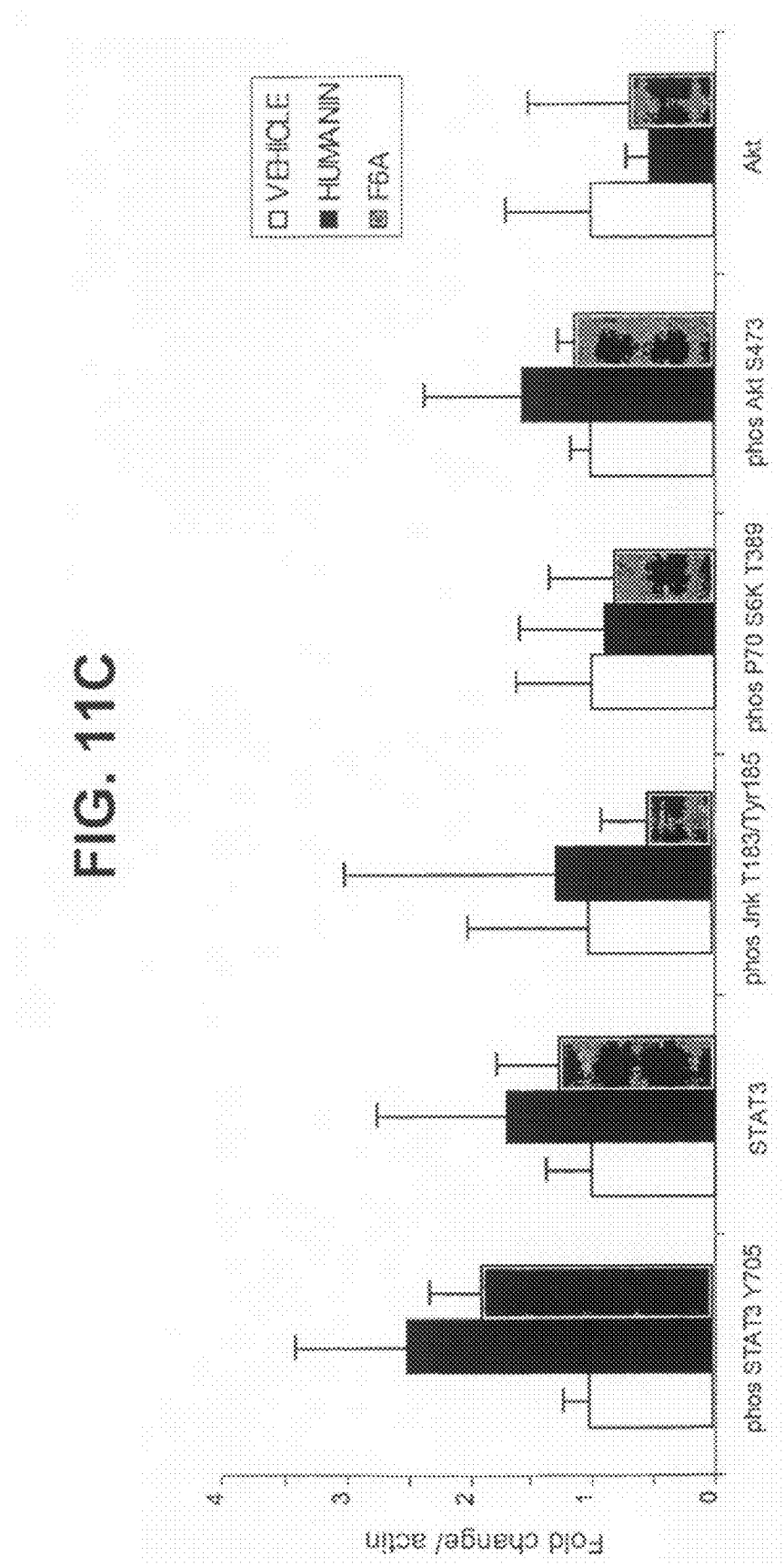

Signaling pathways. In response to ICV humanin/analogs, there is a significant increase in muscle insulin signaling as evidenced by the increase in phospho Akt. There is also significant increase in ACC in muscle, a lipogenic enzyme that is responsive to insulin (FIG. 11a). There were no changes in stat-3, phospho stat-3, GLUT 4 or muscle AMPK activity (data not shown). In the hypothalamus, in response to ICV humanin and analogs, both during the clamp and during an acute infusion, there was a modest increase in phospho STAT-3 that tended towards significance. There were no changes in the insulin receptor number, hypothalamic insulin signaling or AMPK activity (FIG. 11b, c). There were no changes in the phospho AKT, FAS, ACC, or AMPK in the liver in response to ICV infusion (data not shown).

Discussion

This work demonstrates for the first time that HN, an established neuroprotective peptide, also has favorable metabolic effects and improves overall insulin sensitivity through the hypothalamus. The expression of HN in the MBH and higher CSF levels compared to serum are consistent with the central metabolic effects seen. The critical role of mediobasal hypothalamus in mediating peripheral glucose metabolism has been unraveled by studies that show that both leptin and insulin affect hepatic insulin action through the hypothalamus (Gutierrez-Juarez, 2004; Obici et al., 2002). In fact, the effect of physiological circulating insulin on HGP is blocked in the presence of a central antagonist (Obici et al., 2002) and both leptin and insulin induce PI3 K activation in the hypothalamus The interaction between HN and IGFBP-3 is intriguing. In addition to the physical binding, HN inhibits IGFBP-3 induced activation of caspases (Ikonen et al., 2003). Studies with the F6A HN analog highlight this interaction. Inhibition of IGFBP-3 binding further enhances the insulin sensitivity of HN suggesting that endogenous IGFBP-3 in the hypothalamus (Muzubdar et al., 2004) may inhibit some of the effects of humanin on the liver. The opposing roles of these two peptides on cell survival, apoptosis and glucose metabolism are especially interesting when one considers the close relationship between insulin resistance and cell survival in AD. Both IGFBP-3 and HN are present in AD brain (Rensink et al., 2002). Defects in glucose utilization, a striking reduction in insulin receptor mRNA levels, and decrease in insulin signaling as evidenced by decreased insulin receptor substrate-1, phosphatidylinositol 3-kinase (PI3K), and phospho-Akt have been demonstrated in AD (Steen et al., 2005). On the other hand, insulin sensitizers such as thiazolinediones improve cognitive function in mouse models (Pedersen et al., 2006) as well as humans with early AD (Watson et al., 2005) highlighting the role of insulin resistance. In patients with AD, the level of humanin in CSF is decreased (unpublished data). The improvement in insulin sensitivity demonstrated with humanin can provide possible mechanisms for some of the beneficial effects demonstrated with HN in AD.

HN analogues have been shown to have unique therapeutic potential. Demonstrated here is that the F6A HN analog induces significantly more insulin sensitivity than HN. Similarly, humanin analog [Gly$^{14}$]-humanin ("S14G")(a highly potent analogue of humanin in which the serine amino acid at position 14 is replaced by glycine) is 1000 times more potent than native HN in rescue activity against memory impairment caused by AD-related insults in vivo (Tajima et al., 2005). Therefore the molecular manipulations of humanin may also prove to be of great therapeutic potential in treatment of insulin resistance.

Consistent with the increased peripheral glucose uptake in response to ICV HN, there is a significant increase in muscle phospho Akt. This is believed to be the first report of a significant increase in muscle insulin signaling as well as insulin responsive gene such as ACC in response to an ICV peptide. Unchanged hypothalamic phospho AKT demonstrates that the effects of HN are independent of hypothalamic insulin signaling. In line with in vitro studies that demonstrate that activation of STAT-3 is necessary for the neuro-protection, there is a modest increase in phospho STAT-3 in hypothalamus in response to HN. The autonomic nervous system may mediate the effects of HN on peripheral glucose metabolism similar to leptin and IGF-1 that have been shown to affect output through the sympathetic nervous system (Richards et al., 2003; Duanmu et al., 1999).

While the role of HN in cell protection, especially neuro-protection, has been substantially characterized and HN has enormous therapeutic potential for neurodegenerative diseases, the preliminary studies described here comprise the first evidence demonstrating a role for HN in glucose metabolism. The finding that HN significantly improves insulin sensitivity provides additional potential mechanisms by which HN protects against the pathological effects of AD and of the insulin resistance of aging. HN, representing a molecular link between diabetes and neuro-degeneration, may thus provide not only mechanistic explanations but also potential therapeutic options. Furthermore, specific HN analogues such as the F6A HN analog may have unique therapeutic functions and therefore, the molecular manipulations of humanin may also prove to be of great therapeutic potential in treatment of insulin resistance.

Example 3

Humanin Regulates Glucose Uptake in 3T3L1 Adipocytes

Figure 12:
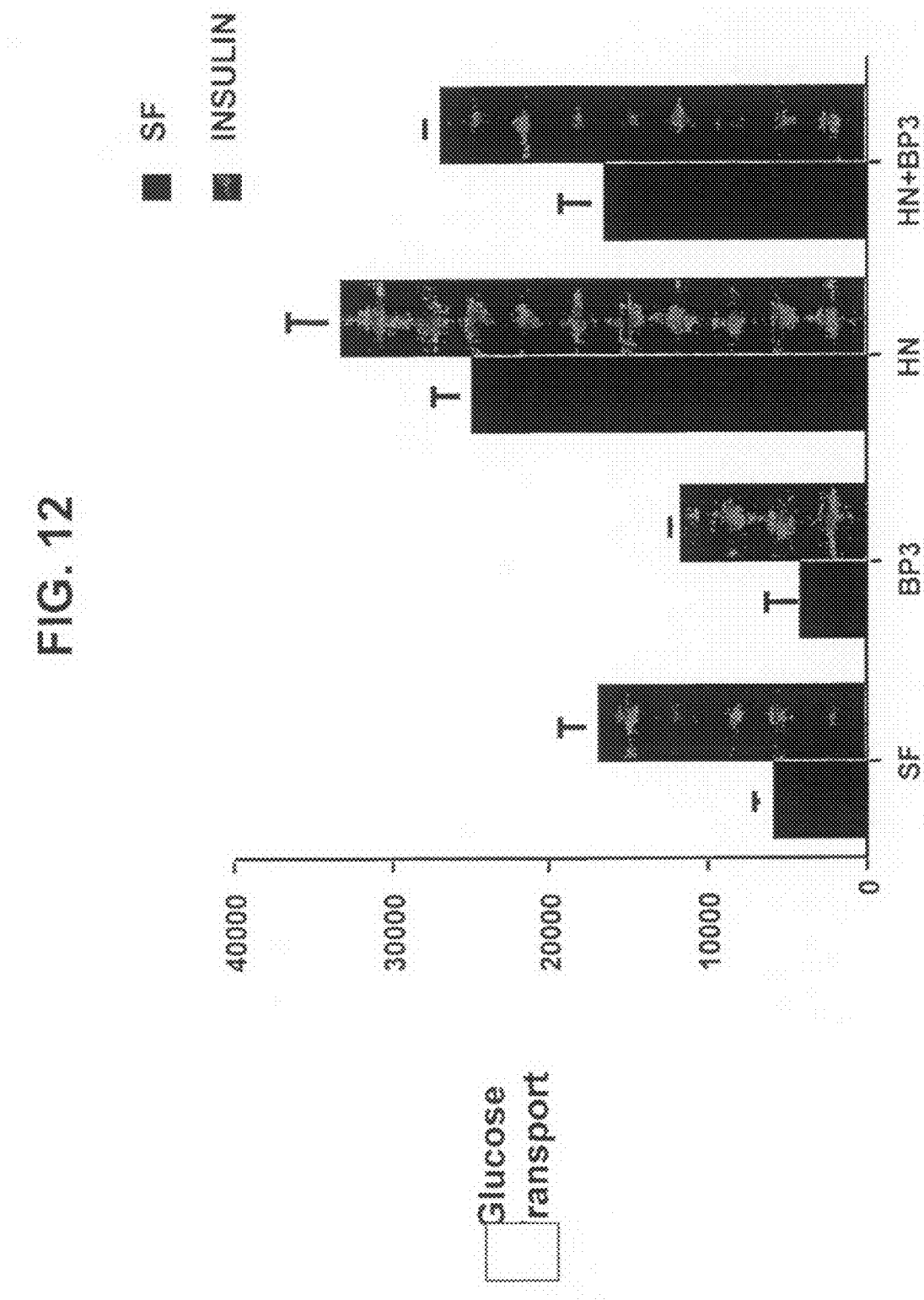
FIG. 12 is a graph showing that humanin regulates glucose uptake in 3T3L1 adipocytes. For each pair of columns: left column=SF, right column=insulin.

Using the 3T3L1 adipocyte model, the effects of humanin on insulin action and glucose transport were investigated. As shown in FIG. 12, insulin induced enhanced glucose transport and IGFBP-3 ("BP3") inhibited insulin-stimulated glucose transport in 3T3L1 cells. In the presence of humanin a significantly enhanced basal as well as insulin-stimulated glucose transport was demonstrated in both the presence and absence of IGFBP-3. This indicates that 1) humanin increases glucose utilization in peripheral tissues directly,
2) humanin enhances insulin action and acts as an insulin sensitizer in the periphery,
3) humanin antagonizes the effects of IGFBP-3 (which causes peripheral insulin resistance), and
4) these effects are in addition to the central actions of humanin where it has direct effects to lead to insulin sensitization through different mechanisms.

Example 4

Intravenous Humanin and Colivelin Enhances Hepatic Insulin Sensitivity

Figure 13:
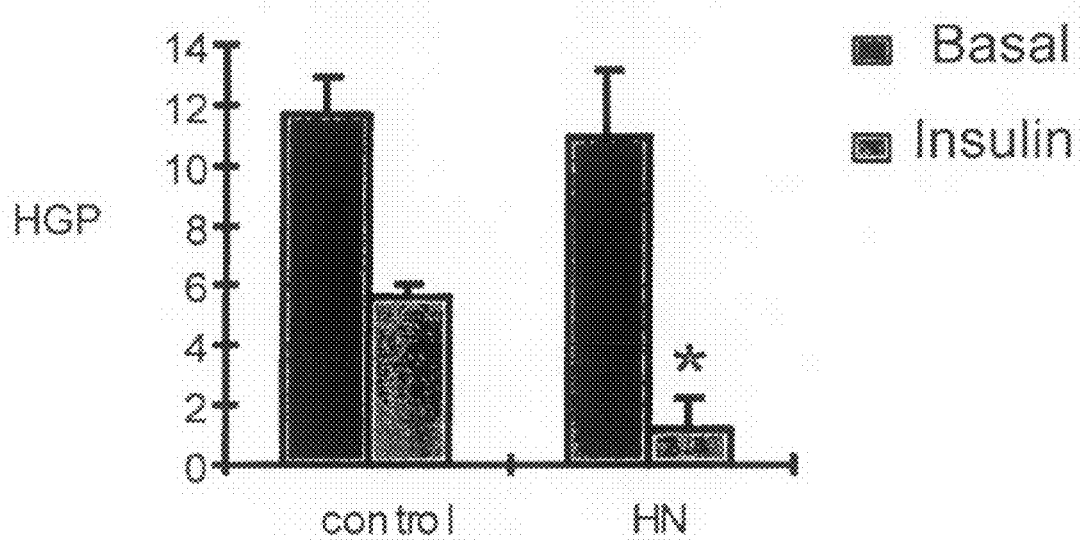
FIG. 13 is a graph showing that systemic intravenous humanin increases hepatic insulin sensitivity. For each pair of columns: left column=basal, right column=insulin.

Humanin and its analogues induce insulin sensitization via a systemic route in addition to the central effects they mediate. Systemic infusion of humanin (FIG. 13) dramatically enhances the effects of insulin on the suppression of hepatic glucose production, indicating that humanin and humanin analogues will be effective anti-diabetic agents when administered systemically.

Intravenous Colivelin enhances hepatic insulin sensitivity. To demonstrate that the above effect is shared with other analogues of humanin, colivelin was infused intravenously to rats.

Colivelin is a hybrid peptide created by attaching activity dependent neurotrophic factor (ADNF) to the C terminus of AGA-(C8R)HNG17, a potent humanin derivative (Chiba et al., 2005; Matsuoka et al., 2006). It offers greater neuroprotective ability than humanin against Alzheimer's disease and non AD related toxic agents in vitro and in vivo. Colivelin also blocks Aβ1-42 and Aβ25-35 impairment of spatial memory and suppress 3-quinuclidinyl benzilate induced memory impairment, suggesting it can pass through the blood-brain barrier.

Figure 14:
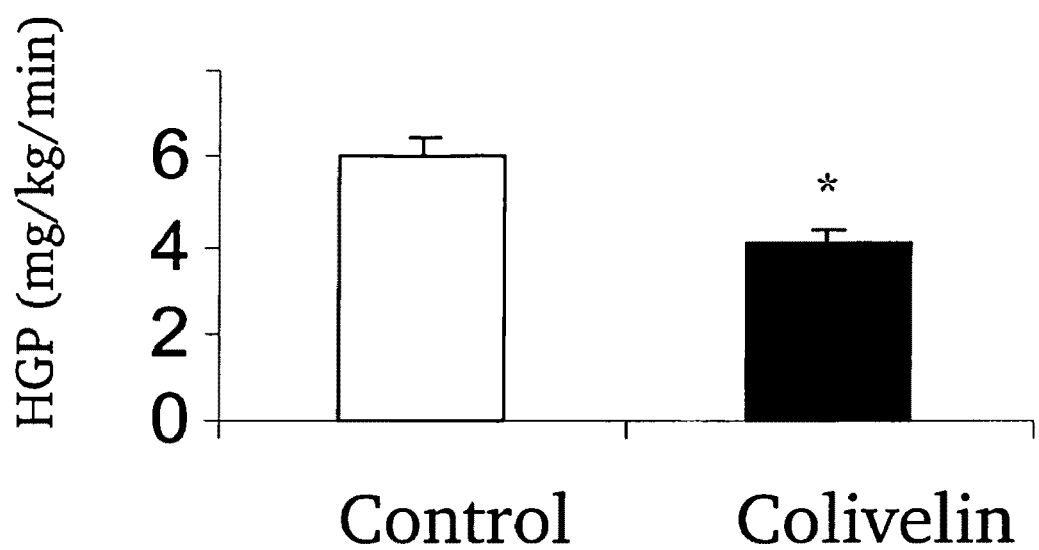
FIG. 14 is a graph showing that systemic intravenous colivelin increases hepatic insulin sensitivity.

To determine if peripheral infusion of the humanin analog colivelin affects insulin action, saline or colivelin (one hundredth of the dose of humanin) was infused intravenously during hyperinsulinemic clamp to two groups of rats that were matched for body weight (~300 gm), visceral fat (~3.5 grams), basal glucose (~135 mg % or 7 mM). Colivelin increased hepatic insulin sensitivity by 33% while peripheral glucose uptake was unchanged (FIG. 14). These studies demonstrate that in addition to humanin, synthetic analogs of humanin such as colivelin directly affect peripheral glucose metabolism at much lower doses than humanin.

Example 5

Further Studies of Humanin and its Analogs as Central Regulators of Insulin Sensitivity Materials and Methods Animal preparation for in vivo experiments: Studies were conducted with 92 three-month-old male Sprague-Dawley rats (Charles River Laboratories). Rats were housed in individual cages and subjected to a standard light-dark cycle. Rats were prepared for clamps as described in FIG. 15A. Three weeks before the in vivo studies catheters were implanted in the third cerebral ventricle (Muzumdar et al. 2003). One week before clamp experiments, catheters were placed in the right internal jugular vein and left carotid artery (Liu et al. 1998).

Figure 15A:
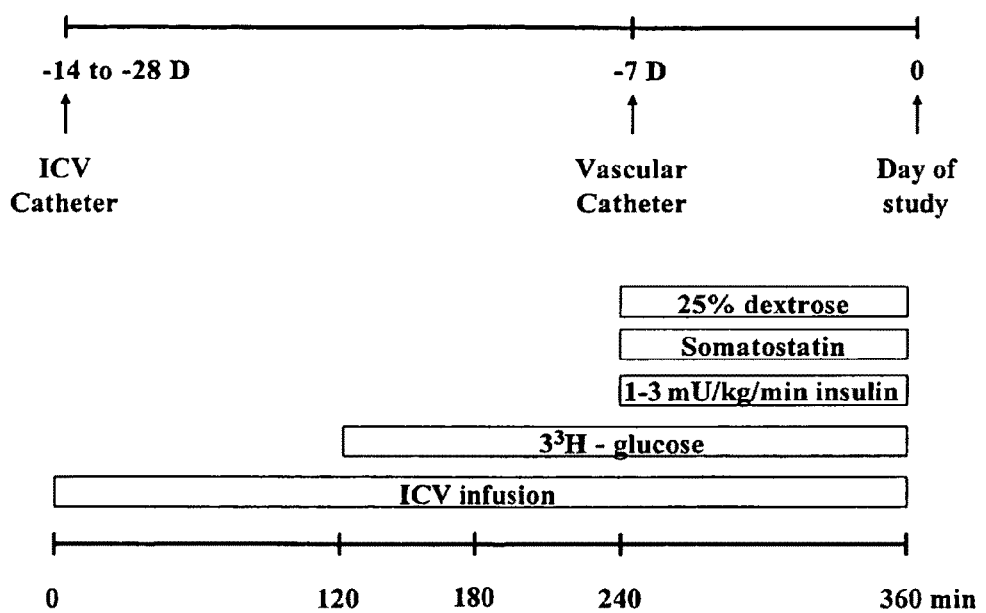

In vivo ICV and IV studies, analysis of glucose fluxes and hormone measurements: A primed-continuous ICV infusion of HN, F6A-HN (total dose of 20 µg), STAT-3 inhibitor (75 µmol) (Buettner et al. 2006), or aCSF was initiated at t=0 and maintained for the remainder of the experiment (FIG. 15A). Pancreatic insulin-clamp studies or euglycemic-hyperinsulinemic clamps were performed in conscious, unrestrained, catheterized mice for last 120 minutes as described previously (Bahar et al. 2006, Muzumdar et al. 2006). In the intra-venous group, HN, F6A, Colivelin, and HNGF6A were infused intravenously and hyperinsulinemic clamps were performed as described previously (Loeb et al. 2005). Estimation of glucose, glucose fluxes, insulin, FFA were done as described previously (Loeb et al. 2005). HN measurements were performed by an in-house, ELISA utilizing affinity purified humanin antibodies that recognize both human and rat humanin and has a limit of detection of 0.1 ng/ml (Hwang, and Cohen personal communication).

Detection of HN and IGFBP3 mRNA in hypothalamic nuclei. Total RNA was extracted from the mediobasal wedge of rat hypothalamus, and liver following Clontech's protocol. Expression of humanin and IGFBP-3 was demonstrated by RT-PCR in the hypothalamus (Muzumdar et al. 2006). The sequences for primers for humanin are F-ATGGCTAAAC-GAGGGTTCAA (SEQ ID NO:21) and R-AAGCTCCAT-AGGGTCTTCTCG (SEQ ID NO:22). The conditions for PCR were 94° C. for 10 min, cycles of 94° C. for 30 sec, then annealing temperature of 60° C. for 30 sec and then 72° C. for 1.5 minutes. The resulting PCR products were resolved on a 2% agarose gel and visualized after staining with ethidium bromide. The expected size for the PCR products is was 136-bp for humanin. PCR for IGFBP-3 was performed as described before (Muzumdar et al. 2006).

Signaling studies and Western Blots: For acute signaling studies, rats were injected ICV with either aCSF, 20 µg of HN or F6A (dissolved in aCSF) over 5 min, and sacrificed 30 min later. Tissue sample were obtained from mediobasal hypothalamus, liver and muscle. Samples were also obtained from these tissues at the end of the clamp and western blot analysis was performed as described previously (Muzumdar et al. 2003) The blots were scanned using the LI-COR Odyssey (LI-COR, Lincoln, Nebr., USA) and quantified using Odyssey 2.0 software based on direct fluorescence measurement. Dot blots were performed by blotting 50 ng of humanin, HN-analogues, and IGF on nitrocellulose, incubating with 125-I-labeled-IGFBP-3, autoradiography and scanning.

Isolation of primary hepatocytes, hepatic glucose production and signaling pathways: Single-cell suspensions of hepatocytes were obtained from perfusions of Sprague-Dawley rats using the procedure of Berry and Friend (1969) and the perfusion mixture of Leffert et al (1979). Hepatocyte glucose production was estimated after a 24 hr treatment with HN, F6A and saline as described before (Berg et al. 2001). In a separate set of experiment, hepatocytes were lysed, and protein extracted in RIPA lysis buffer at 30, 60 and 360 min post treatment with HN, F6A and saline. The cell lysates were then subject to western blotting for Phospho-STAT3 (Tyr705), total-STAT3, Phospho-AKT (Ser473), and total-AKT expression (antibodies purchased from Cell Signaling, #9131, #9132, #9271, #9272).

All values shown are expressed as means±SE. Statistical Analyses were performed using analysis of variance in multiple comparisons and unpaired, nonparametric Student's t test. When the main effect was significant, a two-tailed post hoc test (Tukey's) was applied to determine individual differences between means. A P value <0.05 was considered to be statistically significant.

The study protocol was reviewed and approved by the Institutional Animal Care and Use Committee of the Albert Einstein College of Medicine.

Results and Discussion

Figures 15C, 15D, 15E, 15F:
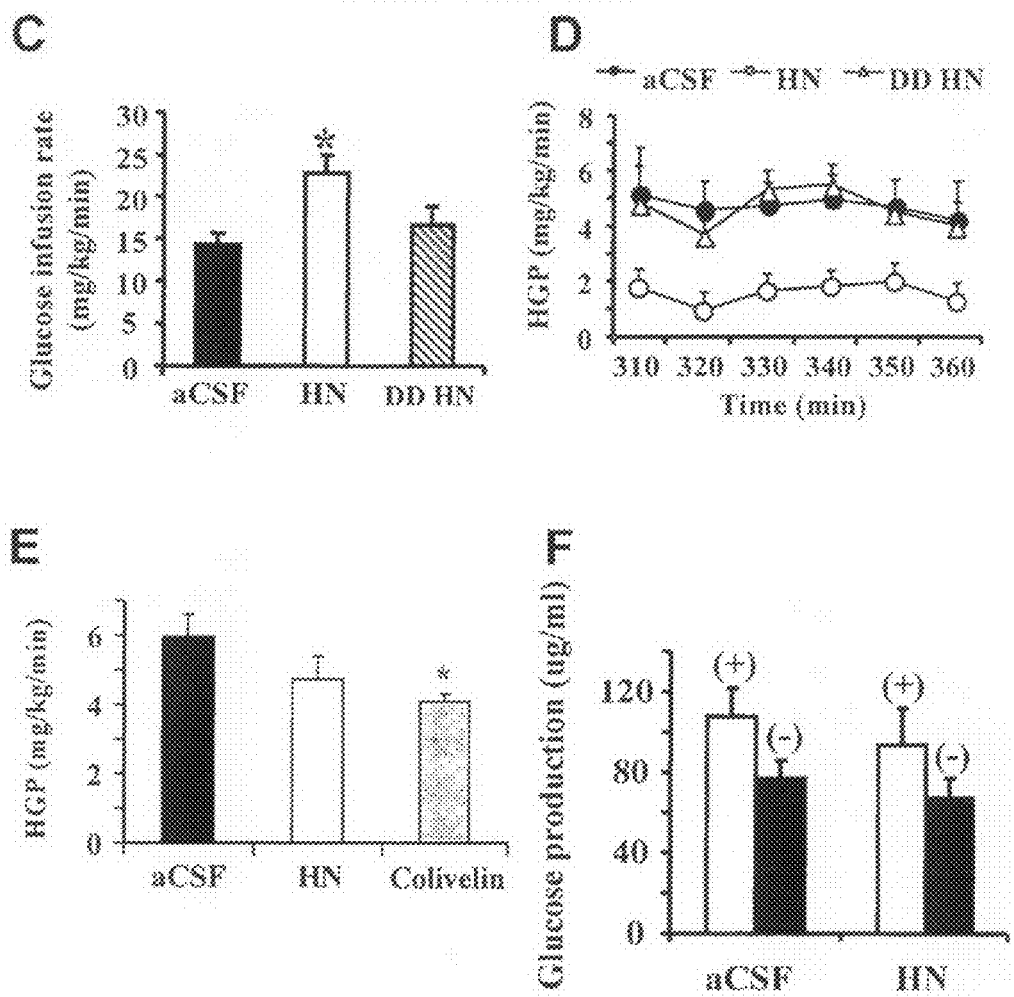

Humanin (HN) was infused at a rate of 0.1 µg/kg/min into the third cerebral ventricle (ICV) of conscious rats and glucose fluxes were studied under systemic pancreatic insulin-clamp (approximating the basal fasting state (1 mU/kg/min) with circulating insulin levels around 1.4 ng/ml) as well as during physiologic hyperinsulinemic clamp (3 mU/kg/min, corresponding to the post-prandial state with circulating insulin levels around 4.5 ng/ml) as outlined in FIG. 15A. Under both basal and high insulin levels, higher rates of glucose infusions were required to maintain euglycemia in the groups that received ICV HN. Glucose kinetics established using tracer methodology demonstrated that the need for more infused glucose to prevent hypoglycemia was due to a significant enhancement of hepatic insulin sensitivity, leading to a significant decrease in hepatic glucose output (FIG. 15B) in response to ICV HN. To demonstrate that dimerization is essential to the effects of HN (Terashita et al., 2003), a dimerization-defective HN mutant (DD-HN) was used, which is inactive on glucose metabolism (FIG. 15C) and hepatic insulin action (FIG. 15D). While the effects of HN were induced centrally, it was assessed if peripheral administration of HN can reach the hypothalamus to exert an effect that will be of clinical relevance and significance. HN was infused intravenously (at a rate of 0.375 mg/kg/hr) during a hyperinsulinemic clamp, which resulted in a trend towards decreased HGP. A highly potent analogue of HN (Colivelin) that has been shown to have an increased protective in AD and amyotrophic lateral sclerosis models (Niikura et al. 2004) at $\frac{1}{100}^{th}$ of the dose of HN (0.00375 mg/kg/hr) was then infused. This analogue demonstrated a significant further enhancement in hepatic insulin action (FIG. 15E), similar to that elicited by central infusion of HN. Notably serum concentrations of HN were 65 ng/ml during the peripheral infusion, but undetectable during ICV infusion, supporting the notion that HN action is central. A possible direct effect of HN on the liver was examined by incubating rat hepatocytes explant cultures with and without HN; glucose production rates were not different (FIG. 15F), further pinpointing that the site of action of HN is in the hypothalamus.

Figure 16A:
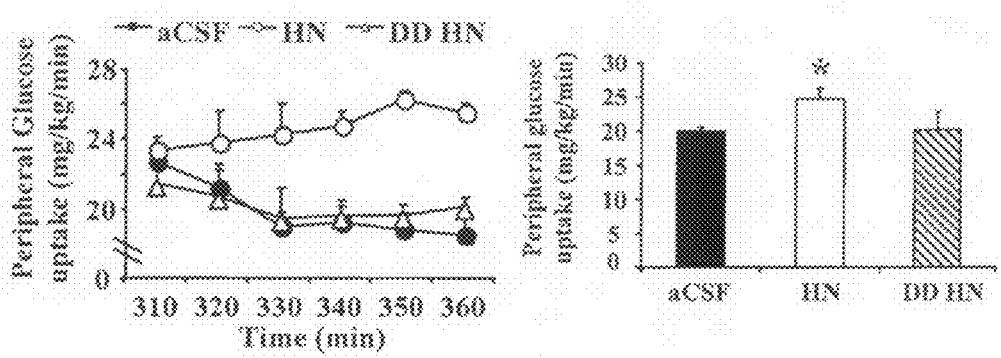
FIG. 16A-16E. HN increases peripheral insulin sensitivity. A) Effects of ICV aCSF, HN and DD-HN on peripheral glucose uptake. Effects of aCSF (black bars) and HN (white bars) on B) glycolysis, C) glycogen synthesis, and D) suppression of FFA in response to insulin. E) Phosphorylation of AKT and ACC in skeletal muscle during insulin clamp in response to ICV aCSF and HN (n=7 each). *$p<0.05$ vs controls.
Figure 16B:
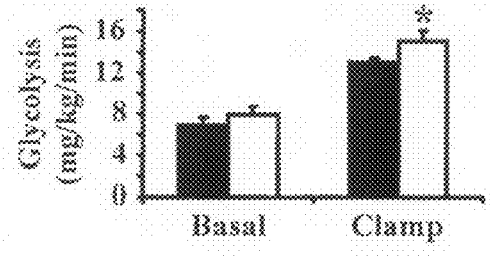
Figure 16C:
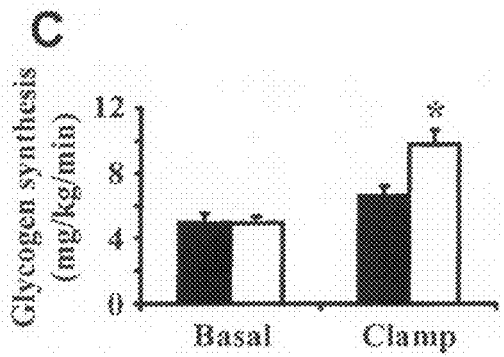
Figure 16D:
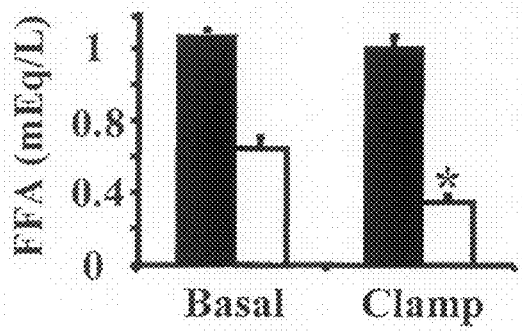
Figure 16E:
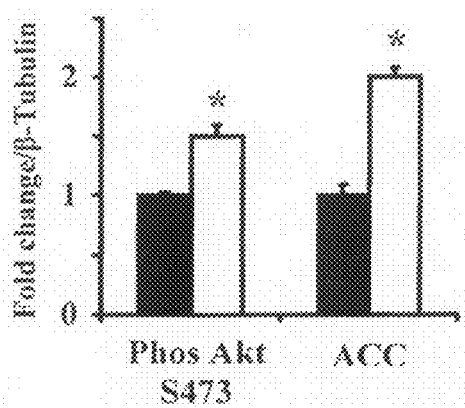

The critical role of mediobasal hypothalamus in mediating glucose metabolism has been unraveled by studies that showed that leptin, insulin, IGF-1, IGFBP-3 and other hormones affect hepatic insulin action through the hypothalamus; but so far, none of theses centrally acting peptides have been shown to have effects on peripheral glucose uptake. As shown in FIG. 16A, the dramatic increase in the glucose infusion rate with central HN is not only due to effects on HGP, but also through an increase in peripheral glucose uptake (FIG. 16B). Using tracer methodology, it was demonstrated that the HN-induced increase in glucose uptake is associated with increases in both glycolysis and glycogen synthesis (FIGS. 16C & 16D). Furthermore, insulin induced suppression of free fatty acid levels is significantly enhanced with ICV HN (FIG. 16E), reflecting an improvement in overall peripheral insulin sensitivity. Consistent with enhanced glucose uptake, under similar insulin levels, insulin signaling in the skeletal muscle was significantly increased during ICV HN infusion (FIG. 16F) as demonstrated by the enhanced activation of the phosphorylation of the insulin sensitive pAKT as well as acetyl-coA carboxylase (ACC). Thus, the central effects of HN affect blood glucose by a dual mechanism leading to both inhibition of hepatic glucose production as well as augmentation of insulin-induced peripheral glucose uptake under postprandial insulin levels. This is believed to be the first report of a significant increase in physiological insulin action on muscle metabolism and on insulin-induced molecular signaling in response to an ICV-infused peptide.

IGFBP-3 inhibits hepatic insulin action via a hypothalamic mechanism (Kim et al. 2007, Muzumdar et al. 2006) and binds HN and antagonizes its survival effects (Hashimoto et al. 2001). To assess the negative contribution that IGFBP-3 may have on HN induced insulin action, a series of HN mutants (shown in FIG. 17A) was utilized that have absent IGFBP-3 binding. RT-PCR was performed on hypothalamic mRNA, which demonstrated that both humanin and IGFBP-3 are expressed in this tissue (FIG. 17B). As demonstrated, IGFBP-3 infusion ICV led to a decrease in the peripheral glucose infusion rate, while ICV humanin increased it, as did the non-BP3-binding mutant F6A humanin (FIG. 17C). Remarkably, this analogue enhanced hepatic insulin action even more than HN. By studying glucose kinetics, it was shown that this is due to an inhibition of hepatic glucose production to almost zero (FIG. 17D) representing a ~100% suppression of hepatic glucose production (17E), effects that can not be elicited in rodents even in pharmacological levels of insulin. These studies indicate that the effects of humanin are tempered by endogenously produced IGFBP-3 in the hypothalamus and when this inhibition is prevented through the use of the non-BP3 binding F6AHN, the peptide was able to exert a more potent effect.

The opposing roles of these two peptides on apoptosis and glucose metabolism are especially interesting when one considers the close relationship between insulin resistance and cell survival in AD. Defects in glucose utilization, a striking reduction in insulin receptor mRNA levels, and decrease in insulin signaling as evidenced by decreased insulin receptor substrate-1, phosphatidylinositol 3-kinase (PI3K), and phospho-Akt have been demonstrated in AD (Li et al. 2007). On the other hand, insulin sensitizers such as thiazolinediones improve cognitive function in mouse models as well as humans with early AD highlighting the role of insulin resistance in this condition (Pedersen et al. 2006). Furthermore, IGFBP-3 production is increased in AD brain (Rensink et al. 2002) and humanin expression is present in the non-apoptotic hippocampal regions of Alzheimer's patients' brains but not in senile plaques (Tajima et al. 2002). The improvement in insulin sensitivity induced by humanin demonstrated here provides an additional mechanism for a potential beneficial effect of HN in AD.

After demonstrating the effects of systemic infusion of HN analogues on hepatic insulin sensitivity, the potential activity and mechanism of action of other carefully designed HN analogues were examined on peripheral glucose uptake. Neither HN, nor the non-BP3-binding F6AHN (at doses of 0.0375 mg/kg/hr) altered peripheral insulin action. The HN analog [Gly14]-HN (a highly potent HN analogue in which the serine amino acid at position 14 is replaced by glycine) is ~1000 times more potent than native HN in rescue activity against AD-related insults in vivo, and this potent HN analogue has recently been shown to protect in an experimental model of stroke (Xu et al. 2006). Therefore a more potent form of the non-IGFBP-3-binding-[Gly14] HN was engineered with a substitution of the 6th amino acid with alanine, termed HNGF6A. When HNGF6A was infused peripherally, (0.0375 mg/kg/hr), glucose infusion rates during clamp were significantly higher (FIG. 17F). This increase in glucose infusion rate to maintain euglycemia was due to a significant increase in peripheral glucose uptake in addition to its suppressive effects on hepatic glucose production, resulting in a dual contribution to the overall increase in end organ insulin sensitivity (FIG. 17G & FIG. 17H). This significant enhancement in insulin action by the non-BP3-binding HN analogues supports the notion that IGFBP-3 is modulator of hypothalamic HN activity.

Figures 18A, 18B:
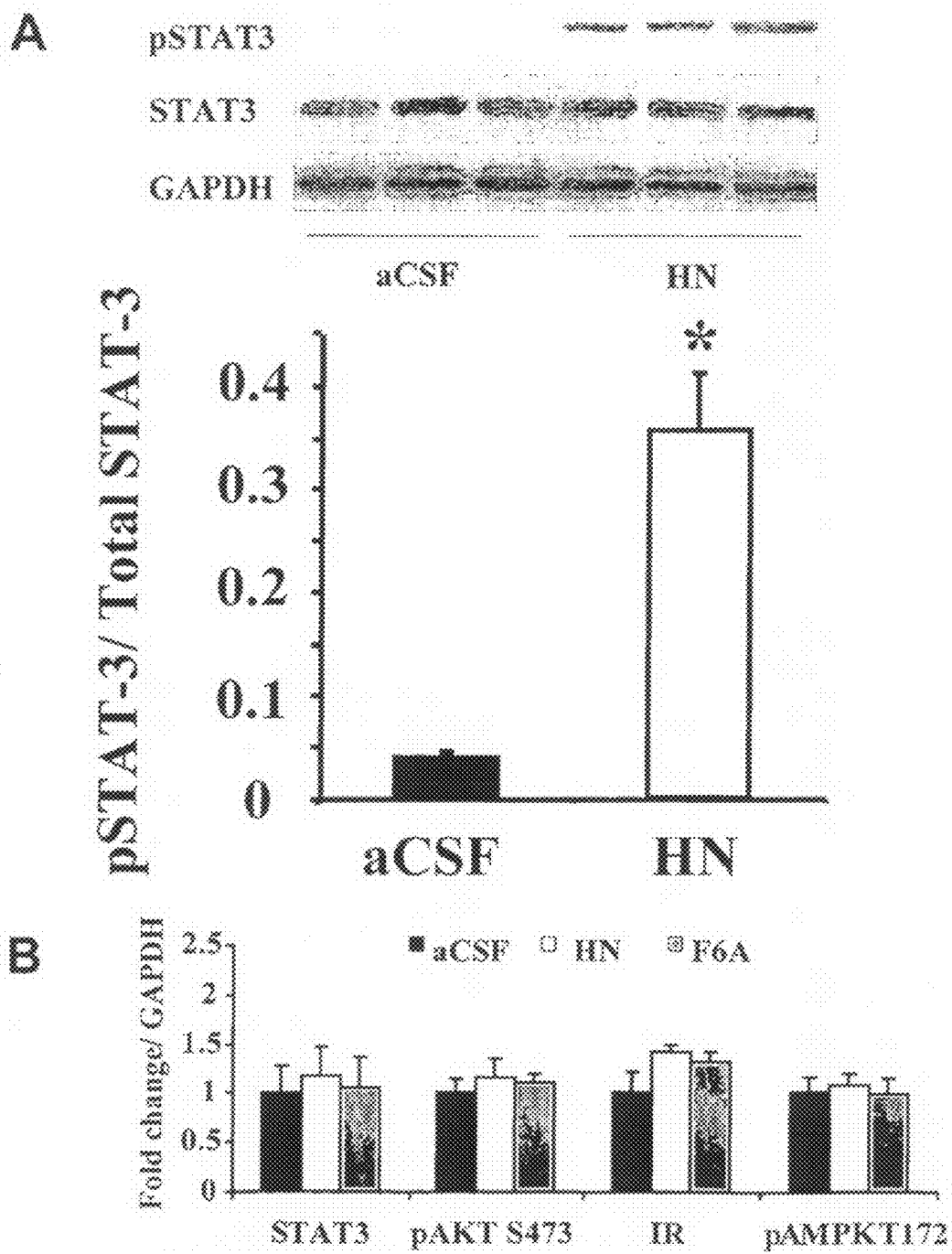
FIG. 18A-18E. Central HN effects on glucose metabolism involve hypothalamic STAT-3 activation: A) Effects of ICV HN or aCSF on pSTAT-3 in hypothalamic protein extracts. B) Effects of ICV HN on the levels of total-STAT-3, pAKT, insulin receptor (IR) and pAMPK in the hypothalamus (n=5 each). Effects of a STAT-3 inhibitor co-infused ICV with HN or aCSF (n=6 each) on C) GIR, D) peripheral glucose uptake, and E) HGP and degree of suppression of HGP. *$p<0.05$ vs controls.
Figures 18C, 18D, 18E:
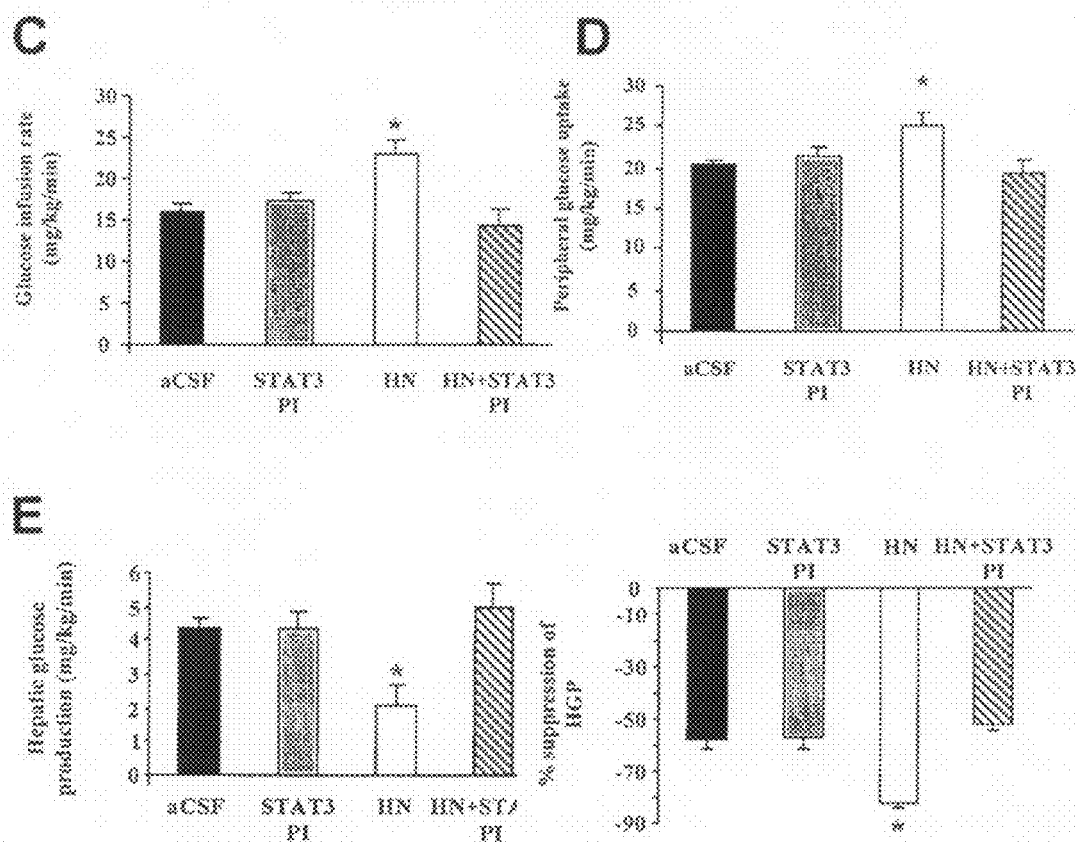

HN has been proposed to work through several mechanisms, one of which is activation of STAT-3. In line with studies that demonstrate that activation of STAT-3 is necessary for the neuro-protection (Chiba et al., 2007), a dramatic 10-fold increase in STAT-3 phosphorylation occurs in hypothalamic tissues within an hour of ICV HN infusion (FIG. 18A). Unchanged levels of phosphorylation in other signaling kinases in the hypothalamus including AKT demonstrate that the effects of HN are independent of hypothalamic insulin signaling (FIG. 18B). To test the role of STAT-3 activation in the mediation of HN actions, HN was co-infused with a STAT-3 inhibitor (Turkson et al., 2001). The effects of HN are completely attenuated in the presence of the STAT-3 inhibitor (FIG. 18C-18F). The hypothalamic delivery of the STAT-3 inhibitor showed no effect on its own, yet completely abolished HN-induced inhibition of hepatic glucose production and HN-mediated stimulation of peripheral glucose uptake. This demonstrates that the effects of HN on glucose metabolism are mediated through STAT-3 activation in the hypothalamus. Potential direct effects of HN on other signaling pathways were also studied; however, no significant differences in liver pAKT, PGC-1b, FAS, p38, CREB, ACC were demonstrable between the HN and control groups (FIG. 18E). The effects of HN were tested on primary hepatocytes including the ability of HN to induce phosphorylation of STAT-3, as hepatic STAT-3 activation has been linked to insulin action (Inoue et al. 2004). HN and F6AHN did not elicit significant changes in pAKT or pSTAT-3 in hepatocytes, compatible with the lack of effect demonstrated on hepatocyte glucose production. In muscle tissues isolated from ICV-infused rats, pAKT and acetyl CoA carboxylase were significantly increased in response to ICV HN and F6A compared to aCSF. This is consistent with the improvement in overall insulin action observed as a result of hypothalamic HN analogues. Interestingly, the nematode CNS has a central role in modulating insulin action and longevity (Alcedo et al. 2004), and future dissection of the neural pathways that mediate peripheral signals in mammalians may lead to the discovery of other regulators of metabolism and aging.

Antiapoptotic therapy for neurodegeneration has been gaining attention (Bredesen et al. 2006), and growth factors of various types have been considered, including IGF-1 and other neurosurvival peptides (Carro et al., 2002). While the role of HN in neuroprotection has been substantially characterized and HN has been proposed to have enormous therapeutic potential for neurodegenerative diseases, the studies described here comprise the first evidence demonstrating a role for HN in glucose metabolism. The current data indicates improved insulin action which central to type 2 diabetes treatment.

Age-related diseases are modulated by the interaction between the environment and the genome, and by stochastic events (Bahar et al. 2006). Our data suggests that a mitochondrial-derived molecular signal from within the CNS triggered by stochastic events can modulate disease of aging including DM2 and AD, proposed to be of mitochondrial origin (Loeb et al. 2005).

Thus, HN or its non-BP3 binding analogues may provide potential therapeutic options for prevention or treatment of at least 2 age-related diseases including impaired carbohydrate metabolism/DM2 and neuro-degeneration.

Example 6

In Vitro Studies with Humanin Analogs

Z-humanin, MAKRGLNCLPHQVSEIDLSVQKRI (SEQ ID NO:19). This peptide activates survival and STAT-3 activation as well as ERK activation in NIT cells with a two-fold greater potency than humanin.

HNGF6AK21A, MAPRGASCLLLLTGEIDLPVARRA. (SEQ ID NO:20). This peptide activates survival and STAT-3 activation as well as ERK activation in NIT with much greater potency than humanin (similar to HNGF6A).

Example 7

Properties of Humanin Analog HNGF6A (SEQ ID NO:18)

Figure 17A:
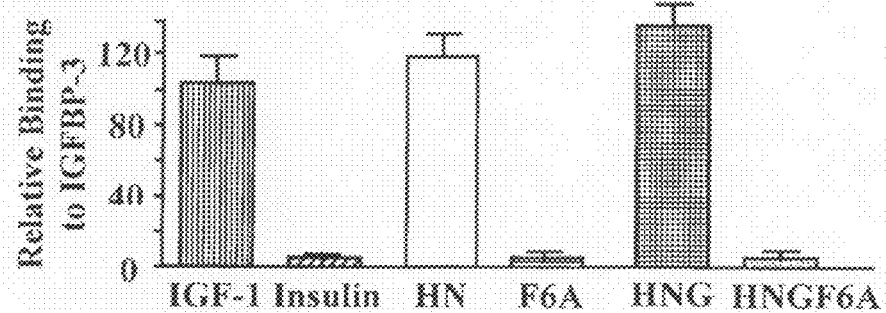
Figure 17B:
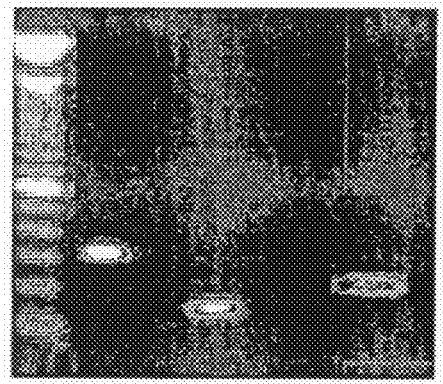
Figure 17C:
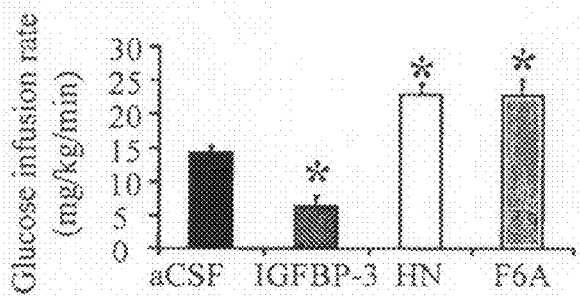

As shown in the FIG. 17A, HNGF6A is completely devoid of the ability to bind IGFBP-3 that is normally a partner of humanin.

Mouse embryonic fibroblasts derived from normal and IGFBP3 KO mice were used to test the effects of humanin and its analogues on survival. Apoptosis ELISA was used as an output measure and cells were treated for 24 hours with 100 nM of peptides. The non-BP-3 binding HNGF6A was more potent in normal MEFs; however, in BP3KO MEFs the HNG and HNGF6A had equal potency (FIG. 19), indicating that it is the loss of BP3 binding that makes HNGF6A so potent. This is important as it demonstrates that this analogue works more potently than humanin analogues that do bind IGFBP-3 and that the increased effect is a result of the loss of IGFBP-3 binding because there is no additional advantage when IGFBP-3 is not present. Thus, the HNGF6A humanin analogue has non-obvious properties that are different from previously described humanin derivatives and has increased potency as a result of its specific molecular alteration leading to reduced IGFBP-3 binding.

Example 8

HNGF6A Treats Diabetes in NONcNZO10/LtJ Mice, a Model for Obesity-Induced Type 2 Diabetes NONcNZO10/LtJ mice were injected IP with HNGF6A 25 microgram twice a day for 14 days. Mice were subjected to 6 hour fast followed by IP GTT on D15. Baseline glucose measurement was taken and the mice were injected IP with 0.5 mg/g glucose. Glucose was sampled at 0 and 90, 120 min.

Mice treated with HNGF6A displayed significantly better glucose tolerance (FIG. 20). The glucose levels at 90 and 120 min were significantly lower in the HNGF6A treated mice. Thus, HNGF6A and other humanin analogues are useful in the treatment of type 2 diabetes as well as the metabolic syndrome associated with obesity

Example 9

Humanin Levels are Related to Exceptional Longevity

Figure 21:
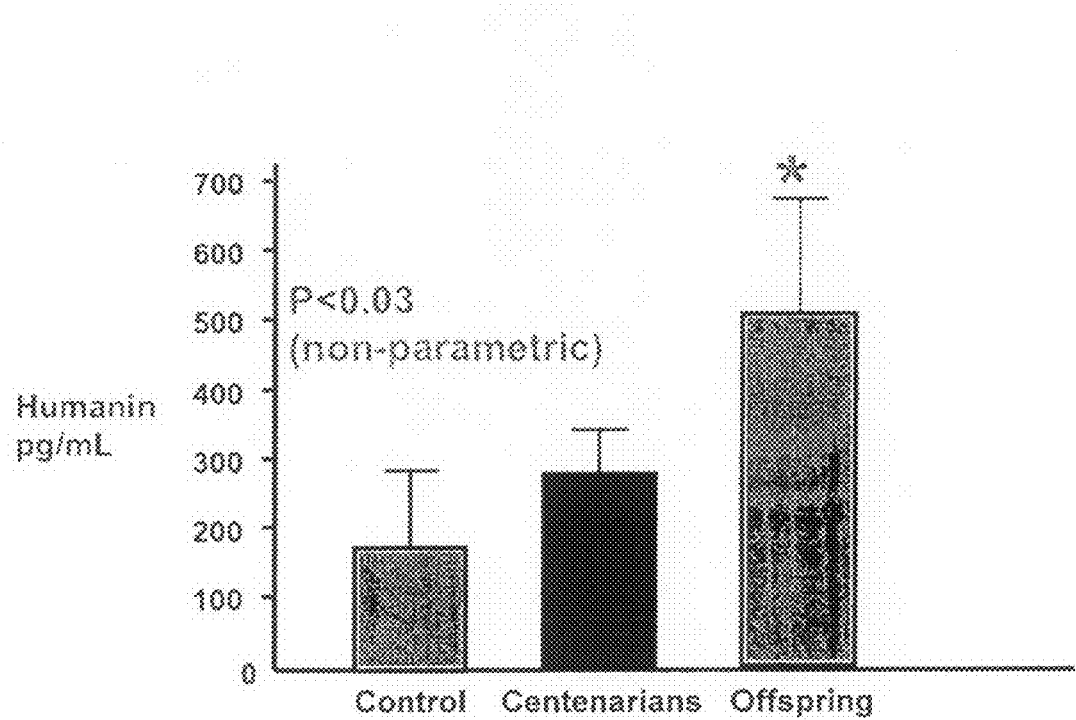
FIG. 21. Humanin levels are related to exceptional longevity. Humanin levels shown for controls (left), centenarians (middle), and offspring of centenarians (right).

The levels of humanin were examined in the plasma of subjects with extreme longevity, their offspring, and controls age-matched to the offspring. As shown in FIG. 21, extreme longevity is associated with higher levels of humanin than controls and the offspring of centenarians, who are likely to achieve extreme longevity, have dramatically higher levels. Thus, increasing the levels of humanin in a subject may increase the chances of achieving longevity.

Example 10

Humanin Analogue HNG Offers Cardio-Protection Against Ischemia-Reperfusion Injury The cardioprotective effects of a single-dose of humanin analog HNG treatment were investigated in a murine model of myocardial ischemia-reperfusion (I/R) injury. Mice were subjected to transient myocardial ischemia for a period of 45 min followed by 24 hour reperfusion. HNG (1, 5, 10, 25, 50 and 200 microgram) or vehicle (saline) was administered intraperitoneally one hour before ischemia.

Administration of HNG before ischemia decreased myocardial injury in mice as shown in FIG. 22. Reduced myocardial infarct was observed at doses of 5 μg and higher. These findings provide important information that humanin and its analogues lead to cardioprotection and could serve as a treatment for acute myocardial infarction.

REFERENCES

Alcedo J, Kenyon C. Regulation of *C. elegans* longevity by specific gustatory and olfactory neurons. Neuron. 2004; 41:45-55.

Bahar R, Hartmann C H, Rodriguez K A, Denny A D, Busuttil R A, Dolle M E, Calder R B, Chisholm G B, Pollock B H, Klein C A, Vijg J. Increased cell-to-cell variation in gene expression in ageing mouse heart. Nature. 2006; 441:1011-4.

Berg A H, Combs T P, Du X, Brownlee M, Scherer P E. The adipocyte-secreted protein Acrp30 enhances hepatic insulin action. Nat Med. 2001; 7:947-53.

Berry, M. N. & Friend, B. S. High-yield preparation of isolated rat liver parenchymal cells: a biochemical and fine structure study. J. Cell. Biol. 1969; 43, 506-520.

Bilan P J, Mitsumoto Y, Ramlal T, Klip A: Acute and long-term effects of insulin-like growth factor I on glucose transporters in muscle cells: translocation and biosynthesis. FEBS Lett 298:285-290, 1992.

Binoux M: The IGF system in metabolism regulation. Diabete Metab 21:330-337, 1995.

Bredesen D E, Rao R V, Mehlen P. Cell death in the nervous system. Nature. 2006; 443:796-802.

Buettner C, Patel R, Muse E D, Bhanot S, Monia B P, McKay R, Obici S, Rossetti L: Severe impairment in liver insulin signaling fails to alter hepatic insulin action in conscious mice. J Clin Invest 115:1306-1313, 2005.

Buettner C, Pocai A, Muse E D, Etgen A M, Myers M G Jr, Rossetti L. Critical role of STAT3 in leptin's metabolic actions. Cell Metab. 2006; 4:49-60.

Bunn R C, King W D, Winkler M K, Fowlkes J L: Early developmental changes in IGF-I, IGF-II, IGF binding protein-1, and IGF binding protein-3 concentration in the cerebrospinal fluid of children. Pediatr Res 58:89-93, 2005.

Butt A J, Fraley K A, Firth S M, Baxter R C: IGF-binding protein-3-induced growth inhibition and apoptosis do not require cell surface binding and nuclear translocation in human breast cancer cells. Endocrinology 143:2693-2699, 2002.

Carro E, Trejo J L, Gomez-Isla T, LeRoith D, Torres-Aleman I. Serum insulin-like growth factor I regulates brain amyloid-beta levels. Nat Med. 2002; 8:1390-7.

Carroll P V, Christ E R, Umpleby A M, Gowrie I, Jackson N, Bowes S B, Hovorka R, Croos P, Sonksen P H, Russell-Jones D L: IGF-I treatment in adults with type 1 diabetes: effects on glucose and protein metabolism in the fasting state and during a hyperinsulinemic-euglycemic amino acid clamp. Diabetes 49:789-796, 2000.

Chan S S, Twigg S M, Firth S M, Baxter R C: Insulin-like growth factor binding protein-3 leads to insulin resistance in adipocytes. J Clin Endocrinol Metab 90:6588-6595, 2005.

Chiba T, Nishimoto I, Aiso S, Matsuoka M. Neuroprotection against neurodegenerative diseases: development of a novel hybrid neuroprotective peptide Colivelin. Mol Neurobiol. 2007; 35:55-84.

Chiva, T et al.: Development of a femtomolar-acting humanin derivative named colivelin by attaching activity-dependent neurotrophic factor to its N terminus: Characterization of colivelin-mediated neuroprotection against Alzheimer's disease-relevant insults in vitro and in vivo. J Neurosci 25:10252-10261, 2005.

Craft S. Resistance syndrome and Alzheimer's disease: age- and obesity-related effects on memory, amyloid, and inflammation. Neurobiol Aging. 2005; 26 Suppl 1:65-9.

Cutfield W S, Wilton P, Bennmarker H, Albertsson-Wikland K, Chatelain P, Ranke M B, Price D A: Incidence of diabetes mellitus and impaired glucose tolerance in children and adolescents receiving growth-hormone treatment. Lancet 355:610-613, 2000.

Dello Russo C, Gavrilyuk V, Weinberg G, Almeida A, Bolanos J P, Palmer J, Pelligrino D, Galea E, Feinstein D L: Peroxisome proliferator-activated receptor gamma thiazolidinedione agonists increase glucose metabolism in astrocytes. J Biol Chem 278:5828-5836, 2003.

Duanmu Z, Scislo T, Dunbar J C: Glycemic modulation of insulin/IGF-1 mediated skeletal muscle blood following sympathetic denervation in normal rats. Clin Exp Hypertens 21:1239-1255, 1999.

Executive Summary of The Third Report of The National Cholesterol Education Program (NCEP) Expert Panel on Detection, Evaluation, And Treatment of High Blood Cholesterol In Adults (Adult Treatment Panel III) JAMA 2001; 16:285:2486-97.

Fernandez-Galaz M C, Naftolin F, Garcia-Segura LM: Phasic synaptic remodeling of the rat arcuate nucleus during the estrous cycle depends on insulin-like growth factor-I receptor activation. J Neurosci Res 55:286-292, 1999.

Franklin S L, Ferry R J Jr, Cohen P: Rapid insulin-like growth factor (IGF)-independent effects of IGF binding protein-3 on endothelial cell survival. J Clin Endocrinol Metab 88:900-907, 2003.

Frick F, Oscarsson J, Vikman-Adolfsson K, Ottosson M, Yoshida N, Eden S: Different effects of IGF-I on insulin-stimulated glucose uptake in adipose tissue and skeletal muscle. Am J Physiol Endocrinol Metab 278:E729E737, 2000.

Garcia-Segura LM, Rodriguez JR, Torres-Aleman I: Localization of the insulin-like growth factor I receptor in the cerebellum and hypothalamus of adult rats: an electron microscopic study. J Neurocytol 26:479-490, 1997.

Guo B, Zhai D, Cabezas E, Welsh K, Nouraini S, Satterthwait A C, Reed J C: Humanin peptide suppresses apoptosis by interfering with Bax activation. Nature 423:456-461, 2003.

Gutierrez-Juarez R, Obici S, Rossetti L: Melanocortin-independent effects of leptin on hepatic glucose fluxes. J Biol Chem 279:49704-49715, 2004.

Halaas J L, Gajiwala K S, Maffei M, Cohen S L, Chait B T, Rabinowitz D, Lallone R L, Burley S K, Friedman J M: Weight-reducing effects of the plasma protein encoded by the obese gene. Science 269:543-546, 1995.

Harel Z, Tannenbaum GS: Synergistic interaction between insulin-like growth factors-I and -II in central regulation of pulsatile growth hormone secretion. Endocrinology 131: 758-764, 1992.

Hashimoto Y, Niikura T, Tajima H, Yasukawa T, Sudo H, Ito Y, Kita Y, Kawasumi M, Kouyama K, Doyu M, Sobue G, Koide T, Tsuji S, Lang J, Kurokawa K, Nishimoto I: A rescue factor abolishing neuronal cell death by a wide spectrum of familial Alzheimer's disease genes and Abeta. Proc Natl Acad Sci USA 98:6336-6341, 2001.

Huang S S, Ling T Y, Tseng W F, Huang Y H, Tang F M, Leal S M, Huang J S: Cellular growth inhibition by IGFBP-3 and TGF-beta1 requires LRP-1. FASEB J 17:2068-81, 2003.

Ikonen M, Liu B, Hashimoto Y, Ma L, Lee K W, Niikura T, Nishimoto I, Cohen P: Interaction between the Alzheimer's survival peptide humanin and insulin-like growth factor-binding protein 3 regulates cell survival and apoptosis. Proc Natl Acad Sci USA 100:13042-13047, 2003.

Ikezoe T, Tanosaki S, Krug U, Liu B, Cohen P, Taguchi H, Koeffler HP: Insulin-like growth factor binding protein-3 antagonizes the effects of retinoids in myeloid leukemia cells. Blood 104:237-242, 2004.

Inoue H, Ogawa W, Ozaki M, Haga S, Matsumoto M, Furukawa K, Hashimoto N, Kido Y, Mori T, Sakaue H, Teshigawara K, Jin S, Iguchi H, Hiramatsu R, LeRoith D, Takeda K, Akira S, Kasuga M. Role of STAT-3 in regulation of hepatic gluconeogenic genes and carbohydrate metabolism in vivo. Nat Med. 2004; 10:168-74.

Jung S S, Van Nostrand W E: Humanin rescues human cerebrovascular smooth muscle cells from Abeta-induced toxicity. J Neurochem 84:266-272, 2003.

Kariya S, Takahashi N, Ooba N, Kawahara M, Nakayama H, Ueno S: Humanin inhibits cell death of serum-deprived PC12h cells. Neuroreport 13:903-907, 2002.

Kariya S, Takahashi N, Hirano M, Ueno S: Humanin improves impaired metabolic activity and prolongs survival of serum-deprived human lymphocytes. Mol Cell Biochem 254:83-89, 2003.

Kim, Ali O, Shim M, Lee K W, Vuguin P, Muzumdar R, Barzilai N, P C: Insulin like growth factor −3 induces insulin resistance in adipocytes in vitro and in rats in vivo. Pediatric Research 61:159-164, 2007.

Kovacs P, Parlow A F, Karkanias G B: Effect of centrally administered insulin on gonadotropin-releasing hormone neuron activity and luteinizing hormone surge in the diabetic female rat. Neuroendocrinology 76:357-365, 2002.

Lee K W, Cohen P: Nuclear effects: unexpected intracellular actions of insulin-like growth factor binding protein-3. J Endocrinol 175:33-40, 2002.

Lee K W, Liu B, Ma L, Li H, Bang P, Koeffler H P, Cohen P: Cellular internalization of insulin-like growth factor binding protein-3: distinct endocytic pathways facilitate re-uptake and nuclear localization. J Biol Chem 279:469-476, 2004.

Leffert, H. L., Koch, K. S., Moran, T. & Williams, M. Liver cells. Methods Enzymol. 1979; 58, 536-544.

Li Z G, Zhang W, Sima A A. Alzheimer-like changes in rat models of spontaneous diabetes. Diabetes. 2007; 56:1817-24.

Liu L, Karkanias G B, Morales J C, Hawkins M, Barzilai N, Wang J, Rossetti L: Intracerebroventricular leptin regulates hepatic but not peripheral glucose fluxes. J Biol Chem 273:31160-31167, 1998.

Liu B, Lee H Y, Weinzimer S A, Powell D R, Clifford J L, Kurie J M, Cohen P: Direct functional interactions between insulin-like growth factor-binding protein-3 and retinoid X receptor-alpha regulate transcriptional signaling and apoptosis. J Biol Chem 275:33607-33613, 2000.

Liu B, Weinzimer S A, Gibson T B, Mascarenhas D, Cohen P: Type Ialpha collagen is an IGFBP-3 binding protein. Growth Horm IGF Res 13:89-97, 2003.

Loeb L A, Wallace D C, Martin G M. The mitochondrial theory of aging and its relationship to reactive oxygen species damage and somatic mtDNA mutations. Proc Natl Acad Sci USA. 2005; 102:18769-70.

Lofqvist C, Andersson E, Gelander L, Rosberg S, Hulthen L, Blum W F, Wikland K A: Reference values for insulin-like growth factor-binding protein-3 (IGFBP-3) and the ratio of insulin-like growth factor-I to IGFBP-3 throughout childhood and adolescence. J Clin Endocrinol Metab 90:1420-1427, 2005.

Maher F, Clark S, Harrison L C: Chronic stimulation of glucose transporter gene expression in L6 myocytes mediated via the insulin-like growth factor-1 receptor. Mol Endocrinol 3:2128-2135, 1989.

Mamiya T, Ukai M: [Gly(14)]-Humanin improved the learning and memory impairment induced by scopolamine in vivo. Br J Pharmacol 134:1597-1599, 2001.

Matsuoka M et al.: Humanin and colivelin: Neuronal-death-suppressing peptides for Alzheimer's disease and amyotrophic lateral sclerosis. CNS Drug Reviews 12:113-122, 2006.

Munzer T, Rosen C J, Harman S M, Pabst K M, Clair C S, Sorkin J D, Blackman M R: Effects of GH and/or sex steroids on circulating IGF-I and IGFBPs in healthy, aged women and men. Am J Physiol Endocrinol Metab 290:E1006E1013, 2006.

Muse E D, Lam T K, Scherer P E, Rossetti L. Hypothalamic resistin induces hepatic insulin resistance. J Clin Invest. 2007; 117:1670-8.

Muzumdar R, Ma X, Yang X, Atzmon G, Bernstein J, Karkanias G, Barzilai N: Physiologic effect of leptin on insulin secretion is mediated mainly through central mechanisms. FASEB J 17:1130-1132, 2003.

Muzumdar R, Ma X, Fishman S, Yang X, Atzmon G, Vuguin P, Einstein F, Hwang D, Cohen P, Barzilai N: Central and Opposing effects of IGF-1 and IGFBP-3 on systemic insulin action. Diabetes 55:2788-2796, 2006.

Nagaraja T N, Patel P, Gorski M, Gorevic P D, Patlak C S, Fenstermacher J D: In normal rat, intraventricularly administered insulin-like growth factor-1 is rapidly cleared from CSF with limited distribution into brain. Cerebrospinal Fluid Res 2:5, 2005.

Niblock M M, Brunso-Bechtold J K, Lynch C D, Ingram R L, McShane T, Sonntag W E: Distribution and levels of insulin-like growth factor I mRNA across the life span in the Brown Norway x Fischer 344 rat brain. Brain Res 804:79-86, 1998.

Niikura T, Chiba T, Aiso S, Matsuoka M, Nishimoto I. Humanin: after the discovery. Mol Neurobiol. 2004; 30:327-40.

Obici S, Zhang BB, Karkanias G, Rossetti L: Hypothalamic insulin signaling is required for inhibition of glucose production. Nat Med 8:1376-1382, 2002.

O'Connell T, Clemmons DR: IGF-I/IGF-binding protein-3 combination improves insulin resistance by GH-dependent and independent mechanisms. J Clin Endocrinol Metab 87:4356-4360, 2002.

Ocrant I, Fay C T, Parmelee J T: Characterization of insulin-like growth factor binding proteins produced in the rat central nervous system. Endocrinology 127:1260-1267, 1990.

Oufattole M, Lin S W, Liu B, Mascarenhas D, Cohen P, Rodgers BD: Ribonucleic acid polymerase II binding subunit 3 (Rpb3), a potential nuclear target of insulin-like growth factor binding protein-3. Endocrinology 147:2138-2146, 2006.

Pan W, Kastin A J: Interactions of IGF-I with the blood-brain barrier in vivo and in situ. Neuroendocrinology 72:171-178, 2000.

Pedersen W A, McMillan P J, Kulstad J J, Leverenz J B, Craft S, Haynatzki G R: Rosiglitazone attenuates learning and memory deficits in Tg2576 Alzheimer mice. Exp Neurol 199:265-273, 2006.

Rajah R, Valentinis B, Cohen P: Insulin-like growth factor (IGF)-binding protein-3 induces apoptosis and mediates the effects of transforming growth factor-beta1 on programmed cell death through a p53- and IGF-independent mechanism. J Biol Chem 272:12181-12188, 1997.

Rensink A A, Gellekink H, Otte-Holler I, ten Donkelaar H J, de Waal R M, Verbeek M M, Kremer B: Expression of the cytokine leukemia inhibitory factor and pro-apoptotic insulin-like growth factor binding protein-3 in Alzheimer's disease. Acta Neuropathol (Berl) 104:525-533, 2002.

Richards R J, Blalock A, Liao J, Reisin E: Leptin: sympathetic and cardiovascular effects. Curr Cardiol Rep 5:453-458, 2003.

Ricort J M, Binoux M: Insulin-like growth factor-binding protein-3 activates a phosphotyrosine phosphatase: effects on the insulin-like growth factor signaling pathway. J Biol Chem 277:19448-19454, 2002.

Rossetti L, Giaccari A: Relative contribution of glycogen synthesis and glycolysis to insulin-mediated glucose uptake: a dose-response euglycemic clamp study in normal and diabetic rats. J Clin Invest 85:1785-1792, 1990.

Sandhu M S, Heald A H, Gibson J M, Cruickshank J K, Dunger D B, Wareham N J: Circulating concentrations of insulin-like growth factor-I and development of glucose intolerance: a prospective observational study. Lancet 359:1740-1745, 2002.

Schedlich L J, Le Page S L, Firth S M, Briggs L J, Jans D A, Baxter R C: Nuclear import of insulin-like growth factor-binding protein-3 and -5 is mediated by the importin beta subunit. J Biol Chem 275:23462-23470, 2000.

Sherwin R S, Borg W P, Boulware S D: Metabolic effects of insulin-like growth factor I in normal humans. Horm Res 41 (Suppl. 2):97-101, 1994.

Shim M, Vuguin P, Mascarenhas D, Barzilai N, Cohen P: IGFBP-3 induces insulin resistance and mediated TNF-alpha in adipocytes. Poster presented at the Pediatric Endocrinology meeting, 6-10 Jul. 2001, Montreal Silha J V, Gui Y, Murphy L J: Impaired glucose homeostasis in insulin-like growth factor-binding protein-3-transgenic mice. Am J Physiol Endocrinol Metab 283:E937E945, 2002.

Simpson H L, Jackson N C, Shojaee-Moradie F, Jones R H, Russell-Jones D L, Sonksen P H, Dunger D B, Umpleby A M: Insulin-like growth factor I has a direct effect on glucose and protein metabolism, but no effect on lipid metabolism in type 1 diabetes. J Clin Endocrinol Metab 89:425-432, 2004.

Sonntag W E, Lynch C D, Bennett S A, Khan A S, Thornton P L, Cooney P T, Ingram R L, McShane T, Brunso-Bechtold J K: Alterations in insulin-like growth factor-1 gene and protein expression and type 1 insulin-like growth factor receptors in the brains of ageing rats. Neuroscience 88:269-279, 1999.

Sponne I, Fifre A, Koziel V, Kriem B, Oster T, Pillot T: Humanin rescues cortical neurons from prion-peptide-induced apoptosis. Mol Cell Neurosci 25:95-102, 2004.

Steen E, Terry B M, Rivera E J, Cannon J L, Neely T R, Tavares R, Xu Xi, Wands J R, de la Monte S M: Impaired insulin and insulin-like growth factor expression and signaling mechanisms in Alzheimer's disease—is this type 3 diabetes? J Alzheimers Dis 7:63-80, 2005.

Tajima H, Niikura T, Hashimoto Y, Ito Y, Kita Y, Terashita K, Yamazaki K, Koto A, Aiso S, Nishimoto I: Evidence for in vivo production of Humanin peptide, a neuroprotective factor against Alzheimer's disease-related insults. Neurosci Lett 324:227-231, 2002.

Terashita K, Hashimoto Y, Niikura T, Tajima H, Yamagishi Y, Ishizaka M, Kawasumi M, Chiba T, Kanekura K, Yamada M, Nawa M, Kita Y, Aiso S, Nishimoto I. Two serine residues distinctly regulate the rescue function of Humanin, an inhibiting factor of Alzheimer's disease-related neurotoxicity: functional potentiation by isomerization and dimerization. J. Neurochem. 2003; 85:1521-38.

Turkson J, Ryan D, Kim J S, Zhang Y, Chen Z, Haura E, Laudano A, Sebti S, Hamilton A D, Jove R. Phosphotyrosyl peptides block Stat3-mediated DNA binding activity, gene regulation, and cell transformation. J Biol Chem. 2001; 276:45443-55.

Wass J A, Clemmons D R, Underwood L E, Barrow I, Besser G M, Van Wyk J J: Changes in circulating somatomedin-C levels in bromocriptine-treated acromegaly. Clin Endocrinol (Oxf) 17:369-377, 1982.

Watson G S, Cholerton B A, Reger M A, Baker L D, Plymate S R, Asthana S, Fishel M A, Kulstad J J, Green P S, Cook D G, Kahn S E, Keeling M L, Craft S: Preserved cognition in patients with early Alzheimer disease and amnestic mild cognitive impairment during treatment with rosiglitazone: a preliminary study. Am J Geriatr Psychiatry 13:950-958, 2005.

Weinzimer S A, Gibson T B, Collett-Solberg P F, Khare A, Liu B, Cohen P: Transferrin is an insulin-like growth factor-binding protein-3 binding protein. J Clin Endocrinol Metab 86:1806-1813, 2001.

Xu X, Chua C C, Gao J, Hamdy R C, Chua B H. Humanin is a novel neuroprotective agent against stroke. Stroke. 2006; 37:2613-9.

Yakar S, Liu J L, Fernandez A M, Wu Y, Schally A V, Frystyk J, Chernausek S D, Mejia W, Le Roith D: Liver-specific IGF-I gene deletion leads to muscle insulin insensitivity. Diabetes 50:1110-1118, 2001.

Yakar S, Setser J, Zhao H, Stannard B, Haluzik M, Glatt V, Bouxsein M L, Kopchick J J, LeRoith D: Inhibition of growth hormone action improves insulin sensitivity in liver IGF-I-deficient mice. J Clin Invest 113:96-105, 2004.

Ying G, Iribarren P, Zhou Y, Gong W, Zhang N, Yu Z X, Le Y, Cui Y, Wang J M. Humanin, a newly identified neuroprotective factor, uses the G protein-coupled formylpeptide receptor-like-1 as a functional receptor. J. Immunol. 2004; 172:7078-85.

U.S. Pat. No. 7,053,053, issued May 30, 2006, Sugo et al., Humanin-like peptide and use thereof.

SEQ ID NOs

```
                                            SEQ ID NO: 1
Human humanin amino acid sequence, GenBank
AAK50430
maprgfscll lltseidlpv krra SEQ ID NO: 2
Humanin-like peptide from U.S Pat. No. 7,053,053
amino acid sequence
marrgfscll lsttatdlpv krrt SEQ ID NO: 3
Humanin analog F6A amino acid sequence
maprgascll lltseidlpv krra SEQ ID NO: 4
Humanin analog S14G (HNG) amino acid sequence
maprgfscll lltgeidlpv krra SEQ ID NO: 5
Humanin analog AGA-HNG amino acid sequence
maagafscll lltgeidlpv krra SEQ ID NO: 6
Humanin analog HN17 amino acid sequence
prgfsclll tseidlp SEQ ID NO: 7
Humanin analog HNG17 amino acid sequence
prgfsclll tgeidlp SEQ ID NO: 8
Humanin analog AGA-(C8R)HNG17 amino acid sequence
pagasrllll tgeidlp SEQ ID NO: 9
Humanin analog colivelin amino acid sequence
sallrsipap agasrllllt geidlp SEQ ID NO: 10
activity-dependent neurotrophic factor amino acid
sequence
sallrsipa SEQ ID NO: 11
combination of SEQ ID NO: 1, 2, 3, 4, 5, 6, 7 and
8 (17mer) amino acid sequence
(p/r/a)(r/a/g)(g/a)(f/a)s(c/r)lll(l/s)
t(s/t/g)(e/a)(i/t)dlp SEQ ID NO: 12
IGF-1, sense RT-PCR primer DNA sequence
TCTGAGGAGGCTGGAGATGT SEQ ID NO: 13
IGF-1 antisense RT-PCR primer DNA sequence
GTTCCGATGTTTTGCAGGTT SEQ ID NO: 14
IGF-1 receptor sense RT-PCR primer DNA sequence
GCGTCTTCACCACTCATTCC SEQ ID NO: 15
IGF-1 receptor antisense RT-PCR primer DNA
sequence
GCGCATAAGTTCAAACAGCA SEQ ID NO: 16
IGFBP-3 sense RT-PCR primer DNA sequence
GGCCCAGCAGAAATATCAAA
```

SEQ ID NO: 17
IGFBP-3 antisense RT-PCR primer DNA sequence
TACCAGGGTCTCCAACAAGG

SEQ ID NO: 18
Humanin analog HNGF6A amino acid sequence
MAPRGASCLLLLTGEIDLPVKRRA SEQ ID NO: 19
Z-Humanin (Zebrafish) amino acid sequence
MAKRGLNCLPHQVSEIDLSVQKRI SEQ ID NO: 20
Humanin analog HNGF6AK21A amino acid sequence
MAPRGASCLLLLTGEIDLPVARRA SEQ ID NO: 21,
forward primer for humanin
ATGGCTAAACGAGGGTTCAA SEQ ID NO: 22,
reverse primer for humanin
AAGCTCCATAGGGTCTTGTCG.

What is claimed is:

1. A pharmaceutical composition for increasing insulin sensitivity comprising a humanin analog in an amount effective to increase insulin sensitivity and a pharmaceutically acceptable carrier, wherein the humanin analog comprises the amino acid sequence MAPRGASCLLLLTGEIDLPVKRRA (SEQ ID NO:18) or the amino acid sequence MAPRGAS-CLLLLTGEIDLPVARRA (SEQ ID NO:20).

2. The pharmaceutical composition of claim 1, wherein the humanin analog comprises the amino acid sequence MAPR-GASCLLLLTGEIDLPVKRRA (SEQ ID NO:18).

3. The pharmaceutical composition of claim 1, wherein the humanin analog comprises the amino acid sequence MAPR-GASCLLLLTGEIDLPVARRA (SEQ ID NO:20).

4. The pharmaceutical composition of claim 1, wherein the humanin analog comprises the amino acid sequence of SEQ ID NO:10 conjugated to the amino acid sequence of SEQ ID NO:18 or SEQ ID NO:20.

5. The pharmaceutical composition of claim 1, wherein the humanin analog comprises the amino acid sequence of SEQ ID NO:10 at the N-terminus of the amino acid sequence of SEQ ID NO:18 or SEQ ID NO:20.

* * * * *

SEQUENCE LISTING

<160> NUMBER OF SEQ ID NOS: 22

<210> SEQ ID NO 1
<211> LENGTH: 24
<212> TYPE: PRT
<213> ORGANISM: Human

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 2
<211> LENGTH: 24
<212> TYPE: PRT
<213> ORGANISM: Artificial
<220> FEATURE:
<223> OTHER INFORMATION: Humanin-like peptide

<400> SEQUENCE: 2

Met Ala Arg Arg Gly Phe Ser Cys Leu Leu Leu Ser Thr Thr Ala Thr
1               5                   10                  15

Asp Leu Pro Val Lys Arg Arg Thr
            20

<210> SEQ ID NO 3
<211> LENGTH: 24
<212> TYPE: PRT
<213> ORGANISM: Artificial
<220> FEATURE:
<223> OTHER INFORMATION: Humanin analog F6A

<400> SEQUENCE: 3

Met Ala Pro Arg Gly Ala Ser Cys Leu Leu Leu Leu Thr Ser Glu Ile
1               5                   10                  15

Asp Leu Pro Val Lys Arg Arg Ala
            20

<210> SEQ ID NO 4
<211> LENGTH: 24
<212> TYPE: PRT
<213> ORGANISM: Artificial
<220> FEATURE:
<223> OTHER INFORMATION: Humanin analog S14G (HNG)

<400> SEQUENCE: 4

Met Ala Pro Arg Gly Phe Ser Cys Leu Leu Leu Leu Thr Gly Glu Ile
1               5                   10                  15

Asp Leu Pro Val Lys Arg Arg Ala
            20

```
<210> SEQ ID NO 5
<211> LENGTH: 24
<212> TYPE: PRT
<213> ORGANISM: Artificial
<220> FEATURE:
<223> OTHER INFORMATION: Humanin analog AGA-HNG

<400> SEQUENCE: 5

Met Ala Ala Gly Ala Phe Ser Cys Leu Leu Leu Leu Thr Gly Glu Ile
1               5                   10                  15

Asp Leu Pro Val Lys Arg Arg Ala
            20

<210> SEQ ID NO 6
<211> LENGTH: 17
<212> TYPE: PRT
<213> ORGANISM: Artificial
<220> FEATURE:
<223> OTHER INFORMATION: Humanin analog HN17

<400> SEQUENCE: 6

Pro Arg Gly Phe Ser Cys Leu Leu Leu Leu Thr Ser Glu Ile Asp Leu
1               5                   10                  15

Pro

<210> SEQ ID NO 7
<211> LENGTH: 17
<212> TYPE: PRT
<213> ORGANISM: Artificial
<220> FEATURE:
<223> OTHER INFORMATION: Humanin analog HNG17

<400> SEQUENCE: 7

Pro Arg Gly Phe Ser Cys Leu Leu Leu Leu Thr Gly Glu Ile Asp Leu
1               5                   10                  15

Pro

<210> SEQ ID NO 8
<211> LENGTH: 17
<212> TYPE: PRT
<213> ORGANISM: Artificial
<220> FEATURE:
<223> OTHER INFORMATION: Humanin analog AGA-(C8R)HNG17

<400> SEQUENCE: 8

Pro Ala Gly Ala Ser Arg Leu Leu Leu Leu Thr Gly Glu Ile Asp Leu
1               5                   10                  15

Pro

<210> SEQ ID NO 9
<211> LENGTH: 26
<212> TYPE: PRT
<213> ORGANISM: Artificial
<220> FEATURE:
<223> OTHER INFORMATION: Humanin analog colivelin

<400> SEQUENCE: 9

Ser Ala Leu Leu Arg Ser Ile Pro Ala Pro Ala Gly Ala Ser Arg Leu
1               5                   10                  15

Leu Leu Leu Thr Gly Glu Ile Asp Leu Pro
            20                  25
```

```
<210> SEQ ID NO 10
<211> LENGTH: 9
<212> TYPE: PRT
<213> ORGANISM: Artificial
<220> FEATURE:
<223> OTHER INFORMATION: neurotrophic factor

<400> SEQUENCE: 10

Ser Ala Leu Leu Arg Ser Ile Pro Ala
1               5

<210> SEQ ID NO 11
<211> LENGTH: 17
<212> TYPE: PRT
<213> ORGANISM: Artificial
<220> FEATURE:
<223> OTHER INFORMATION: 17mer combination of SEQ ID NOs: 1-9
<220> FEATURE:
<221> NAME/KEY: MISC_FEATURE
<222> LOCATION: (1)..(1)
<223> OTHER INFORMATION: x = Pro, Arg, or Ala
<220> FEATURE:
<221> NAME/KEY: MISC_FEATURE
<222> LOCATION: (2)..(2)
<223> OTHER INFORMATION: x = Arg, Ala, or Gly
<220> FEATURE:
<221> NAME/KEY: MISC_FEATURE
<222> LOCATION: (3)..(3)
<223> OTHER INFORMATION: x = Gly or Ala
<220> FEATURE:
<221> NAME/KEY: MISC_FEATURE
<222> LOCATION: (4)..(4)
<223> OTHER INFORMATION: x = Phe or Ala
<220> FEATURE:
<221> NAME/KEY: MISC_FEATURE
<222> LOCATION: (6)..(6)
<223> OTHER INFORMATION: x = Cys or Arg
<220> FEATURE:
<221> NAME/KEY: MISC_FEATURE
<222> LOCATION: (10)..(10)
<223> OTHER INFORMATION: x = Leu or Ser
<220> FEATURE:
<221> NAME/KEY: MISC_FEATURE
<222> LOCATION: (12)..(12)
<223> OTHER INFORMATION: x = Ser, Thr, or Gly
<220> FEATURE:
<221> NAME/KEY: MISC_FEATURE
<222> LOCATION: (13)..(13)
<223> OTHER INFORMATION: x = Glu or Ala
<220> FEATURE:
<221> NAME/KEY: MISC_FEATURE
<222> LOCATION: (14)..(14)
<223> OTHER INFORMATION: x = lle or Thr

<400> SEQUENCE: 11

Xaa Xaa Xaa Xaa Ser Xaa Leu Leu Leu Xaa Thr Xaa Xaa Xaa Asp Leu
1               5                   10                  15

Pro

<210> SEQ ID NO 12
<211> LENGTH: 20
<212> TYPE: DNA
<213> ORGANISM: Artificial
<220> FEATURE:
<223> OTHER INFORMATION: IGF-1 sense RT-PCR primer

<400> SEQUENCE: 12
tctgaggagg ctggagatgt                                              20

<210> SEQ ID NO 13
<211> LENGTH: 20
<212> TYPE: DNA
<213> ORGANISM: Artificial
```

```
<220> FEATURE:
<223> OTHER INFORMATION: IGF-1 antisense RT-PCR primer

<400> SEQUENCE: 13
gttccgatgt tttgcaggtt                                               20

<210> SEQ ID NO 14
<211> LENGTH: 20
<212> TYPE: DNA
<213> ORGANISM: Artificial
<220> FEATURE:
<223> OTHER INFORMATION: IGF-1 receptor sense RT-PCR primer

<400> SEQUENCE: 14
gcgtcttcac cactcattcc                                               20

<210> SEQ ID NO 15
<211> LENGTH: 20
<212> TYPE: DNA
<213> ORGANISM: Artificial
<220> FEATURE:
<223> OTHER INFORMATION: IGF-1 receptor antisense RT-PCR primer

<400> SEQUENCE: 15
gcgcataagt tcaaacagca                                               20

<210> SEQ ID NO 16
<211> LENGTH: 20
<212> TYPE: DNA
<213> ORGANISM: Artificial
<220> FEATURE:
<223> OTHER INFORMATION: IGFBP-3 sense RT-PCR primer

<400> SEQUENCE: 16
ggcccagcag aaatatcaaa                                               20

<210> SEQ ID NO 17
<211> LENGTH: 20
<212> TYPE: DNA
<213> ORGANISM: Artificial
<220> FEATURE:
<223> OTHER INFORMATION: IGFBP-3 antisense RT-PCR primer

<400> SEQUENCE: 17
taccagggtc tccaacaagg                                               20

<210> SEQ ID NO 18
<211> LENGTH: 24
<212> TYPE: PRT
<213> ORGANISM: Artificial
<220> FEATURE:
<223> OTHER INFORMATION: Humanin analog HNGF6A

<400> SEQUENCE: 18

Met Ala Pro Arg Gly Ala Ser Cys Leu Leu Leu Leu Thr Gly Glu Ile
1               5                   10                  15

Asp Leu Pro Val Lys Arg Arg Ala
            20

<210> SEQ ID NO 19
<211> LENGTH: 24
<212> TYPE: PRT
<213> ORGANISM: Danio rerio
```

```
<400> SEQUENCE: 19

Met Ala Lys Arg Gly Leu Asn Cys Leu Pro His Gln Val Ser Glu Ile
1               5                   10                  15

Asp Leu Ser Val Gln Lys Arg Ile
            20

<210> SEQ ID NO 20
<211> LENGTH: 24
<212> TYPE: PRT
<213> ORGANISM: Artificial
<220> FEATURE:
<223> OTHER INFORMATION: Humanin analog HNGF6AK21A

<400> SEQUENCE: 20

Met Ala Pro Arg Gly Ala Ser Cys Leu Leu Leu Leu Thr Gly Glu Ile
1               5                   10                  15

Asp Leu Pro Val Ala Arg Arg Ala
            20

<210> SEQ ID NO 21
<211> LENGTH: 20
<212> TYPE: DNA
<213> ORGANISM: Artificial
<220> FEATURE:
<223> OTHER INFORMATION: forward primer for Humanin

<400> SEQUENCE: 21
atggctaaac gagggttcaa                                              20

<210> SEQ ID NO 22
<211> LENGTH: 21
<212> TYPE: DNA
<213> ORGANISM: Artificial
<220> FEATURE:
<223> OTHER INFORMATION: reverse primer for Humanin

<400> SEQUENCE: 22
aagctccata gggtcttctc g                                            21
```